United States Patent
Antoniades et al.

(10) Patent No.: US 12,067,714 B2
(45) Date of Patent: Aug. 20, 2024

(54) RADIOMIC SIGNATURE OF A PERIVASCULAR REGION

(71) Applicant: Oxford University Innovation Limited, Oxford (GB)

(72) Inventors: Charalambos Antoniades, Oxford (GB); Evangelos Oikonomou, Oxford (GB)

(73) Assignee: OXFORD UNIVERSITY INNOVATION LIMITED, Oxford (GB)

( * ) Notice: Subject to any disclaimer, the term of this patent is extended or adjusted under 35 U.S.C. 154(b) by 673 days.

(21) Appl. No.: 17/276,908

(22) PCT Filed: Sep. 18, 2019

(86) PCT No.: PCT/GB2019/052633
§ 371 (c)(1),
(2) Date: Mar. 17, 2021

(87) PCT Pub. No.: WO2020/058713
PCT Pub. Date: Mar. 26, 2020

(65) Prior Publication Data
US 2021/0374951 A1    Dec. 2, 2021

(30) Foreign Application Priority Data

Sep. 18, 2018 (GR) ............................. 20180100430
Nov. 5, 2018 (GB) .................................... 1818049

(51) Int. Cl.
*G06T 7/12* (2017.01)
*A61B 6/00* (2006.01)
(Continued)

(52) U.S. Cl.
CPC ............ *G06T 7/0012* (2013.01); *A61B 6/504* (2013.01); *A61B 6/5217* (2013.01); *G06T 7/40* (2013.01);
(Continued)

(58) Field of Classification Search
CPC .................... G06T 7/0012; G06T 7/40; G06T 2207/20081; G06T 2207/30048;
(Continued)

(56) References Cited

U.S. PATENT DOCUMENTS 9,811,904 B2    11/2017  Lambin et al.
2011/0257505 A1  10/2011  Suri
(Continued)

FOREIGN PATENT DOCUMENTS

EP    2 958 049 A2    12/2015
EP    3 409 187 A1    12/2018
(Continued)

OTHER PUBLICATIONS

International Search Report and Written Opinion for WO 2020/058713 (PCT/GB2019/052633), dated Dec. 5, 2019, pp. 1-14.
(Continued)

Primary Examiner — Michael R Neff
(74) Attorney, Agent, or Firm — Thomas|Horstemeyer, LLP

(57) ABSTRACT

A method for characterising a perivascular region using medical imaging data of a subject. The method comprises calculating the value of a radiomic signature of the perivascular region using the medical imaging data. Also disclosed is a method for deriving a radiomic signature for predicting cardiovascular risk. The method comprises obtaining a radiomic dataset and using the radiomic dataset to construct a perivascular radiomic signature. Also disclosed are systems for performing the aforementioned methods.

25 Claims, 13 Drawing Sheets

(51) Int. Cl.
*A61B 6/50* (2024.01)
*G06T 7/00* (2017.01)
*G06T 7/40* (2017.01)
*G16H 30/40* (2018.01)
*G16H 50/20* (2018.01)
*G06N 20/00* (2019.01)

(52) U.S. Cl.
CPC ............ *G16H 30/40* (2018.01); *G16H 50/20* (2018.01); *G06N 20/00* (2019.01); *G06T 2207/20081* (2013.01); *G06T 2207/30048* (2013.01); *G06T 2207/30101* (2013.01)

(58) Field of Classification Search
CPC .......... G06T 2207/30101; G16H 50/20; G16H 30/04; G06N 20/00; A61B 6/504; A61B 6/5217
USPC ......................................................... 382/128
See application file for complete search history.

(56) References Cited

U.S. PATENT DOCUMENTS

| | | |
|---|---|---|
| 2011/0257545 A1 | 10/2011 | Suri |
| 2014/0114618 A1 | 4/2014 | Fonte et al. |
| 2014/0270430 A1* | 9/2014 | Nair ...................... A61B 17/22 382/128 |
| 2017/0265832 A1 | 9/2017 | Antoniades |
| 2017/0352157 A1 | 12/2017 | Madabhushi et al. |
| 2018/0342058 A1 | 11/2018 | Madabhushi et al. |

FOREIGN PATENT DOCUMENTS

| | | |
|---|---|---|
| GB | 2557263 A | 6/2018 |
| WO | 2015/054597 A2 | 4/2015 |
| WO | 2015/061882 A1 | 5/2015 |
| WO | 2016/024128 A1 | 2/2016 |
| WO | 2018/078395 A1 | 5/2018 |

OTHER PUBLICATIONS

UK Search Report for GB 1818049.7, dated May 3, 3019, pp. 1-5.
Yu Lina et al: "iVAR: Interactive visual analytics of radiomics features from large-scale medical images", 2017 IEEE International Conference On Big Data (Big Data), IEEE, Dec. 11, 2017 (Dec. 11, 2017), pp. 3916-3923.
International Preliminary Report on Patentability for WO 2020/058713 (PCT/GB2019/052633), dated Mar. 23, 2021, pp. 1-7.
Japanese Office Action for Patent Application No. 2021-513856, dated Jun. 2, 2023, pp. 1-13 (Translation Included).
Chinese Office Action for Patent Application No. 2019800750761, dated Nov. 29, 2023, pp. 1-20 (Translation Included).

* cited by examiner

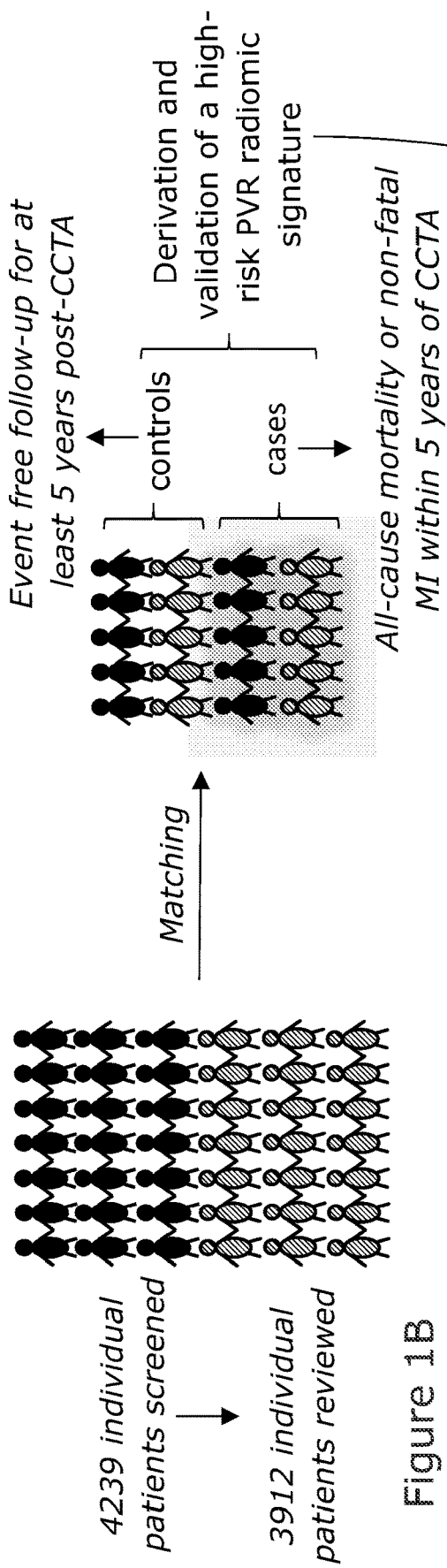
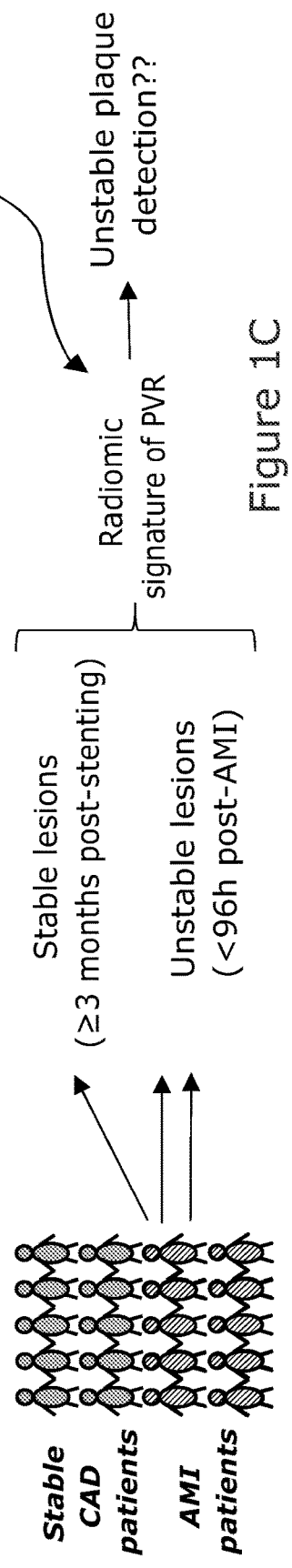
Figure 1B
Figure 1C

Improving prediction of future adverse events (Arm 1)

---

Model 1: age, gender, hypertension, dyslipidemia, diabetes mellitus, smoking
Model 2: Model 1 + Duke CAD Index + high-risk plaque + EAT volume + $CCS_{CCTA} > 0$
Model 3: Model 2 + $FAI_{PVAT}$
Model 4: Model 3 + PTI (Perivascular Texture Index)

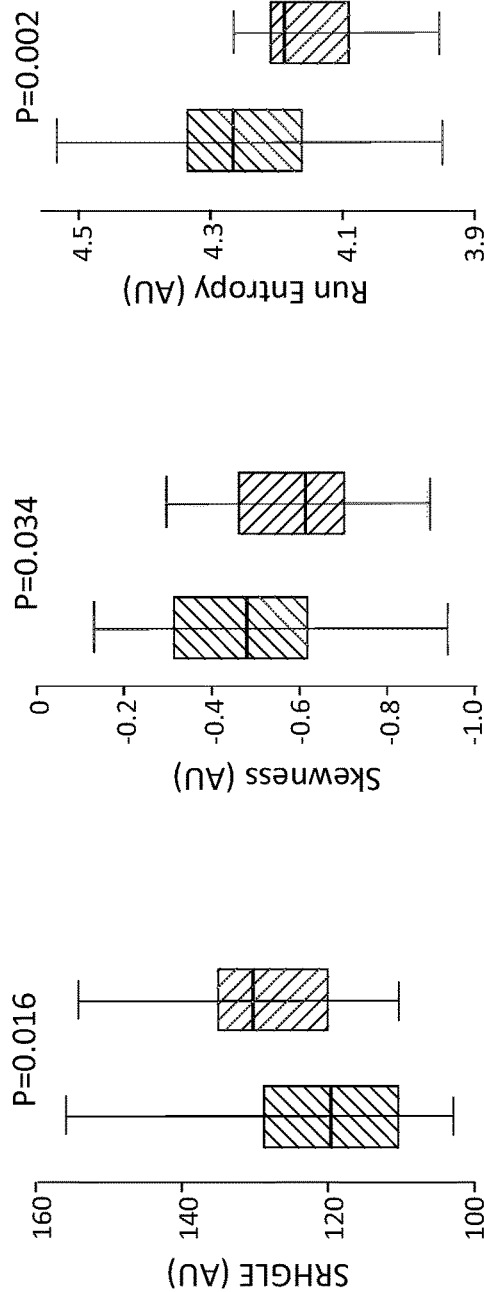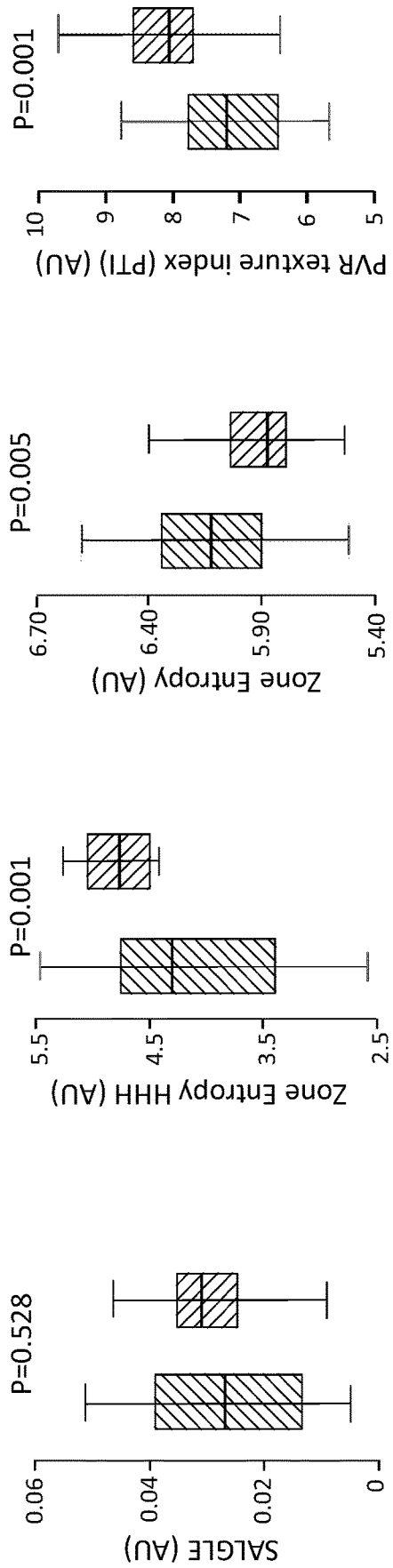

RADIOMIC SIGNATURE OF A PERIVASCULAR REGION

CROSS-REFERENCE TO RELATED APPLICATIONS

This application is the National Stage of International Application No. PCT/GB2019/052633, filed Sep. 18, 2019, which claims priority to GR 20180100430, filed Sep. 18, 2018 and GB 1818049.7, filed Nov. 5, 2018 which are entirely incorporated herein by reference.

FIELD OF THE INVENTION

The invention relates to methods of characterising a perivascular region, in particular using a radiomic signature, and systems for the same. The invention also relates to methods of deriving such signatures, and systems for the same.

BACKGROUND

Coronary artery disease (CAD) remains a major, leading cause of morbidity and mortality, despite significant advances in both primary and secondary cardiovascular prevention. Non-invasive diagnostic tests to assess the presence of CAD in patients presenting with typical or atypical symptoms, such as coronary computed tomography angiography (CCTA), are the pillars of modern cardiovascular diagnostics, e specially among individuals with low to mid pre-test likelihood of CAD. Such techniques traditionally rely on the detection of obstructive lesions or the presence and extent of coronary calcification for cardiovascular risk stratification. However, a significant number of patients have elevated residual cardiovascular risk despite optimal medical therapy. Residual vascular inflammation in particular is a driver of adverse events, contributing to both atherosclerotic plaque formation and destabilization, but may be hard to diagnose using conventional tests, such as circulating inflammatory biomarkers that are non-specific to vascular disease.

Interpretation of clinical imaging studies has traditionally relied on a subjective, operator-dependent, qualitative assessment of the imaged anatomy. This approach, although useful in the busy clinical setting, disregards the large amount of information that is included in all clinical scans.

WO 2016/024128 A1 and WO 2018/078395 A1 define a specific CCTA-based metric, namely the Fat Attenuation Index (FAI) or perivascular FAI ($FAI_{PVAT}$), which reflects the standardized, weighted average attenuation of a perivascular region around the human coronary arteries, which was found to be a sensitive and dynamic biomarker of coronary inflammation, and was subsequently identified as a strong and independent predictor of adverse cardiac events. In the presence of vascular inflammation, the release of pro-inflammatory molecules from the diseased vascular wall inhibits differentiation and lipid accumulation in pre-adipocytes within the perivascular tissue (PVT), resulting in smaller, less differentiated and lipid-free adipocyte cells. This is associated with a shift in the radiodensity (measured as attenuation values) of PTV in computed tomography (CT) imaging from more negative (closer to −190) to less negative (closer to −30) Hounsfield Unit (HU) values, which may be captured by the FAI. While both the biological meaning and clinical value of the FAI have been extensively validated, it does not adequate describe the full range of phenotypic variability observed in coronary PVT.

In a recent study, Kolossvary et al. showed that radiomic features can reliably identify plaques with the high-risk plaque feature napkin-ring sign, the identification of which normally relies on a qualitative assessment of plaque anatomy and the experienced eye of the operator (Kolossvary M, Karady J, Szilveszter B, et al. Radiomic Features Are Superior to Conventional Quantitative Computed Tomographic Metrics to Identify Coronary Plaques With Napkin-Ring Sign. Circ Cardiovasc Imaging 2017; 10(12): e006843). However, this approach focuses on phenotyping of the plaques themselves and neglects the PVT and the valuable information that can be gained therefrom.

What is needed is a method or tool that provides prognostic value for cardiovascular risk over and above current CCTA-based risk stratification tools, such as the presence and extent of CAD, presence of high-risk plaque features, coronary calcium and the recently described $FAI_{PVAT}$.

SUMMARY OF THE INVENTION

According to a first aspect of the invention, there is provided a method for characterising a perivascular region (for example its phenotype, e.g. composition and/or texture) using medical imaging data of a subject. The method may comprise calculating the value of a radiomic signature of the perivascular region using the medical imaging data. The radiomic signature may be calculated on the basis of measured values of at least two radiomic features of the perivascular region. The measured values of the at least two radiomic features may be calculated from or using the medical imaging data.

The radiomic signature may provide a measure of the texture of the perivascular region.

At least one of the at least two radiomic features may provide a measure of the texture of the perivascular region.

The radiomic signature may be predictive of cardiovascular risk.

The radiomic signature may be predictive of the likelihood of the subject experiencing a major adverse cardiovascular event.

The radiomic signature may be predictive of the likelihood of the subject experiencing a cardiac-specific major adverse cardiovascular event.

The radiomic signature may be indicative of cardiovascular health.

The radiomic signature may be indicative of vascular disease. For example, the radiomic feature may be indicative of vascular inflammation.

At least one of the at least two radiomic features may be calculated from a wavelet transformation of the attenuation values.

Each of the at least two radiomic features may be volume-independent and/or orientation-independent.

The at least two radiomic features may be selected from the radiomic features of clusters 1 to 9, wherein the at least two radiomic features are each selected from different clusters, wherein:
  cluster 1 consists of Short Run High Gray Level Emphasis, High Gray Level Emphasis, High Gray Level Run Emphasis, Autocorrelation, Sum Average, Joint Average, and High Gray Level Zone Emphasis;
  cluster 2 consists of Skewness, Skewness LLL, Kurtosis, 90th Percentile, 90th Percentile LLL, Median LLL, Kurtosis LLL, and Median;
  cluster 3 consists of Run Entropy, Dependence Entropy LLL, Dependence Entropy, Zone Entropy LLL, Run Entropy LLL, and Mean LLL;

cluster 4 consists of Small Area Low Gray Level Emphasis, Low Gray Level Zone Emphasis, Short Run Low Gray Level Emphasis, Low Gray Level Run Emphasis, Low Gray Level Emphasis, Small Dependence Low Gray Level Emphasis, Gray Level Variance LLL (GLSZM), Gray Level Variance (GLDM), Variance, Gray Level Variance (GLDM), Difference Variance LLL, Gray Level Variance LLL (GLRLM), Variance LLL, Gray Level Variance LLL (GLDM), Sum of Squares, Contrast LLL, Mean Absolute Deviation, Interquartile Range, Robust Mean Absolute Deviation, Long Run Low Gray Level Emphasis, Difference Variance, Gray Level Variance (GLSZM), Inverse Difference Moment Normalized, Mean Absolute Deviation LLL, Sum of Squares LLL, and Contrast;

cluster 5 consists of Zone Entropy, Gray Level Non Uniformity Normalized (GLRLM), Gray Level Non Uniformity Normalized LLL (GLRLM), Sum Entropy, Joint Energy, Entropy, Gray Level Non Uniformity Normalized (GLDM), Joint Energy, Gray Level Non Uniformity Normalized LLL (GLDM), Uniformity LLL, Sum Entropy LLL, and Uniformity;

cluster 6 consists of Zone Entropy HHH, Size Zone Non Uniformity Normalized HHH, and Small Area Emphasis HHH;

cluster 7 consists of Strength, Coarseness HLL, Coarseness, Coarseness LHL, Coarseness LLL, Coarseness LLH, Coarseness HHH, Coarseness HLH, Coarseness HHL, and Coarseness LHH;

cluster 8 consists of Cluster Tendency LLL, Cluster Tendency, Sum of Squares LLL, Mean Absolute Deviation LLL, Gray Level Variance LLL (GLDM), Variance LLL, Gray Level Variance LLL (GLRLM), Gray Level Variance (GLRLM), Robust Mean Absolute Deviation LLL, Gray Level Variance (GLDM), Variance, Mean Absolute Deviation, Cluster Prominence, Sum Entropy LLL, Interquartile Range LLL, Gray Level Variance LLL (GLSZM), Sum of Squares, Robust Mean Absolute Deviation, Sum Entropy, Interquartile Range, Cluster Prominence LLL, Entropy LLL, 10th Percentile LLL, 10th Percentile; and cluster 9 consists of Size Zone Non Uniformity LLL, Dependence Non Uniformity HLL, Gray Level Non Uniformity HLL (GLSZM), Gray Level Non Uniformity (GLSZM), Run Length Non Uniformity HHL, Run Length Non Uniformity LHL, Dependence Non Uniformity LHL, Dependence Non Uniformity, Run Length Non Uniformity HLH, Busyness, Run Length Non Uniformity LLH, Dependence Non Uniformity LLH, Dependence Non Uniformity LLL, Size Zone Non Uniformity, Energy HLL, Run Length Non Uniformity LHH, Size Zone Non Uniformity HLL, Gray Level Non Uniformity LLH (GLSZM), Gray Level Non Uniformity LHL (GLSZM), Gray Level Non Uniformity LLL (GLSZM), Run Length Non Uniformity HLL, Gray Level Non Uniformity HLH (GLSZM), Gray Level Non Uniformity HHL (GLSZM), Run Length Non Uniformity, and Run Length Non Uniformity HHH.

Clusters 1 to 9 may instead be defined as follows:
cluster 1 consists of Short Run High Gray Level Emphasis, High Gray Level Emphasis, High Gray Level Run Emphasis, Autocorrelation, Sum Average, and Joint Average;
cluster 2 consists of Skewness, Skewness LLL, Kurtosis, 90th Percentile, 90th Percentile LLL, Median LLL, and Kurtosis LLL;

cluster 3 consists of Run Entropy, Dependence Entropy LLL, Dependence Entropy, and Zone Entropy LLL;

cluster 4 consists of Small Area Low Gray Level Emphasis, Low Gray Level Zone Emphasis, Short Run Low Gray Level Emphasis, Low Gray Level Run Emphasis, Low Gray Level Emphasis, Small Dependence Low Gray Level Emphasis, Gray Level Variance LLL (GLSZM), Gray Level Variance (GLDM), Variance, Gray Level Variance (GLDM), and Difference Variance LLL;

cluster 5 consists of Zone Entropy, Gray Level Non Uniformity Normalized (GLRLM), and Gray Level Non Uniformity Normalized LLL (GLRLM);

cluster 6 consists of Zone Entropy HHH, and Size Zone Non Uniformity Normalized HHH;

cluster 7 consists of Strength, Coarseness HLL, Coarseness, Coarseness LHL, Coarseness LLL, Coarseness LLH, and Coarseness HHH;

cluster 8 consists of Cluster Tendency LLL, Cluster Tendency, Sum of Squares LLL, Mean Absolute Deviation LLL, Gray Level Variance LLL (GLDM), Variance LLL, Gray Level Variance LLL (GLRLM), Gray Level Variance (GLRLM), Robust Mean Absolute Deviation LLL, Gray Level Variance (GLDM), Variance, Mean Absolute Deviation, Cluster Prominence, Sum Entropy LLL, Interquartile Range LLL, Gray Level Variance LLL (GLSZM), Sum of Squares, Robust Mean Absolute Deviation, Sum Entropy, Interquartile Range, Cluster Prominence LLL, Entropy LLL, 10th Percentile LLL, and 10th Percentile; and cluster 9 consists of Size Zone Non Uniformity LLL, Dependence Non Uniformity HLL, Gray Level Non Uniformity HLL (GLSZM), Gray Level Non Uniformity (GLSZM), Run Length Non Uniformity HHL, Run Length Non Uniformity LHL, Dependence Non Uniformity LHL, Dependence Non Uniformity, Run Length Non Uniformity HLH, Busyness, Run Length Non Uniformity LLH, Dependence Non Uniformity LLH, Dependence Non Uniformity LLL, Size Zone Non Uniformity, Energy HLL, Run Length Non Uniformity LHH, Size Zone Non Uniformity HLL, Gray Level Non Uniformity LLH (GLSZM), and Gray Level Non Uniformity LHL (GLSZM).

Clusters 1 to 9 may instead be defined as follows:
cluster 1 consists of Short Run High Gray Level Emphasis, High Gray Level Emphasis, High Gray Level Run Emphasis, Autocorrelation, Sum Average, and Joint Average;
cluster 2 consists of Skewness, Skewness LLL, Kurtosis, and 90th Percentile;
cluster 3 consists of Run Entropy, Dependence Entropy LLL, and Dependence Entropy;
cluster 4 consists of Small Area Low Gray Level Emphasis, Low Gray Level Zone Emphasis, Short Run Low Gray Level Emphasis, Low Gray Level Run Emphasis, Low Gray Level Emphasis, and Small Dependence Low Gray Level Emphasis;
cluster 5 consists of Zone Entropy, and Gray Level Non Uniformity Normalized (GLRLM);
cluster 6 consists of Zone Entropy HHH;
cluster 7 consists of Strength, Coarseness HLL, Coarseness, Coarseness LHL, Coarseness LLL, and Coarseness LLH;
cluster 8 consists of Cluster Tendency LLL, Cluster Tendency, Sum of Squares LLL, Mean Absolute Deviation LLL, Gray Level Variance LLL (GLDM), Variance LLL, Gray Level Variance LLL (GLRLM), Gray Level Variance (GLRLM), Robust Mean Absolute Deviation LLL, Gray Level Variance (GLDM), Variance, Mean Absolute Deviation, Cluster Prominence, Sum Entropy LLL, Interquartile Range LLL, Gray Level Variance LLL (GLSZM), Sum of Squares, Robust Mean Absolute Deviation, Sum Entropy, Interquartile Range, Cluster Prominence LLL, Entropy LLL, 10th Percentile LLL, and 10th Percentile; and cluster 9 consists of Size Zone Non Uniformity LLL, Dependence Non Uniformity HLL, Gray Level Non Uniformity HLL (GLSZM), Gray Level Non Uniformity (GLSZM), Run Length Non Uniformity HHL, Run Length Non Uniformity LHL, Dependence Non Uniformity LHL, Dependence Non Uniformity, Run Length Non Uniformity HLH, Busyness, Run Length Non Uniformity LLH, Dependence Non Uniformity LLH, Dependence Non Uniformity LLL, and Size Zone Non Uniformity.

Clusters 1 to 9 may instead be defined as follows:
cluster 1 consists of Short Run High Gray Level Emphasis, High Gray Level Emphasis, High Gray Level Run Emphasis, and Autocorrelation;
cluster 2 consists of Skewness, and Skewness LLL;
cluster 3 consists of Run Entropy, and Dependence Entropy LLL;
cluster 4 consists of Small Area Low Gray Level Emphasis, and Low Gray Level Zone Emphasis;
cluster 5 consists of Zone Entropy;
cluster 6 consists of Zone Entropy HHH;
cluster 7 consists of Strength;
cluster 8 consists of Cluster Tendency LLL, Cluster Tendency, Sum of Squares LLL, Mean Absolute Deviation LLL, Gray Level Variance LLL (GLDM), Variance LLL, Gray Level Variance LLL (GLRLM), Gray Level Variance (GLRLM), Robust Mean Absolute Deviation LLL, Gray Level Variance (GLDM), Variance, Mean Absolute Deviation, Cluster Prominence, Sum Entropy LLL, Interquartile Range LLL, Gray Level Variance LLL (GLSZM), Sum of Squares, Robust Mean Absolute Deviation, Sum Entropy, Interquartile Range, Cluster Prominence LLL, Entropy LLL, 10th Percentile LLL, and 10th Percentile; and cluster 9 consists of Size Zone Non Uniformity LLL, Dependence Non Uniformity HLL, Gray Level Non Uniformity HLL (GLSZM), Gray Level Non Uniformity (GLSZM), Run Length Non Uniformity HHL, and Run Length Non Uniformity LHL.

Clusters 1 to 9 may instead be defined as follows:
cluster 1 consists of Short Run High Gray Level Emphasis, High Gray Level Emphasis, and High Gray Level Run Emphasis;
cluster 2 consists of Skewness, and Skewness LLL;
cluster 3 consists of Run Entropy;
cluster 4 consists of Small Area Low Gray Level Emphasis, and Low Gray Level Zone Emphasis;
cluster 5 consists of Zone Entropy;
cluster 6 consists of Zone Entropy HHH;
cluster 7 consists of Strength;
cluster 8 consists of Cluster Tendency LLL, Cluster Tendency, Sum of Squares LLL, Mean Absolute Deviation LLL, Gray Level Variance LLL (GLDM), Variance LLL, Gray Level Variance LLL (GLRLM), Gray Level Variance (GLRLM), Robust Mean Absolute Deviation LLL, Gray Level Variance (GLDM), Variance, Mean Absolute Deviation, Cluster Prominence, Sum Entropy LLL, Interquartile Range LLL, Gray Level Variance LLL (GLSZM), Sum of Squares, Robust Mean Absolute Deviation, and Sum Entropy; and cluster 9 consists of Size Zone Non Uniformity LLL.

Clusters 1 to 9 may instead be defined as follows:
cluster 1 consists of Short Run High Gray Level Emphasis, High Gray Level Emphasis, and High Gray Level Run Emphasis;
cluster 2 consists of Skewness, Skewness LLL, Kurtosis, 90th Percentile, Median LLL, Kurtosis LLL, and Median;
cluster 3 consists of Run Entropy, Run Entropy LLL, and Mean LLL;
cluster 4 consists of Small Area Low Gray Level Emphasis, Low Gray Level Zone Emphasis, and Gray Level Variance (GLSZM);
cluster 5 consists of Zone Entropy, Gray Level Non Uniformity Normalized (GLRLM), and Uniformity;
cluster 6 consists of Zone Entropy HHH;
cluster 7 consists of Strength;
cluster 8 consists of Cluster Tendency LLL, Cluster Tendency, Mean Absolute Deviation LLL, Gray Level Variance LLL (GLDM), Variance LLL, Gray Level Variance LLL (GLRLM), Robust Mean Absolute Deviation LLL, Gray Level Variance LLL (GLSZM), Interquartile Range LLL, Sum Entropy LLL, Gray Level Variance (GLRLM), Variance, Gray Level Variance (GLDM), Mean Absolute Deviation, Sum Entropy, Robust Mean Absolute Deviation, Interquartile Range, Entropy LLL, 10th Percentile LLL, 10th Percentile, Entropy, Uniformity LLL, Gray Level Non Uniformity Normalized LLL (GLDM), Gray Level Non Uniformity Normalized LLL (GLRLM), Root Mean Squared, Gray Level Non Uniformity Normalized (GLDM), Root Mean Squared LLL, and Long Run Low Gray Level Emphasis; and cluster 9 consists of Size Zone Non Uniformity LLL, Busyness, and Size Zone Non Uniformity.

The at least two radiomic features may be selected from: Median LLL, Mean LLL, Median, Root Mean Squared LLL, Mean, Kurtosis, Root Mean Squared, Run Entropy LLL (GLRLM), Uniformity, 90th Percentile, Gray Level Non-Uniformity Normalized (GLRLM), Uniformity LLL, Skewness, Gray Level Non-Uniformity Normalized LLL (GLRLM), 10th Percentile LLL, Skewness LLL, 10th Percentile, Entropy, Interquartile Range LLL, Robust Mean Absolute Deviation LLL, Run Entropy (GLRLM), Interquartile Range, Sum Entropy (GLCM), Gray Level Non-Uniformity Normalized LLL (GLRLM), Dependence Non-Uniformity LHL (GLDM), Kurtosis LLL, Run Length Non-Uniformity HHL (GLRLM), Entropy LLL, Robust Mean Absolute Deviation, Sum Entropy LLL (GLCM), 90th Percentile LLL, Run Entropy HHL (GLRLM), Energy, Energy LLL, Strength (NGTDM), Autocorrelation (GLCM), Mean Absolute Deviation LLL, High Gray Level Emphasis (GLDM), Joint Average (GLCM), Sum Average (GLCM), Short Run High Gray Level Emphasis (GLRLM), Energy HHH, High Gray Level Run Emphasis (GLRLM), Run Entropy HHH (GLRLM), Energy HHL, and Mean Absolute Deviation.

The at least two radiomic features may be selected from the radiomic features of clusters 1 to 8. The at least two radiomic features may be selected from the radiomic features of clusters 1 to 7. The at least two radiomic features may be selected from the radiomic features of clusters 1 to 6. The at least two radiomic features may be selected from the radiomic features of clusters 1 to 5. The at least two radiomic features may be selected from the radiomic features of clusters 1 to 4. The at least two radiomic features may be selected from the radiomic features of clusters 1 to 3. The at least two radiomic features may be selected from the radiomic features of clusters 1 and 2.

The at least two radiomic features may comprise at least three radiomic features. The at least two radiomic features may comprise at least four radiomic features. The at least two radiomic features may comprise at least five radiomic features. The at least two radiomic features may comprise at least six radiomic features. The at least two radiomic features may comprise at least seven radiomic features. The at least two radiomic features may comprise at least eight radiomic features. The at least two radiomic features may comprise at least nine radiomic features.

The at least two radiomic features may comprise six radiomic features, wherein the six radiomic features are Short Run High Gray Level Emphasis, Skewness, Run Entropy, Small Area Low Gray Level Emphasis, Zone Entropy HHH, and Zone Entropy.

The at least two radiomic features may comprise nine radiomic features, wherein the nine radiomic features are Short Run High Gray Level Emphasis, Skewness, Run Entropy, Small Area Low Gray Level Emphasis, Zone Entropy HHH, Zone Entropy, Strength, Cluster Tendency LLL, and Size Zone Non Uniformity.

The radiomic signature may comprise a weighted sum of the values of each of the at least two radiomic features. The radiomic signature may be linearly related to the weighted sum of the values of each of the at least two radiomic features.

The medical imaging data may comprise attenuation values for each of a plurality of voxels corresponding to at least the perivascular region. The plurality of voxels may also correspond to the blood vessel around which the perivascular region is disposed.

The method may further comprise identifying the perivascular region (or substance, tissue or type of perivascular tissue, for example adipose tissue) using the medical imaging data. The perivascular region may be identified as all voxels of the medical imaging data having an attenuation (or radiodensity) value falling within a given range of attenuation values and/or located within a given radial distance from an outer vessel wall (i.e. the vessel adjacent to the perivascular tissue). The given range of attenuation values may be from about −190 to about −30 Hounsfield Units, for example if the perivascular region corresponds to perivascular adipose tissue. The given range of attenuation values may be from about −30 to about +30 Hounsfield Units, for example if the perivascular region corresponds to water. The given radial distance may be a distance related to one or more dimensions of the adjacent vessel. The given radial distance may be equal to the diameter of the adjacent vessel. The given radial distance may be a fixed value, for example 5 mm.

The perivascular region may be adjacent to or surround a coronary artery, carotid artery, aorta or any other artery in the human body. For example, the perivascular region may be adjacent to or surround the proximal and/or mid right coronary artery. The method may further comprise segmenting the perivascular region. The method may further comprise calculating the values of the radiomic features from the segmented perivascular region.

The values of each of the at least two radiomic features may be calculated from raw attenuation values, binned attenuation values, or a wavelet transformation of the attenuation values.

The method may further comprise predicting the risk of the subject experiencing a major adverse cardiac event based on the calculated value of the radiomic signature.

The method may further comprise predicting the risk of the subject experiencing a cardiac-specific major adverse cardiac event based on the calculated value of the radiomic signature.

The method may further comprise determining whether the subject has vascular disease based on the calculated value of the radiomic signature. The vascular disease may be selected from the group consisting of atherosclerosis, vascular calcification, intima hyperplasia, vascular aneurysm and vascular inflammation.

The method may further comprise determining whether the subject has coronary heart disease based on the calculated value of the radiomic signature.

The calculated value of the radiomic signature may be used to discriminate unstable from stable coronary lesions. The perivascular region may be a peri-lesion region.

According to a second aspect of the invention, there is provided method for deriving a radiomic signature for predicting cardiovascular risk. The method may comprise using a dataset, for example a radiomic dataset, to construct a perivascular radiomic signature or score for predicting cardiovascular risk. The radiomic signature may be calculated on the basis of at least two radiomic features of a perivascular region. The dataset may comprise the measured values of a plurality of radiomic features of a perivascular region obtained from medical imaging data for each of a plurality of individuals. The plurality of individuals may comprise a first group of individuals having reached a clinical endpoint indicative of cardiovascular risk and a second group of individuals having not reached a clinical endpoint indicative of cardiovascular risk.

The first group of individuals may have reached a clinical endpoint indicative of cardiovascular risk within a subsequent period after the medical imaging data were collected and a second group of individuals may not have reached a clinical endpoint indicative of cardiovascular risk within the subsequent period after the medical imaging data were collected.

Each of the at least two radiomic features may be selected to be collinear (or correlated) with a corresponding partner radiomic feature that is significantly (i.e. statistically significant) associated with the clinical endpoint, for example as determined or calculated from the dataset. The partner radiomic features of the at least two radiomic features may each be different to one another.

Each of the at least two radiomic features may be selected to be, or to be collinear with, different significant radiomic features that are significantly associated with the clinical endpoint (as determined from the dataset, i.e. identified from the dataset as being significantly associated with the clinical endpoint). The method may therefore comprise identifying significant radiomic features from amongst the plurality of radiomic features that are each significantly associated with the clinical endpoint, the at least two radiomic features each being selected to be, or to be collinear with, different significant radiomic features.

The significant radiomic features may be selected to be not collinear with each other. For example, the method may further comprise identifying a subset of the plurality of radiomic features (e.g. a subset of the significant radiomic features) that are not collinear with each other, the at least two radiomic features each being selected to be, or to be collinear with, different radiomic features belonging to the subset.

Each of the partner radiomic features may be selected to be not collinear with any of the other partner radiomic features.

At least one of the at least two radiomic features may be its own partner radiomic feature.

Each of the at least two radiomic features may be selected to be significantly associated with the clinical endpoint, for example as determined or calculated from the dataset.

The method may comprise identifying a plurality of clusters of radiomic features. Each cluster may comprise a subset of the plurality of radiomic features. Each cluster may include an original radiomic feature with which each of the other radiomic features in that cluster is selected to be collinear, for example as determined or calculated from the dataset. The at least two radiomic features may each be selected from different clusters.

Each of the original radiomic features may be selected to be not collinear with any of the original radiomic features of any of the other clusters, for example as determined or calculated from the dataset.

Each of the radiomic features in each cluster may be selected to be collinear with all of the other radiomic features in the same cluster, for example as determined or calculated from the dataset.

Each of the original radiomic features may be selected to be significantly associated with the clinical endpoint, for example as determined or calculated from the dataset.

Each of the original radiomic features may be selected to be the most strongly associated with the clinical endpoint of all the radiomic features in its cluster, for example as determined or calculated from the dataset.

The at least two radiomic features may be selected to be not collinear with each other, for example as determined or calculated from the dataset.

Two radiomic features may be identified as collinear if they are correlated to an extent greater than a correlation threshold.

The collinearity between radiomic features may be calculated using Spearman's rho coefficient. Alternatively, collinearity between radiomic features may be calculated using other measures of pairwise correlation, such as Pearson's correlation coefficient (Pearson's r).

The correlation threshold may be at least about |0.75|, for example about |rho|=0.75.

A radiomic feature may be identified as being significantly associated with the clinical endpoint if it is associated with the clinical endpoint above a significance threshold, for example as determined or calculated from the dataset. The significance threshold may be at least about $\alpha=0.05$, e.g. about $\alpha=0.05$.

The association of the radiomic features with the clinical endpoint may be calculated based on a receiver operating characteristic (ROC) curve analysis, in particular using an area under the curve (AUC) measurement (i.e. the C-statistic), as will be readily understood by those skilled in the art.

A Bonferroni correction may be applied to the significance threshold.

A principal component analysis of the plurality of radiomic features may be performed, for example using the dataset (specifically on the values of the radiomic features of the plurality of individuals). The Bonferroni correction may be based on the number of principal components that account for a given amount of the observed variation, as determined from the principal component analysis. The given amount of observed variation may be at least about 99.5%, for example about 99.5%.

The radiomic signature may be constructed to be correlated with the clinical endpoint. The radiomic signature may be constructed to be significantly associated with the clinical endpoint.

The radiomic signature may be identified as being significantly associated with the clinical endpoint if it is associated with the clinical endpoint above a significance threshold, for example as determined or calculated from the dataset. The significance threshold may be at least about 0.05, e.g. about $\alpha=0.05$.

The dataset may be divided into data for a training cohort of individuals and a validation cohort of individuals. The step of constructing the radiomic signature may comprise deriving the signature using data for at least the training cohort. The step of constructing the radiomic signature may comprise validating the signature using data for the validation cohort.

A radiomic feature may be identified as being significantly associated with the clinical endpoint only if it is significantly associated with the clinical endpoint in both cohorts. The radiomic signature may be identified as being significantly associated with the clinical endpoint if it is significantly associated with the clinical endpoint in the training cohort.

Each of the at least two radiomic features may be volume-independent. Each of the at least two radiomic features may be orientation-independent. The plurality of radiomic features may each be volume- and/or orientation-independent.

Any volume- and/or orientation-dependent radiomic features may be removed from the plurality of radiomic features prior to selection of the at least two radiomic features.

The at least two radiomic features may be selected to be stable, for example as determined or calculated from the dataset. For example, the at least two radiomic features may be selected from amongst those that are identified as being stable, for example as determined or calculated from the dataset.

All unstable features may be removed from the plurality of radiomic features. For example, all unstable features may be removed from the plurality of radiomic features before the at least two radiomic features are selected.

A radiomic feature may be identified as being unstable if the intraclass correlation coefficient (ICC) for that radiomic feature (calculated for repeat measurements or scans) is less than a stability threshold. The stability threshold may be at least about 0.9, for example 0.9. The intraclass correlation coefficient may be calculated based on the Z-scores (or standard score, i.e. expressed in terms of the number of standard deviations from the mean) of the radiomic features.

The step of constructing the radiomic signature may comprise refining the contribution of the at least two radiomic features to the radiomic signature to increase the association or correlation of the radiomic signature with the clinical endpoint. The radiomic signature may be constructed to be significantly associated with the clinical endpoint.

The association of the radiomic signature with the clinical endpoint may be calculated based on a receiver operating characteristic (ROC) curve analysis, in particular using an area under the curve (AUC) measurement (i.e. the C-statistic), as will be readily understood by those skilled in the art.

The step of constructing the radiomic signature may be performed using a machine learning algorithm.

The step of constructing the radiomic signature may be performed using leave-p-out internal cross-validation.

The step of constructing the radiomic signature may be performed using leave-one-out internal cross-validation.

The step of constructing the radiomic signature may be performed using elastic network regression.

The radiomic signature may comprise a weighted sum of the at least two radiomic features.

The radiomic signature may be linearly related to the weighted sum of the at least two radiomic features.

The step of constructing the radiomic signature may comprise adjusting the relative weightings of each of the at least two radiomic features to increase the association or correlation of the radiomic signature with the clinical endpoint.

The radiomic signature may be constructed to provide a measure of the texture of the perivascular region.

At least one of the at least two radiomic features may provide a measure of the texture of the perivascular region. For example, each of the at least two radiomic features may provide a measure of the texture of the perivascular region (i.e. each of the at least two radiomic features may be texture statistics).

The clinical endpoint may be the composite endpoint of major adverse cardiac events. The clinical endpoint may be the composite endpoint of cardiac-specific major adverse cardiac events.

The methods of the invention may also comprise the step of calculating the radiomic features from the medical imaging data.

The radiomic signature of the invention may also be calculated on the basis of further radiomic features in addition to the at least two radiomic features referred to above.

Thus, it may be said that the radiomic signature is calculated on the basis of a plurality of radiomic features, and the plurality of radiomic features may comprise the at least two radiomic features. For example, the method for deriving a radiomic signature for predicting cardiovascular risk may comprise using a dataset, in particular a radiomic dataset, to construct a perivascular radiomic signature or score for predicting cardiovascular risk. The radiomic signature may be calculated on the basis of a (second) plurality of perivascular radiomic features (i.e. radiomic features of a perivascular region). The dataset may comprise the measured values of a (first) plurality of perivascular radiomic features of a perivascular region obtained from medical imaging data for each of a plurality of individuals. The plurality of individuals may comprise a first group of individuals having reached a clinical endpoint indicative of cardiovascular risk and a second group of individuals having not reached a clinical endpoint indicative of cardiovascular risk. The second plurality of perivascular radiomic features may be selected from amongst the first plurality of perivascular radiomic features, in particular to provide a radiomic signature for predicting cardiovascular risk, as determined from or using the dataset, for example using a machine learning algorithm. The radiomic signature may therefore be calculated on the basis of further radiomic features (for example selected from the (first) plurality of radiomic features) in addition to the at least two radiomic features.

The method may further comprise configuring a system for calculating the value of the radiomic signature for a patient. For example, the method may further comprise configuring a system for characterising a perivascular region of the patient or subject by calculating the value of the derived radiomic signature for the patient or subject. The system may be configured to calculate the value of the derived radiomic signature using or based on medical imaging data of at least a perivascular region of the patient or subject. The system may be configured to calculate the value of the derived radiomic signature using or based at least on the values of the at least two (or second plurality) of radiomic features of the perivascular region of the patient or subject.

The method may therefore be for deriving a perivascular radiomic signature and configuring a system for characterising a perivascular region of a patient using the derived radiomic signature.

The system may be configured to receive the medical imaging data or values of the at least two (or second plurality of) radiomic features as an input. The system may be configured to output (e.g. display) the calculated value of the radiomic signature or a value based on the calculated value of the radiomic signature. The system may be configured to output an indication of the patient's cardiovascular risk and/or vascular health. The system may be configured to output an indication of the risk of the patient experiencing an adverse cardiovascular event. The system may be a computer system.

The method may comprise providing instructions for configuring a system for calculating the value of the derived radiomic signature for a patient or subject.

The method may further comprise calculating the value of the derived radiomic signature for a perivascular region of a patient or subject. For example, the method may further comprise characterising a perivascular region of a patient or subject by calculating the value of the derived radiomic signature. The value of the derived radiomic signature may be calculated based on or using medical imaging data of at least the perivascular region of the patient or subject. The value of the derived radiomic signature may be calculated using or based at least on the values of the at least two (or second plurality of) radiomic features of the perivascular region of the patient or subject.

The method may therefore be for deriving a perivascular radiomic signature and characterising a perivascular region using the derived radiomic signature.

According to a third aspect of the invention, there is provided a system configured to perform any of the methods as described above. The system may be a computer system. The system may comprise a processor configured to perform the steps of the method. The system may comprise a memory loaded with executable instructions for performing the steps of the method.

According to a fourth aspect of the invention, there is provided use of a perivascular radiomic signature for any of the above-described purposes, for example to characterise a perivascular region, to detect vascular disease, or to predict cardiovascular risk. The perivascular radiomic signature may be calculated on the basis of measured values of a plurality of perivascular radiomic features of the perivascular region.

The medical imaging data may be radiographic data. The medical imaging data may be computed tomography data.

The perivascular region may be or may comprise perivascular tissue, for example perivascular adipose tissue. The perivascular region may also comprise water, and/or other soft tissue structures within the perivascular region.

BRIEF DESCRIPTION OF THE FIGURES

The invention will now be described with reference to the appended figures, in which:

FIG. 1 illustrates the study methodology and design. FIGS. 1B and 1C illustrate a summary of Arms 1 and 2 of the study, respectively. AMI: acute myocardial infarction; CAD: coronary artery disease; CCTA: coronary computed tomography angiography; MACE: major adverse cardiovascular events; PVR: perivascular region; H/L: high/low wavelet transformation; VOI: volume of interest.

FIG. 2 summarises the building of the high-risk perivascular region radiomic signature.

FIG. 5 illustrates various aspects of the principal component analysis of coronary perivascular region radiomic features.

FIG. 8 shows that perivascular region texture phenotyping using a radiomic signature according to the invention may be used for detection of unstable coronary lesions. FIGS. 8A-G show box and whisker plots the six radiomic features included in the PTI and for the PTI itself. In Arm 2, five out of the six constituent component radiomic features of the PTI were significantly altered in the presence of unstable versus stable coronary lesions, while PTI outperformed all six individual radiomic features in discriminating unstable form stable coronary lesions (AUC: 0.76; 95% CI: 0.64-0.88). These findings suggest a close link between vascular inflammation associated with plaque rupture and perivascular region texture changes (which can now be detected by the radiomic signature of the invention, e.g. PTI) as a non-invasive way of monitoring the risk profile of a coronary lesion. AU: arbitrary units; SALGLE: small area low gray level emphasis; SRHGLE: short run high gray level emphasis; SZNU: size zone non-uniformity.

DETAILED DESCRIPTION

Figure 1A:
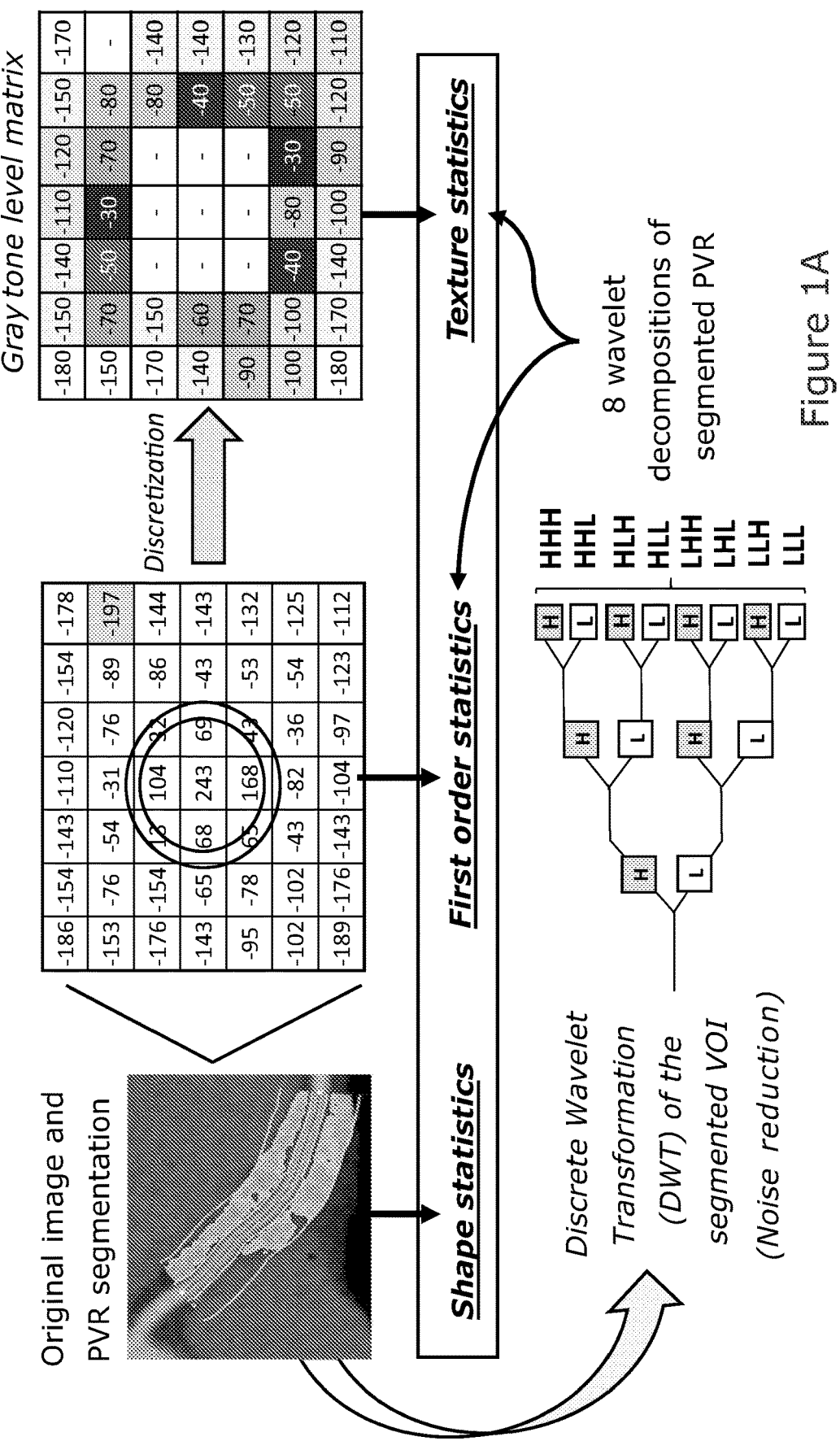
FIG. 1A illustrates the methodology of perivascular region phenotyping, volume segmentation, discretization, wavelet transformation and radiomic feature calculation.

The inventors have discovered that a perivascular region (PVR) radiomic signature (otherwise known as a "score" or "index") calculated on the basis of two or more radiomic features of the PVR adds incremental value beyond traditional risk factors and established CCTA risk classification tools in predicting future adverse cardiovascular events and evaluating cardiovascular health and risk, and further aids the detection of vascular inflammation in general, local plaque inflammation, and the presence of unstable coronary lesions. The PVR radiomic signature of the invention is therefore preferably calculated on the basis of two or more radiomic features of a PVR and provides a tool for characterising the PVR, for example perivascular tissue such as perivascular adipose tissue (PVAT), for the purpose of assessing cardiovascular or vascular health, predicting the risk of future adverse cardiovascular events in patients, identifying or diagnosing coronary artery disease or coronary heart disease, and identifying unstable coronary lesions or vascular inflammation, for example as caused by local plaques.

The PVR radiomic signature of the invention may be used on its own to characterise the PVR or to provide diagnostic or prognostic information, or it may be combined with existing models, such as the $FAI_{PVAT}$, the Duke Prognostic CAD index and/or other conventional models including demographics and risk factors, such as the presence of coronary calcium, high-risk plaque features, and/or EAT (epicardial adipose tissue) volume.

The invention exploits the fact that the coronary wall and the adjacent PVR, in particular tissues within the PVR such as adipose tissue, interact in a bidirectional manner. Vascular-induced phenotypic changes in coronary PVR can therefore function as a sensor of underlying disease, even in the absence of visible coronary lesions. In particular, the invention exploits the effect that this interaction has on the texture (e.g. the spatial non-uniformity or variability) of the PVR, and the radiomic signature of the invention may therefore be constructed to provide a measure of the texture of the PVR. The radiomic signature of the invention may therefore also be referred to as the perivascular texture index (PTI). However, the radiomics-based approach used to construct the signature of the invention is not specific to constructing a radiomic signature that measures texture and it is the prognostic value of the resulting signature that is of primary importance. It is therefore not strictly necessary for the radiomic signature to measure texture in order to be an effective prognostic or diagnostic tool.

The PVR refers to a region or volume adjacent to a blood vessel. The PVR may be a region or volume of perivascular tissue (PVT) or may comprise or consist of PVT. Perivascular tissue is tissue located adjacent to a blood vessel. Tissue is a complex biological structure, and may comprise cells (e.g. adipocytes, neurons, etc.) and extracellular structures and materials (such as water) which may occupy the intercellular spaces. In particular, the PVT may comprise or consist of perivascular adipose tissue (PVAT) and the PVR may therefore alternatively be referred to as a region or volume of PVAT.

The invention exploits a radiomic approach. Radiomics is a field of imaging in which a large amount of quantitative information is extracted from imaging data using data-characterization algorithms. The resulting features, referred to as radiomic features, range from simple volumetric, shape-related or first order statistics (such as mean or median attenuation), to second and higher order statistics that describe the texture of a segmented volume or region and the spatial relationship of voxels with similar or different attenuation values. Such features can identify imaging patterns of significant clinical value that cannot be recognized by the naked eye and have the potential to maximize the diagnostic yield of non-invasive PVR phenotyping.

The signature of the invention is derived and calculated on the basis of radiomic features, for example those extracted from medical imaging data. In particular, the medical imaging data from which the radiomic features are extracted correspond to a perivascular region (PVR), for example coronary PVR such as coronary perivascular adipose tissue (PVAT), and optionally also to the blood vessel itself and/or other tissue adjacent or surrounding the PVR. The medical imaging data typically comprise radiodensity (or attenuation) values, usually expressed in Hounsfield Units (HU), for a plurality of voxels of the relevant region, in this case the PVR, and optionally also the adjacent tissues.

The medical imaging data are preferably computed tomography (CT) data, such as coronary computed tomography angiography (CCTA), but other forms of medical imaging data (e.g. radiography data) that provide attenuation (or radiodensity) data for voxels of the imaged region may be used instead, such as three-dimensional computed laminography data. Typically, the medical imaging data used in the invention are three-dimensional imaging data. Throughout the following, where CCTA or another medical imaging technique is referred to, it should be understood that other suitable medical imaging techniques could alternatively be used.

The PVR may include only voxels having a radiodensity (or attenuation) falling within a given or predetermined range and/or located within a delineated region, for example within a given or predetermined radial distance from an outer vessel wall. The given radial distance is preferably a distance related to or dependent on one or more dimensions of the adjacent vessel, such as its diameter or radius. However, the radial distance may instead be a set or fixed value, such as about 5 mm. Alternatively, the PVR may be identified by manual contouring or delineation by a human operator, optionally also in combination with applying a radiodensity or attenuation mask so that only voxels having a radiodensity within a specified range and falling within the delineated region are included. For example, the operator may identify the PVR through an inspection of the data, for example the CT image. The PVR may include only voxels having a radiodensity in the Hounsfield Unit range of about −190 HU to about +30 HU. For example, the PVR may include only voxels having a radiodensity in the Hounsfield Unit range of about −190 HU to about −30 HU. This range of attenuation values generally corresponds to the radiodensity of perivascular adipose tissue (PVAT). However, other ranges could be used, for example about −30 to about +30 Hounsfield Units, which generally corresponds to the radiodensity of water. In particular, the PVR may be identified as all voxels having a radiodensity in the Hounsfield Unit range of about −190 HU to about −30 HU and located within a radial distance from the adjacent outer vessel wall approximately equal to the diameter of the adjacent vessel.

The radiomic features, and therefore also the radiomic signature, may be calculated for a particular blood vessel, for example a coronary vessel such as a coronary artery. The proximal and mid right coronary artery (RCA) (segments 1 and 2 according to the anatomical classification of the American Heart Association, for example as defined in Austen W G, Edwards J E, Frye R L, et al. A reporting system on patients evaluated for coronary artery disease. Report of the Ad Hoc Committee for Grading of Coronary Artery Disease, Council on Cardiovascular Surgery, American Heart Association. Circulation 1975; 51(4 Suppl): 5-40) is particularly suitable due to its straight course and absence of large branches. The PVR may therefore be located adjacent to a particular blood vessel.

The PVR may be segmented prior to calculating the radiomic features and the radiomic features may be calculated from the segmented data. The segmented volume or region corresponds to the PVR, and segmentation may remove data corresponding to voxels that are outside of the PVR. Segmentation may therefore be achieved by identifying the PVR, as described above, and then removing any voxels from the data that are identified as not being part of the PVR, for example those voxels corresponding to surrounding or adjacent tissue voxels. Segmentation may be performed by placing a three-dimensional sphere with a diameter equal to the diameter of the blood vessel plus twice the given distance from the outer vessel wall within which the PVR may be identified on consecutive slices following the centreline of the vessel. For example, if PVR is identified as being located within a radial distance from the outer vessel wall equal to the diameter of the adjacent vessel then the sphere will have a diameter equal to three times the diameter of the adjacent vessel. The segmented PVR may be extracted and used to calculate the radiomic features.

Calculation of the radiomic features from the medical imaging data may be performed using a computer program, or software. Various commercially available software packages exist for this purpose, such as 3D Slicer. The radiomic features may be shape-related statistics, first-order statistics, or texture statistics (e.g. second and higher order statistics). Shape-related and first-order radiomic features may be calculated using the raw radiodensity (HU) values of the PVR voxels. For calculation of texture features (e.g. Gray Level Co-occurrence Matrix [GLCM], Gray Level Dependence Matrix [GLDM], Gray Level Run-Length Matrix [GLRLM], Gray Level Size Zone Matrix [GLSZM], and Neighbouring Gray Tone Difference Matrix [NGTDM], see FIG. 1A and Tables R1-R7), PVR voxel radiodensity or attenuation values are preferably discretized into a plurality of bins, preferably into 16 bins, preferably of equal width (e.g. width of ten HU), to reduce noise while allowing a sufficient resolution to detect biologically significant spatial changes in PVR attenuation. Discretization into 16 bins is recommended as the optimal approach to increase the signal-to-noise ratio of images for radiomic analysis. However, discretization into more or fewer than 16 bins is also possible. To enforce symmetrical, rotationally-invariant results, some or all of the radiomic features, in particular the texture statistics (GLCM etc), may be calculated in all (orthogonal) directions and then averaged (e.g. using the mean or other average of the individually calculated values of the feature in each of the four directions).

Some or all of the radiomic features, in particular those relating to first order and texture-based statistics, may also be calculated for three-dimensional wavelet transformations of the original image data resulting in a number of additional sets of radiomic features (FIG. 1A), for example as described by Guo et al. (Guo X, Liu X, Wang H, et al. Enhanced CT images by the wavelet transform improving diagnostic accuracy of chest nodules. J Digit Imaging 2011; 24(1): 44-9). Wavelet transformation decomposes the data into high and low frequency components. At high frequency (shorter time intervals), the resulting wavelets can capture discontinuities, ruptures and singularities in the original data. At low frequency (longer time intervals), the wavelets characterize the coarse structure of the data to identify the long-term trends. Thus, the wavelet analysis allows extraction of hidden and significant temporal features of the original data, while improving the signal-to-noise ratio of imaging studies. The data may be decomposed by a discrete wavelet transform into a plurality (e.g. eight) wavelet decompositions by passing the data through a multi-level (e.g. three level) filter bank. At each level, the data are decomposed into high- and low-frequency components by high- and low-pass filters, respectively. Thus, if a three level filter bank is used, eight wavelet decompositions result, corresponding to HHH, HHL, HLH, HLL, LHH, LHL, LLH and LLL, where H refers to "high-pass", and L refers to "low-pass". Of course, more or fewer than eight levels could alternatively be used to decompose the data. Such decompositions may be performed using widely available software, such as the Slicer Radiomics software package which incorporates the Pyradiomics library. Where a radiomic feature is calculated on the basis of a wavelet decomposition or transformation of the data this is denoted by a suffix indicating which wavelet decomposition the radiomic feature has been calculated on the basis of (e.g. HHH for high-pass, high-pass, high-pass). So, for example, "Skewness LLL" denotes the radiomic feature "Skewness" as calculated on the basis of the LLL wavelet decomposition. Where no suffix is present, the radiomic feature is calculated on the basis of the original (or raw) data.

Deriving a Radiomic Signature

The invention provides a method for deriving a radiomic signature for characterising a PVR (for example a region of perivascular adipose tissue), for example for predicting cardiovascular risk. The radiomic signature is derived using medical imaging data for a plurality of individuals, and data including the occurrence of clinical endpoint events for each of the plurality of individuals within a subsequent period after the medical imaging data were collected. In particular, the clinical endpoint is preferably indicative of cardiovascular health or risk.

The method typically involves performing a case-control study of (human) patients with versus without adverse (clinical endpoint) events within a predetermined or subsequent time period, preferably five years, after the imaging data are collected, for example by clinically-indicated assessment by CCTA or other medical imaging technique. The individuals reaching the clinical endpoint are the cases (first group) and the individuals not reaching the clinical endpoint are the controls (second group).

The plurality of individuals (also referred to herein as patients) may be divided into two independent cohorts of patients undergoing (or who have undergone) medical imaging, specifically a training cohort and a validation cohort. Cases are identified based on the occurrence of clinical endpoint events within a specified or predetermined period following the collection of the medical imaging data, i.e. the subsequent period. The subsequent period is preferably at least about five years, preferably about five years, but could be longer or shorter. The clinical endpoint is preferably be the primary composite endpoint of major adverse cardiovascular events (MACE), which may be defined as the composite of all-cause mortality and non-fatal myocardial infarction (MI) within the specified period (preferably five years) following the collection of the medical imaging data, or the primary composite endpoint of cardiac-specific MACE (cMACE, i.e. cardiac mortality and non-fatal MI) within the specified period (preferably five years) following the collection of the medical imaging data.

Cardiac and non-cardiac mortality, as used herein, may be defined according to the recommendations of the ACC/AHA (Hicks K A, Tcheng J E, Bozkurt B, et al. 2014 ACC/AHA Key Data Elements and Definitions for Cardiovascular Endpoint Events in Clinical Trials: A Report of the American College of Cardiology/American Heart Association Task Force on Clinical Data Standards (Writing Committee to Develop Cardiovascular Endpoints Data Standards). J Am Coll Cardiol 2015; 66(4): 403-69). More specifically, cardiac mortality may be defined as any death due to proximate cardiac causes (e.g. myocardial infarction, low-output heart failure, fatal arrhythmia). Deaths fulfilling the criteria of sudden cardiac death may also be included in this group. Any death not covered by the previous definition, such as death caused by malignancy, accident, infection, sepsis, renal failure, suicide or other non-cardiac vascular causes such as stroke or pulmonary embolism may be classified as non-cardiac.

Controls are preferably identified as patients with event-free follow-up within the same specified period, for example for at least five years post-CCTA. 1:1 case-control matching is preferably performed to match cases with controls, for example using an automated algorithm. The cases and controls may be matched for clinical demographics (such as age, sex, obesity status), cohort and/or technical parameters related to imaging data acquisition (e.g. tube voltage and CT scanner used). Preferably, patients are also matched for other cardiovascular risk factors, including hypertension, dyslipidemia, diabetes mellitus and smoking.

Hypertension may be defined based on the presence of a documented diagnosis or treatment with an antihypertensive regimen, according to the relevant clinical guidelines (James P A, Oparil S, Carter B L, et al. 2014 evidence-based guideline for the management of high blood pressure in adults: report from the panel members appointed to the Eighth Joint National Committee (JNC 8). JAMA 2014; 311(5): 507-20). Similar criteria may be applied for the definition of hypercholesterolemia and diabetes mellitus (American Diabetes A. Diagnosis and classification of diabetes mellitus. Diabetes Care 2014; 37 Suppl 1: S81-90; Stone N J, Robinson J G, Lichtenstein A H, et al. 2013 ACC/AHA guideline on the treatment of blood cholesterol to reduce atherosclerotic cardiovascular risk in adults: a report of the American College of Cardiology/American Heart Association Task Force on Practice Guidelines. J Am Coll Cardiol 2014; 63(25 Pt B): 2889-934).

"Clustering" (or Collinear Elimination) Method

Figure 2A:
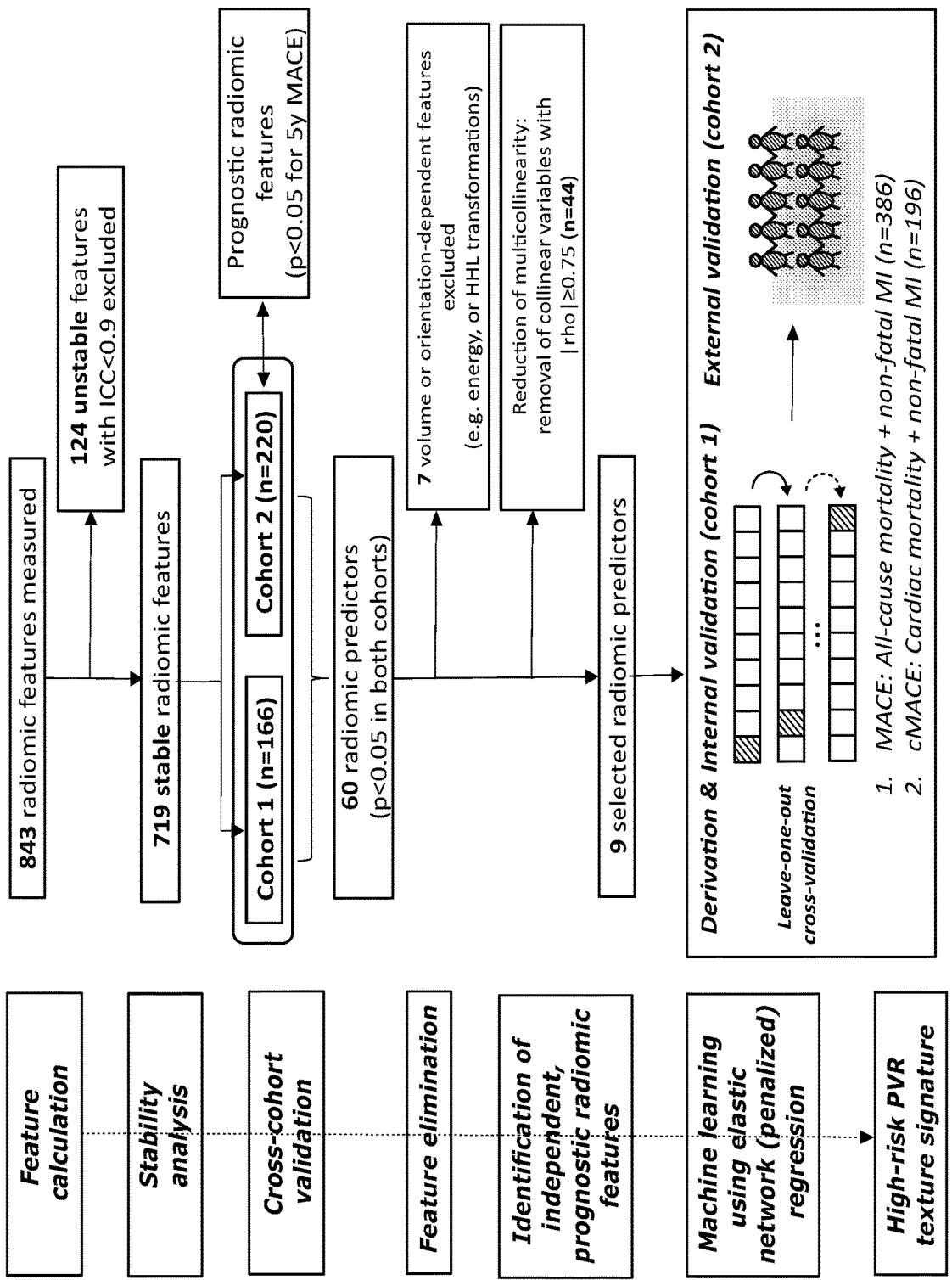
FIG. 2A summarises the multi-step approach used to build the signature as a flow diagram. First, out of a total of 843 calculated radiomic features, 124 were excluded following stability analysis (ICC<0.9). Next, sixty radiomic features that were significantly associated with MACE at the level of α=0.05 in both cohorts were selected. Among these, seven volume- and orientation-dependent features were excluded (e.g. Energy and non-HHH/LLL transformations), and collinearity was subsequently reduced by stepwise elimination of pairwise correlations at the level of |rho|≥0.75. Using the remaining nine radiomic features, a machine learning approach was applied in Cohort 1 using elastic network regression and leave-one-out internal cross-validation.

A stepwise approach may then be followed to develop a radiomic signature, as schematically illustrated in FIG. 2. First, a plurality of radiomic features are calculated from the medical imaging data for each of the plurality of individuals, for example as described above. The radiomic features may comprise a selection or all of the radiomic features as defined in Tables R1-R7, and each of the radiomic features may be calculated based on the raw image data and/or on one or more wavelet transformations of the image data (or wavelet decompositions), as described above. Preferably, each of the radiomic features is calculated for the raw image data and for the aforementioned eight three-dimensional wavelet decompositions of the image data.

Unstable features may be removed from the plurality of radiomic features. A z-score transformation may be applied to the features (i.e. expressing the values of the radiomic features in terms of the number of standard deviations from the mean) and the stability analysis performed on the basis of the z-scores. Unstable radiomic features are identified as those having an intraclass correlation coefficient (ICC) in repeat imaging data acquisitions (e.g. imaging scans) below a stability threshold. For example, the stability threshold may be at least about 0.9, for example about 0.9, so that all radiomic features having an ICC<0.9 are excluded (FIG. 3). However, other stability thresholds may be used instead, such as 0.85 or 0.95. The ICC may be calculated for a plurality of repeat scans, for example two to ten scans, in particular two or ten scans. In other words, a stability analysis may be performed on the PVR radiomic features and unstable radiomic features removed from the plurality of radiomic features. The stability analysis may be performed on the basis of the imaging data for the plurality of individuals, or may be performed using other data, for example reference data such as the RIDER dataset (The Reference Image Database to Evaluate Therapy Response).

Preferably, if the plurality of radiomic features includes any volume- and orientation-dependent radiomic features these are then excluded (i.e. removed from the plurality of radiomic features). Alternatively, any volume- and orientation-dependent features may be excluded from the start so that such a step is not necessary. In other words, the initial plurality of radiomic features may each be volume- and orientation-independent. Volume dependent features may include Energy and Total Energy (original and wavelet calculated), and orientation-dependent features may include those derived from the wavelet transformations HLL, HLH, LLH, HLL, LHL, LHH (i.e. all but LLL or HHH, or those wavelet transformations that are not exclusively high- or low-pass).

Radiomic features that are not significantly associated (e.g. correlated) with the clinical endpoint, for example 5-year MACE or cMACE, above a significance threshold may then be removed from the plurality of radiomic features. The association of each radiomic feature with the clinical endpoint may be calculated on the basis of a receiver operating characteristic curve (ROC) analysis, in particular an area under the curve calculation, based on the data for the plurality of individuals. The significance threshold is preferably $\alpha=0.05$ or lower, for example a may be in the range of from 0.001 to 0.05. The significance threshold is preferably about $\alpha=0.05$. However, the significance threshold may be about $\alpha=0.04$. Alternatively, the significance threshold may be about $\alpha=0.03$. Alternatively, the significance threshold may be about $\alpha=0.02$. Alternatively, the significance threshold may be about $\alpha=0.01$. Alternatively, the significance threshold may be about $\alpha=0.005$. Alternatively, the significance threshold may be about $\alpha=0.002$. Preferably, the radiomic features must be identified as being significantly associated with the clinical endpoint in both the training and validation cohorts in order to be retained, and any that are found to be not significantly associated with the clinical endpoint in one or both cohorts are removed in order to reduce positive findings due to cohort-specific variations. However, radiomic features that are found to be significantly associated with the clinical endpoint in only one of the cohorts, for example the training cohort, may instead be retained. Alternatively, the assessment of whether each of the radiomic features is significantly associated with the clinical endpoint may be performed on the basis of pooled data for both cohorts, i.e. for all of the plurality of individuals. In other words, the method may involve evaluating the significance of the radiomic features with the clinical endpoint and removing features that are found to be not significantly associated with the clinical endpoint from the plurality of features. The end result should be that any radiomic features that are not significantly associated with the clinical endpoint (as determined or calculated from the data, for example based on an analysis of the data) are removed from the plurality of radiomic features.

Collinearity of the retained radiomic features (i.e. those that are significantly associated with the clinical endpoint, otherwise known as significant radiomic features) may then be reduced or eliminated by removing pairwise correlations, i.e. by removing at least one of each pair of collinear radiomic features. The correlation between the radiomic features are generally calculated using the measured values of the radiomic features for the plurality of individuals. The removal of pairwise correlations may be performed in a stepwise manner. Collinear radiomic features may be identified as those that are correlated with each other to a degree at least equal to a given correlation threshold. The correlation threshold preferably applies to both positive and negative correlations, for example the correlation threshold may be expressed as a modulus. The pairwise correlations may be calculated using Spearman's rho coefficient and the correlation threshold may be at least about $|rho|=0.75$, for example about $|rho|=0.75$, so that all pairwise correlations at the level of $|rho|\geq 0.75$ are eliminated. As will be readily understood in the field, the correlation or collinearity is a measure of how closely two radiomic features vary together from one individual to the next and may be calculated on the basis of the measured radiomic feature values for the plurality of individuals.

For example, when a pair of collinear radiomic features is identified, one of the two features is preferably eliminated from the plurality of features. For example, the radiomic feature that is calculated from the data to be the less strongly associated with the clinical endpoint of the two may be eliminated and the radiomic feature that is most strongly associated with the clinical endpoint may be retained, but this is not necessary and either could be retained or eliminated. For example, the collinear elimination step may be performed in an unsupervised way without taking into account the clinical endpoint and the algorithm may eliminate the most redundant feature that contributes the least to the variation of the study population (e.g. the feature with the smaller variance as measured across the plurality of individuals). In one example, when a pair of collinear features is identified, the feature with the largest average (e.g. mean) absolute correlation (i.e. the average correlation value (or average modulus or square correlation value) with all other radiomic features) is removed. This may be performed in a stepwise manner until no collinear radiomic features remain.

The collinear elimination step may be performed using an algorithm or function, (for example, the function claret: findCorrelation, R package, see Kuhn, M. & Johnson, K. Applied Predictive Modelling. (Springer, 2013)). For example, the function or algorithm may construct a pairwise correlation matrix containing pairwise correlations between the radiomic features. The function may then search through the correlation matrix and return a vector of integers corresponding to columns to remove to reduce pairwise correlations. The radiomic features to which these columns correspond may then be removed from the plurality of radiomic features. In deciding which columns to remove, the algorithm may first identify pairwise correlations between radiomic features. When two collinear radiomic features are identified, the algorithm then identifies the column corresponding to the feature with the largest mean absolute correlation for removal.

Regardless of how the collinear elimination step is performed, the end result is preferably the production of a reduced plurality of radiomic features in which each of the features is correlated with each of the other remaining features to a degree less than the correlation threshold. In other words, the method may involve the step of removing radiomic features to eliminate collinearity between the radiomic features so that none of the remaining radiomic features is collinear with any of the other remaining radiomic features. This may involve the calculation of pairwise correlations between radiomic features and removing at least one of any identified pair of collinear features.

The radiomic signature may then be constructed based on at least two of the remaining radiomic features that survive whichever of the steps described above are performed (e.g. stability analysis, significance analysis and/or collinearity elimination). For example the radiomic signature may then be constructed based on at least two of the reduced plurality of non-collinear radiomic features that survive the collinear elimination step. The reduced plurality of features that survive the collinear elimination step are otherwise known as the "original features". However, since the eliminated radiomic features are each strongly correlated with at least one of the original features, a signature in which one or more of the original features is replaced by one of the features that is collinear with the replaced original feature will generally perform similarly to a signature calculated on the basis of only the original features. For example, it is possible to swap one of the original features for one of the features calculated as being collinear with that original feature and the signature should perform similarly. In fact, it is possible that replacing one or more (or even all) of the original features with alternative features that are collinear with the replaced original features could result in a signature having an enhanced prognostic value, and this has in fact been found to be the case in some instances (see, for example, Tables 8A and 8B). This is because although the original features are generally the most independently associated with the clinical endpoint, they are not necessarily the best-performing features when combined into a signature.

The process of constructing the radiomic signature may therefore involve the construction of "clusters" of radiomic features (each cluster comprising one of the original features) in which each of the radiomic features in each cluster is collinear with at least the "original" feature in that cluster (i.e. the feature of that cluster that survived the collinear elimination step, e.g. the feature in the cluster most strongly independently associated with the clinical endpoint). The construction of these clusters may be performed instead of the collinear elimination step. For example, instead of eliminating one of each pair of collinear features, the collinear features may be allocated to the same cluster. Alternatively, the pairwise elimination step may be performed as described above, and then, once the original features are identified, the eliminated features may be reintroduced by allocating them to the cluster of the original feature with which they are most strongly correlated or collinear with.

However, regardless of how the clusters are constructed, the end result should be that each radiomic feature is allocated to the same cluster as the original radiomic feature(s) that it is collinear with. If a radiomic feature is collinear with two "original" features, it is preferably allocated to the cluster of the original feature with which it is most collinear with, but it may be allocated to the clusters of all the original features with which it is collinear.

The clusters may also be expanded to include any of the original plurality of radiomic features that are collinear with the "original" radiomic feature of that cluster, regardless of whether the radiomic features are themselves independently significantly associated with the clinical endpoint. However, preferably any radiomic features included in the clusters are stable, as previously mentioned.

The "original" radiomic feature in each cluster therefore represents a "partner" radiomic features to each of the other radiomic features in that cluster, with each of the radiomic features in each cluster being collinear with its "partner" feature. The original radiomic feature may therefore be considered its own "partner" radiomic feature in this sense because it is perfectly collinear with itself.

An initial radiomic signature may then be constructed based on at least two (or all) of the reduced plurality of features (e.g. the "original" features). Alternatively, if clusters are constructed, the initial radiomic signature may be constructed from at least two radiomic features, each being selected from a different cluster. The construction of the radiomic signature involves refining or optimising the radiomic signature, in particular using data for the "training" cohort. This involves refining or optimising the contribution of each of each of the remaining radiomic features to the signature to improve the correlation or association of the signature with the clinical endpoint based on the data. For example, the signature may comprise a weighted sum of the values of each of the radiomic features included in the initial signature, and the weighing of each of the radiomic features may be progressively optimised or refined. The coefficients by which each of the radiomic features is multiplied are generally referred to as beta (β) coefficients, and it is these beta coefficients that may be optimised or refined.

Preferably all of the reduced plurality of features are included in the initial radiomic signature to be refined, e.g. one feature from each cluster, but this is not absolutely necessary. For example, the "top" or "original" feature from each cluster may be included (e.g. the feature most strongly independently associated with the clinical endpoint). Other radiomic features may also be included in the initial signature to be optimised, for example two or more radiomic features from any or all of the clusters may be included in the initial signature. However, in order to provide a signature more strongly associated with the clinical endpoint, and therefore of enhanced diagnostic and prognostic usefulness, it is preferable to include at least two radiomic features, each from a different cluster. This is because features from different clusters provide complementary information relating to the PVR. In particular, radiomic features from different clusters will be sensitive to different phenotypic characteristics of the PVR because they are collinear with different "original" or "partner" features. For example, the initial radiomic signature may comprise at least three radiomic features, each selected from a different cluster. Alternatively, the initial radiomic signature may comprise at least four radiomic features, each selected from a different cluster. Alternatively, the initial radiomic signature may comprise at least five radiomic features, each selected from a different cluster. Alternatively, the initial radiomic signature may comprise at least six radiomic features, each selected from a different cluster. Alternatively, the initial radiomic signature may comprise at least seven radiomic features, each selected from a different cluster. Alternatively, the initial radiomic signature may comprise at least eight radiomic features, each selected from a different cluster. Preferably, the initial radiomic signature may comprise one radiomic feature from each cluster.

Once the initial radiomic signature has been refined, the final radiomic signature may then be constructed based on all of the radiomic features included in the initial signature, or on a subset of those features. For example, the optimised or refined initial signature may be used as the final signature. Alternatively, the final radiomic signature may comprise only a subset of the radiomic features included in the initial signature. For example, only those parameters having a contribution to the refined initial signature above a certain threshold may be included in the final signature, such as those having an optimised weighting coefficient (e.g. beta parameter) above a certain (e.g. predetermined) threshold. In other words, those radiomic features that have optimised coefficients below a given threshold are removed from the final signature. For example, the top seven features (i.e. those with the largest contribution to the refined signature) may be included in the final signature.

If only a subset of the radiomic features is included in the final signature, one option is to re-optimise or refine the signature based only on the subset of features. For example, the coefficients or beta parameters may be re-optimised for the subset of radiomic features included in the final signature. Alternatively, the coefficients or beta parameters derived from the initial optimisation performed on the initial signature can be used in the final signature.

As mentioned above, the signature may include a weighted sum of the calculated values of a plurality of radiomic features. The signature may also include other terms, such as the addition or subtraction of a constant, or multiplication by a factor. However, typically the signature will be linearly related to the weighted sum of radiomic feature values in some way.

The radiomic signature may take the form of, or include the term (for example, the signature may be calculated on the basis of a function including the term):

$$A \pm \Sigma b_i rf_i$$

where A is a constant (which can be zero or non-zero), $b_i$ is the weighting coefficient (or beta patameter) for the radiomic feature i, and $rf_i$ is the measured value of the radiomic feature i. The beta parameter in the equation is preferably the unstandardized beta, which is the Z-score beta parameter multiplied by the standard deviation of the radiomic feature, where the standard deviation is preferably the standard deviation of the radiomic feature in the training or derivation cohort. The constant A is not necessary but may be included to ensure that all resulting values are either positive or negative, preferably positive. Preferably the "±" is a "−".

The initial and/or final radiomic signature may be constructed (i.e. optimised or refined) using a machine learning algorithm. For example, the machine learning algorithm may be used to refine or optimise the contribution of each of the radiomic features to the signature, for example by optimising the beta coefficients. The machine learning approach may use elastic net/lasso regression and may utilise leave-one-out internal cross-validation. Elastic net regression is a regularized regression method that linearly combines the L1 and L2 penalties of the lasso and ridge methods. L1 (least absolute shrinkage and selection operator "LASSO" penalty) penalizes the absolute values of the coefficients, shrinking irrelevant coefficients to zero and contributing to feature selection, whereas L2 ("ridge" penalty) penalizes the squares of the coefficients, therefore limiting the impact of collinearity and reducing overfitting. The optimal penalty coefficient (lambda, may be selected by cross-validation, while alpha is preferably set at α=1.

Preferably, the signature is refined using data for the training cohort, and is then validated externally using data for the training cohort.

"Non-Clustering" Method

The invention also provides another method for deriving a radiomic signature. In this method, a plurality of radiomic features are calculated from the medical imaging data for each of the plurality of individuals, as described above in relation to the "clustering" method.

The discriminatory value of all radiomic features (preferably all stable radiomic features) for the clinical endpoint, for example 5-year MACE, may then be evaluated, for example using receiver operating characteristic curve (ROC) analysis, in particular using an area under the curve calculation (calculating the C-statistics), and any radiomic features that are not significantly associated with the clinical endpoint are eliminated from the plurality of features. As for the clustering method described above, features are identified as being significantly associated with the clinical endpoint if they are associated with the clinical endpoint above a certain significance threshold. The significance threshold is preferably α=0.05 or lower, for example α=0.001 to 0.05. The significance threshold is preferably about α=0.05. However, the significance threshold may be about α=0.04. Alternatively, the significance threshold may be about α=0.03. Alternatively, the significance threshold may be about α=0.02. Alternatively, the significance threshold may be about α=0.01. Alternatively, the significance threshold may be about α=0.005. Alternatively, the significance threshold may be about α=0.002.

To correct for multiple comparisons and to decrease the false discovery rate (FDR), a Bonferroni correction may be applied to the significance threshold. The Bonferroni correction may be applied based on the number of principal components which account for a given amount of variability in the study sample based on a principal component analysis. For example, the given amount may be about 99.5%. In other words the m value used to correct the a value (by dividing a by m, i.e. a/m) is the number of principal components that account for the given amount of variability. For this reason, a principal component analysis of the radiomic features may be performed on the data for the plurality of individuals (preferably including both cohorts, if the individuals are divided into training and validation cohorts).

The radiomic signature may then be constructed based on at least two of the remaining radiomic features, i.e. those that are identified as being significantly associated with the clinical endpoint, as described above. The radiomic signature may be constructed and optimised in the same way as described for the clustering method above, but with the difference that there is no requirement to select radiomic features from different clusters.

For example, all of the radiomic features identified as significantly associated with the clinical endpoint may be included in the initial or final radiomic signature. Alternatively, only a subset of the radiomic features significantly associated with the clinical endpoint may be included in the initial or final signature, for example at least two. Alternatively, at least three of the radiomic features significantly associated with the clinical endpoint may be included in the initial or final signature. Alternatively, at least four of the radiomic features significantly associated with the clinical endpoint may be included in the initial or final signature. Alternatively, at least five of the radiomic features significantly associated with the clinical endpoint may be included in the initial or final signature. Alternatively, at least six of the radiomic features significantly associated with the clinical endpoint may be included in the initial or final signature. Alternatively, at least seven of the radiomic features significantly associated with the clinical endpoint may be included in the initial or final signature.

Again, the signature is preferably refined using data for the training cohort, and is then validated externally using data for the training cohort.

Elements of either the clustering or the non-clustering methods may be combined. For example, the clustering (or collinear elimination) method may involve the application of a Bonferroni correction.

For example, the plurality of radiomic features may be input into the machine learning algorithm without performing some (or any) of the preceding steps described above. Usually, however, at least the step of eliminating unstable radiomic features will be performed before the features are input into the machine learning algorithm.

In general, in the above-described methods (both clustering and non-clustering), bivariate associations between radiomic features may be assessed by the non-parametric Spearman's rho (ρ) coefficient, whereas intra-observer variability may be assessed in a given number of scans, for example at least two scans, for example ten scans, by means of the intraclass correlation coefficient (ICC).

The Radiomic Signature

The PVR radiomic signature of the invention is calculated on the basis of measured values of radiomic features obtained from medical imaging data. In particular, the PVR radiomic signature is preferably calculated on the basis of at least two radiomic features.

To improve the prognostic and diagnostic value of the signature, the signature is preferably calculated on the basis of at least two radiomic features selected from different "clusters" of collinear features, as described above. This reduces redundancy and improves the diversity of information included in the calculation of the signature because the features from different clusters relate to different textural aspects of the PVR.

Nine clusters have been identified using the "clustering" method, which correspond to the nine "original" or "partner" features of the reduced plurality of radiomic features that survived the collinear elimination process in the study described in the following "Examples" section. The members of the nine clusters are identified in Table 1.

Table 1 also identifies the "original feature", which is the feature in each cluster that survives the elimination of collinear features in the "clustering" method described above. The collinearity of the other features in each cluster with the original feature is expressed in terms of the Ipl coefficient (where p is the non-parametric Spearman's rho (ρ) coefficient).

To construct the clusters of Table 1, the 53 stable volume- and orientation-independent radiomic features that were associated with the clinical endpoint above the threshold value (p<0.05; where p is the probability value or asymptotic significance, i.e. α=0.05) in both the training and validation cohorts were clustered based on the strength of their correlation with the original features. If a radiomic feature was found to be collinear with two or more original features (|rho|≥0.75) then it was assigned to the cluster of the original feature with which it was most strongly associated. Interestingly, and perhaps surprisingly, $FAI_{PVAT}$ was not associated with any of the original features at a level of |rho|≥0.75 and is therefore not included in any of the clusters. This demonstrates that the present invention provides a separate and distinct prognostic and diagnostic tool as compared to calculating the $FAI_{PVAT}$ and is therefore complementary to the $FAI_{PVAT}$.

TABLE 1

Radiomic features of "standard" clusters selected from amongst the 53 identified features significantly associated with MACE

| Clusters and associated features | \|rho\| with original feature |
|---|---|
| Cluster #1: Original feature: Short Run High Gray Level Emphasis (SRHGLE) | |
| High Gray Level Emphasis | 0.975139 |
| High Gray Level Run Emphasis | 0.970598 |
| Cluster #2: Original feature: Skewness | |
| Skewness LLL | 0.962394 |
| Kurtosis | 0.871675 |
| $90^{th}$ Percentile | 0.851577 |
| Median LLL | 0.817939 |
| Kurtosis LLL | 0.809719 |
| Median | 0.789633 |
| Cluster #3: Original feature: Run Entropy | |
| Run Entropy LLL | 0.79152 |
| Mean LLL | 0.771156 |
| Cluster #4: Original feature: Small Area Low Gray Level Emphasis (SALGLE) | |
| Low Gray Level Zone Emphasis | 0.970552 |
| Gray Level Variance (GLSZM) | 0.763504 |
| Cluster #5: Original feature: Zone Entropy | |
| Gray Level Non Uniformity Normalized (GLRLM) | 0.891542 |
| Uniformity | 0.748464 |
| Cluster #6: Original feature: Zone Entropy HHH | |
| Cluster #7: Original feature: Strength | |
| Cluster #8: Original feature: Cluster Tendency LLL | |
| Cluster Tendency | 0.993906 |
| Mean Absolute Deviation LLL | 0.974087 |
| Gray Level Variance LLL (GLDM) | 0.972331 |
| Variance LLL | 0.972329 |
| Gray Level Variance LLL (GLRLM) | 0.972277 |
| Robust Mean Absolute Deviation LLL | 0.961639 |
| Gray Level Variance LLL (GLSZM) | 0.957704 |
| Interquartile Range LLL | 0.954142 |
| Sum Entropy LLL | 0.951601 |
| Gray Level Variance (GLRLM) | 0.951422 |
| Variance | 0.950236 |
| Gray Level Variance (GLDM) | 0.950177 |
| Mean Absolute Deviation | 0.945289 |
| Sum Entropy | 0.929493 |
| Robust Mean Absolute Deviation | 0.927285 |
| Interquartile Range | 0.920743 |
| Entropy LLL | 0.919022 |
| $10^{th}$ Percentile LLL | 0.911394 |
| $10^{th}$ Percentile | 0.898283 |
| Entropy | 0.860123 |
| Uniformity LLL | 0.852958 |
| Gray Level Non Uniformity Normalized LLL (GLDM) | 0.852183 |
| Gray Level Non Uniformity Normalized LLL (GLRLM) | 0.827855 |
| Root Mean Squared | 0.801892 |
| Gray Level Non Uniformity Normalized (GLDM) | 0.789831 |
| Root Mean Squared LLL | 0.783096 |
| Long Run Low Gray Level Emphasis | 0.775822 |
| Cluster #9: Original feature: Size Zone Non Uniformity LLL (SZNU LLL) | |
| Busyness | 0.879348 |
| Size Zone Non Uniformity | 0.856038 |

As mentioned previously, the clusters may be expanded to include stable members of the original plurality of radiomic features that are collinear with the "original" radiomic features of the clusters, regardless of whether the collinear radiomic features are themselves independently significantly associated with the clinical endpoint.

The members of the nine "expanded" clusters are presented in Table 2. These expanded clusters are equivalent to the original clusters presented in Table 1, but expanded to include any of the 719 stable radiomic features (ICC>0.9) that are also collinear with one of the original features from each cluster (|rho|≥0.75). Again, if a radiomic feature was found to be collinear with two or more original features (|rho|≥0.75) then it was assigned to the cluster of the original feature with which it was found to be most strongly associated.

TABLE 2

Radiomic features of "expanded" clusters selected
from amongst the 719 identified stable features

| Clusters and associated features | \|rho\| with original feature |
|---|---|
| Cluster #1: Original feature: Short Run High Gray Level Emphasis (SRHGLE) | |
| High Gray Level Emphasis | 0.975139 |
| High Gray Level Run Emphasis | 0.970598 |
| Autocorrelation | 0.935379 |
| Sum Average | 0.891625 |
| Joint Average | 0.891625 |
| High Gray Level Zone Emphasis | 0.757022 |
| Cluster #2: Original feature: Skewness | |
| Skewness LLL | 0.962394 |
| Kurtosis | 0.871675 |
| $90^{th}$ Percentile | 0.851577 |
| $90^{th}$ Percentile LLL | 0.838578 |
| Median LLL | 0.817939 |
| Kurtosis LLL | 0.809719 |
| Median | 0.789633 |
| Cluster #3: Original feature: Run Entropy | |
| Dependence Entropy LLL | 0.905264 |
| Dependence Entropy | 0.850414 |
| Zone Entropy LLL | 0.837804 |
| Run Entropy LLL | 0.79152 |
| Mean LLL | 0.771156 |
| Cluster #4: Original feature: Small Area Low Gray Level Emphasis (SALGLE) | |
| Low Gray Level Zone Emphasis | 0.970552 |
| Short Run Low Gray Level Emphasis | 0.886019 |
| Low Gray Level Run Emphasis | 0.877065 |
| Low Gray Level Emphasis | 0.869863 |
| Small Dependence Low Gray Level Emphasis | 0.865228 |
| Gray Level Variance LLL (GLSZM) | 0.830268 |
| Gray Level Variance (GLDM) | 0.806681 |
| Variance | 0.802258 |
| Gray Level Variance (GLDM) | 0.80188 |
| Difference Variance LLL | 0.800522 |
| Gray Level Variance LLL (GLRLM ) | 0.791822 |
| Variance LLL | 0.789145 |
| Gray Level Variance LLL (GLDM) | 0.789125 |
| Sum of Squares | 0.782797 |
| Contrast LLL | 0.775718 |
| Mean Absolute Deviation | 0.775093 |
| Interquartile Range | 0.771971 |
| Robust Mean Absolute Deviation | 0.770797 |
| Long Run Low Gray Level Emphasis | 0.766293 |
| Difference Variance | 0.766248 |
| Gray Level Variance (GLSZM) | 0.763504 |
| Inverse Difference Moment Normalized | 0.757157 |
| Mean Absolute Deviation LLL | 0.756059 |
| Sum of Squares LLL | 0.75198 |
| Contrast | 0.750381 |
| Cluster #5: Original feature: Zone Entropy | |
| Gray Level Non Uniformity Normalized (GLRLM) | 0.891542 |
| Gray Level Non Uniformity Normalized LLL (GLRLM) | 0.81717 |
| Sum Entropy | 0.776994 |
| Joint Energy | 0.775664 |
| Entropy | 0.774753 |
| Gray Level Non Uniformity Normalized (GLDM) | 0.767903 |
| Joint Energy LLL | 0.764334 |
| Gray Level Non Uniformity Normalized LLL (GLDM) | 0.762338 |
| Uniformity LLL | 0.759166 |
| Sum Entropy LLL | 0.754785 |
| Uniformity | 0.748464 |
| Cluster #6: Original feature: Zone Entropy HHH | |
| Size Zone Non Uniformity Normalized HHH | 0.814641 |
| Small Area Emphasis HHH | 0.789525 |
| Cluster #7: Original feature: Strength | |
| Coarseness HLL | 0.88454 |
| Coarseness | 0.870477 |
| Coarseness LHL | 0.86241 |
| Coarseness LLL | 0.859987 |
| Coarseness LLH | 0.855166 |

TABLE 2-continued

Radiomic features of "expanded" clusters selected from amongst the 719 identified stable features

| Clusters and associated features | \|rho\| with original feature |
|---|---|
| Coarseness HHH | 0.837053 |
| Coarseness HLH | 0.791609 |
| Coarseness HHL | 0.786734 |
| Coarseness LHH | 0.782421 |
| Cluster #8: Original feature: Cluster Tendency LLL | |
| Cluster Tendency | 0.993906 |
| SumSquares LLL | 0.98664 |
| Mean Absolute Deviation LLL | 0.983493 |
| Gray Level Variance LLL (GLDM) | 0.977069 |
| Variance LLL | 0.977064 |
| Gray Level Variance LLL (GLRLM) | 0.976888 |
| Gray Level Variance (GLRLM) | 0.971257 |
| Robust Mean Absolute Deviation LLL | 0.971198 |
| Gray Level Variance (GLDM) | 0.970257 |
| Variance | 0.970197 |
| Mean Absolute Deviation | 0.968679 |
| Cluster Prominence | 0.96516 |
| Sum Entropy LLL | 0.964505 |
| Interquartile Range LLL | 0.964208 |
| Gray Level Variance LLL (GLSZM) | 0.960755 |
| Sum of Squares | 0.960157 |
| Robust Mean Absolute Deviation | 0.951646 |
| Sum Entropy | 0.950703 |
| Interquartile Range | 0.945747 |
| Cluster Prominence LLL | 0.945739 |
| Entropy LLL | 0.943076 |
| $10^{th}$ Percentile LLL | 0.931818 |
| $10^{th}$ Percentile | 0.928162 |
| Cluster #9: Original feature: Size Zone Non Uniformity LLL (SZNU LLL) | |
| Dependence Non Uniformity HLL | 0.928379 |
| Gray Level Non Uniformity HLL (GLSZM) | 0.923214 |
| Gray Level Non Uniformity (GLSZM) | 0.909737 |
| Run Length Non Uniformity HHL | 0.908087 |
| Run Length Non Uniformity LHL | 0.900784 |
| Dependence Non Uniformity LHL | 0.887204 |
| Dependence Non Uniformity | 0.885575 |
| Run Length Non Uniformity HLH | 0.882877 |
| Busyness | 0.879348 |
| Run Length Non Uniformity LLH | 0.875944 |
| Dependence Non Uniformity LLH | 0.872262 |
| Dependence Non Uniformity LLL | 0.867809 |
| Size Zone Non Uniformity | 0.856038 |
| Energy HLL | 0.838125 |
| Run Length Non Uniformity LHH | 0.831353 |
| Size Zone Non Uniformity HLL | 0.809159 |
| Gray Level Non Uniformity LLH (GLSZM) | 0.803344 |
| Gray Level Non Uniformity LHL (GLSZM) | 0.801205 |
| Gray Level Non Uniformity LLL (GLSZM) | 0.791236 |
| Run Length Non Uniformity HLL | 0.786947 |
| Gray Level Non Uniformity HLH (GLSZM) | 0.778574 |
| Gray Level Non Uniformity HHL (GLSZM) | 0.778439 |
| Run Length Non Uniformity | 0.776126 |
| Run Length Non Uniformity HHH | 0.751445 |

The radiomic signature may be constructed from any of the radiomic features included in Table 1 or Table 2 (i.e. the standard or expanded clusters), provided the radiomic signature comprises at least two radiomic features each selected from different clusters. For example, the radiomic signature may comprise at least three radiomic features from different clusters. For example, the radiomic signature may comprise at least four radiomic features from different clusters. For example, the radiomic signature may comprise at least five radiomic features from different clusters. For example, the radiomic signature may comprise at least six radiomic features from different clusters. For example, the radiomic signature may comprise at least seven radiomic features from different clusters. For example, the radiomic signature may comprise at least eight radiomic features from different clusters. For example, the radiomic signature may comprise at least nine radiomic features from different clusters.

Each of the at least two (or more) radiomic features that are selected from different clusters may be selected to be correlated with the "original" feature of the clusters to which it belongs to a degree of at least $|rho|=0.8$. For example, each of the at least two radiomic features from different clusters may be correlated with the "original" feature of the clusters to which it belongs to a degree of at least $|rho|=0.85$. For example, each of the at least two radiomic features from different clusters may be correlated with the "original" feature of the clusters to which it belongs to a degree of at least $|rho|=0.9$. For example, each of the at least two radiomic features from different clusters may be correlated with the "original" feature of the clusters to which it belongs to a degree of at least |rho|=0.95.

In addition to the radiomic signature being calculated on the basis of at least two radiomic features from different cluster, it may also be calculated on the basis of additional radiomic features. For example, the radiomic signature may include more than one radiomic feature from any given cluster, or may include radiomic features not included in any of the clusters.

Alternatively, the radiomic signature may be calculated on the basis of at least two of the radiomic features that have been found to be independently associated with the clinical endpoint using the "non-clustering" approach. Thus, the radiomic signature may instead be calculated on the basis of at least two radiomic features selected from Table 3.

The radiomic signature may be calculated on the basis of at least two radiomic features from Table 3. For example, the radiomic signature may be calculated on the basis of at least three radiomic features from Table 3. For example, the radiomic signature may be calculated on the basis of at least four radiomic features from Table 3. For example, the radiomic signature may be calculated on the basis of at least five radiomic features from Table 3. For example, the radiomic signature may be calculated on the basis of at least six radiomic features from Table 3. For example, the radiomic signature may be calculated on the basis of at least seven radiomic features from Table 3.

The at least two (or more) radiomic features may be selected from those radiomic features in Table 3 that have a Bonferroni adjusted P value of <0.04. For example, those

TABLE 3

Radiomic features identified as significantly associated with MACE following the "non-clustering" approach

| Radiomic feature | Class | Transformation | Bonferroni adj. P value |
| --- | --- | --- | --- |
| Median_LLL | First order | LLL | 0.0002 |
| Mean_LLL | First order | LLL | 0.0003 |
| Median | First order | Original | 0.0003 |
| Root Mean Squared_LLL | First order | LLL | 0.0005 |
| Mean | First order | Original | 0.0007 |
| Kurtosis | First order | Original | 0.0008 |
| Root Mean Squared | First order | Original | 0.0014 |
| Run Entropy_LLL | GLRLM | LLL | 0.0015 |
| Uniformity | First order | Original | 0.0018 |
| $90^{th}$ Percentile | First order | Original | 0.0020 |
| Gray Level Non-Uniformity Normalized | GLRLM | Original | 0.0029 |
| Uniformity_LLL | First order | LLL | 0.0037 |
| Skewness | First order | Original | 0.0041 |
| Gray Level Non-Uniformity Normalized_LLL | GLRLM | LLL | 0.0041 |
| $10^{th}$ Percentile_LLL | First order | LLL | 0.0042 |
| Skewness_LLL | First order | LLL | 0.0045 |
| $10^{th}$ Percentile | First order | Original | 0.0060 |
| Entropy | First order | Original | 0.0070 |
| Interquartile Range_LLL | First order | LLL | 0.0081 |
| Robust Mean Absolute Deviation_LLL | First order | LLL | 0.0106 |
| Run Entropy | GLRLM | Original | 0.0119 |
| Interquartile Range | First order | Original | 0.0138 |
| Sum Entropy | GLCM | Original | 0.0139 |
| Gray Level Non-Uniformity Normalized_LLL | GLRLM | LLL | 0.0141 |
| Dependence Non-Uniformity_LHL | GLDM | LHL | 0.0152 |
| Kurtosis_LLL | First order | LLL | 0.0153 |
| Run Length Non-Uniformity_HHL | GLRLM | HHL | 0.0156 |
| Entropy_LLL | First order | LLL | 0.0161 |
| Robust Mean Absolute Deviation | First order | Original | 0.0201 |
| Sum Entropy_LLL | GLCM | LLL | 0.0223 |
| $90^{th}$ Percentile_LLL | First order | LLL | 0.0267 |
| Run Entropy_HHL | GLRLM | HHL | 0.0297 |
| Energy | First order | Original | 0.0312 |
| Energy_LLL | First order | LLL | 0.0328 |
| Strength | NGTDM | Original | 0.0337 |
| Autocorrelation | GLCM | Original | 0.0338 |
| Mean Absolute Deviation_LLL | First order | LLL | 0.0339 |
| High Gray Level Emphasis | GLDM | Original | 0.0344 |
| Joint Average | GLCM | Original | 0.0374 |
| Sum Average | GLCM | Original | 0.0374 |
| Short Run High Gray Level Emphasis | GLRLM | Original | 0.0383 |
| Energy_HHH | First order | HHH | 0.0384 |
| High Gray Level Run Emphasis | GLRLM | Original | 0.0420 |
| Run Entropy_HHH | GLRLM | HHH | 0.0441 |
| Energy_HHL | First order | HHL | 0.0483 |
| Mean Absolute Deviation | First order | Original | 0.0497 | with a Bonferroni adjusted P value of <0.03. For example, those with a Bonferroni adjusted P value of <0.02. For example, those with a Bonferroni adjusted P value of <0.01. For example, those with a Bonferroni adjusted P value of <0.005. For example, those with a Bonferroni adjusted P value of <0.002.

The signature may be constructed from the radiomic features listed in Table 3, but excluding Mean.

Again, in addition to the radiomic signature being calculated on the basis of at least two radiomic features selected from those presented in Table 3, it may also be calculated on the basis of additional radiomic features. For example, the radiomic signature may include radiomic features not included in Table 3.

Each of the radiomic signatures of the invention provides a straightforward means for characterising a PVR using medical imaging data. Because each of the radiomic signatures of the invention is based on a relatively small number of the total overall number of possible radiomic features that can be measured, the signature is simple to calculate and understand, and its physiological significance can be better appreciated by the clinician.

System

The methods of the invention may be performed on a system, such as a computer system. The invention therefore also provides a system that is configured or arranged to perform one or more of the methods of the invention. For example, the system may comprise a computer processor configured to perform one or more of the methods, or steps of the methods, of the invention. The system may also comprise a computer-readable memory loaded with executable instructions for performing the steps of any of the methods of the invention.

In particular, the methods of deriving the radiomic signature may be performed on such a system and such systems are therefore provided in accordance with the invention. For example, the system may be configured to receive, and optionally store, a dataset comprising the values of a plurality of radiomic features of a PVR obtained from medical imaging data for each of a plurality of individuals, and information regarding the occurrence during a subsequent period after collection of the medical imaging data of a clinical endpoint indicative of cardiovascular risk for each of the plurality of individuals. The system may be configured to use such a dataset to construct (e.g. derive and validate) a radiomic signature according to the methods of the invention.

Alternatively, the system may be configured to perform the method of characterising a PVR. In particular, the invention provides a system for characterising a PVR using medical imaging data of a subject. The system may be configured to calculate the value of a radiomic signature of a PVR using the medical imaging data. The radiomic signature may be calculated on the basis of measured values of at least two radiomic features of the PVR, and the measured values of the at least two radiomic features may be calculated from the medical imaging data.

The system may also be configured to calculate the radiomic features from medical imaging data, as described in more detail above. The system may therefore be configured to receive, and optionally store, medical imaging data, and to process the imaging data to calculate the radiomic features.

Definition of Radiomic Features

The definitions of the radiomic features referred to herein are generally well understood within the field of radiomics by reference to their name only. However, for ease or reference definitions of the features used herein are provided in Tables R1 to R7 below. The radiomic features in Tables R1 to R7 are defined in accordance with the radiomic features used by the Pyradiomics package (http://pyradiomics.readthedocs.io/en/latest/features.html, see van Griethuysen, J. J. M., Fedorov, A., Parmar, C., Hosny, A., Aucoin, N., Narayan, V., Beets-Tan, R. G. H., Fillon-Robin, J. C., Pieper, S., Aerts, H. J. W. L. (2017). Computational Radiomics System to Decode the Radiographic Phenotype. Cancer Research, 77(21), e104-e107. https://doi.org/10.1158/0008-5472.CAN-17-0339). Most features defined in Tables R1 to R7 are in compliance with feature definitions as described by the Imaging Biomarker Standardization Initiative (IBSI), which are available in Zwanenburg et al. (2016) (Zwanenburg, A., Leger, S., Vallières, M., and Lock, S. (2016). Image biomarker standardisation initiative—feature definitions. In eprint arXiv:1612.07003 [cs.CV]). Where a definition provided below does not comply exactly from the IBSI definition, it should be understood that either definition could be used in accordance with the invention. Ultimately, the precise mathematical definition of the radiomic features is not crucial because slight modifications do not affect the general properties of the image that are measured by each of the features. Thus, slight modifications to the features (for example, the addition or subtraction of constants or scaling) and alternative definitions of the features are intended to be encompassed by the present invention.

a. First Order Statistics

These statistics describe the central tendency, variability, uniformity, asymmetry, skewness and magnitude of the attenuation values in a given region of interest (ROI), disregarding the spatial relationship of the individual voxels. As such, they describe quantitative and qualitative features of the whole ROI (PVR). A total of 19 features were calculated for each one of the eight wavelet transformations and the original CT image, as follows:

Let:

X be the attenuation or radiodensity values (e.g. in HU) of a set of $N_p$ voxels included in the region of interest (ROI)

P(i) be the first order histogram with $N_g$ discrete intensity levels, where $N_g$ is the number of non-zero bins, equally spaced from 0 with a width.

p(i) be the normalized first order histogram and equal to $$\frac{P(i)}{N_p}$$

c is a value that shifts the intensities to prevent negative values in X. This ensures that voxels with the lowest gray values contribute the least to Energy, instead of voxels with gray level intensity closest to 0. Since the HU range of adipose tissue (AT) within the PVR (−190 to −30 HU) does not include zero, c may be set at c=0. Therefore, higher energy corresponds to less radiodense AT, and therefore a higher lipophilic content.

$\epsilon$ is an arbitrarily small positive number (e.g. $\approx 2.2 \times 10^{-16}$)

TABLE R1

First-order radiomic feature for PVR characterization

| Radiomic feature | Interpretation |
|---|---|
| $\text{Energy} = \sum_{i=1}^{N_p} (X(i) + c)^2$ | Energy is a measure of the magnitude of voxel values in an image. A larger value implies a greater sum of the squares of these values. |
| $\text{Total Energy} = V_{voxel} \sum_{i=1}^{N_p} (X(i) + c)^2$ | Total Energy is the value of Energy feature scaled by the volume of the voxel in cubic mm. |
| $\text{Entropy} = -\sum_{i=1}^{N_g} p(i) \log_2(p(i) + \epsilon)$ | Entropy specifies the uncertainty/randomness in the image values. It measures the average amount of information required to encode the image values |
| Minimum = min (X) | The minimum gray level intensity within the ROI. |
| The 10th percentile of X | The 10th percentile of X |
| The 90th percentile of X | The 90th percentile of X |
| Maximum = max (X) | The maximum gray level intensity within the ROI. |
| $\text{Mean} = \frac{1}{N_p} \sum_{i=1}^{N_p} X(i)$ | The average (mean) gray level intensity within the ROI. |
| Median | The median gray level intensity within the ROI. |
| Interquartile range = $P_{75} - P_{25}$ | Here $P_{25}$ and $P_{75}$ are the $25^{th}$ and $75^{th}$ percentile of the image array, respectively. |
| Range = max (X) − min (X) | The range of gray values in the ROI. |
| $MAD = \frac{1}{N_p} \sum_{i=1}^{N_p} |X(i) - \overline{X}|$ | Mean Absolute Deviation (MAD) is the mean distance of all intensity values from the Mean Value of the image array. |
| $rMAD = \frac{1}{N_{10-90}} \sum_{i=1}^{N_{10-90}} |X_{10-90}(i) - \overline{X}_{10-90}|$ | Robust Mean Absolute Deviation (rMAD) is the mean distance of all intensity values from the Mean Value calculated on the subset of image array with gray levels in between, or equal to the $10^{th}$ and $90^{th}$ percentile. |
| $\text{RMS} = \sqrt{\frac{1}{N_p} \sum_{i=1}^{N_p} (X(i) + c)^2}$ | Root Mean Squared (RMS) is the square-root of the mean of all the squared intensity values. It is another measure of the magnitude of the image values. This feature is volume-confounded, a larger value of c increases the effect of volume-confounding. |
| $\text{Skewness} = \frac{\mu_3}{\sigma^3} = \frac{\frac{1}{N_p} \sum_{i=1}^{N_p} (X(i) - \overline{X})^3}{\left(\sqrt{\frac{1}{N_p} \sum_{i=1}^{N_p} (X(i) - \overline{X})^2}\right)^3}$ | Skewness measures the asymmetry of the distribution of values about the Mean value. Depending on where the tail is elongated and the mass of the distribution is concentrated, this value can be positive or negative. (Where $\mu_3$ is the $3^{rd}$ central moment). |
| $\text{Kurtosis} = \frac{\mu_4}{\sigma^4} = \frac{\frac{1}{N_p} \sum_{i=1}^{N_p} (X(i) - \overline{X})^4}{\left(\frac{1}{N_p} \sum_{i=1}^{N_p} (X(i) - \overline{X})^2\right)^2}$ | Kurtosis is a measure of the 'peakedness' of the distribution of values in the image ROI. A higher kurtosis implies that the mass of the distribution is concentrated towards the tail(s) rather than towards the mean. A lower kurtosis implies the reverse: that the mass of the distribution is concentrated towards a spike near the Mean value. (Where $\mu_4$ is the 4th central moment). |
| $\text{Variance} = \frac{1}{N_p} \sum_{i=1}^{N_p} (X(i) - \overline{X})^2$ | Variance is the mean of the squared distances of each intensity value from the Mean value. This is a measure of the spread of the distribution about the mean. |

TABLE R1-continued

First-order radiomic feature for PVR characterization

| Radiomic feature | Interpretation |
|---|---|
| $\text{Uniformity} = \sum_{i=1}^{N_g} p(i)^2$ | Uniformity is a measure of the sum of the squares of each intensity value. This is a measure of the heterogeneity of the image array, where a greater uniformity implies a greater heterogeneity or a greater range of discrete intensity values. | b. Shape-Related Statistics

Shape-related statistics describe the size and shape of a given ROI, without taking into account the attenuation values of its voxels. Since they are independent of the gray level intensities, shape-related statistics were consistent across all wavelet transformation and the original CT image, and therefore were only calculated once. These were defined as follows:

Let:

V be the volume of the ROI in mm$^3$

A be the surface area of the ROI in mm$^2$

TABLE R2

Shape-related radiomic features for PVR characterization

| Radiomic feature | Interpretation |
|---|---|
| $\text{Volume} = \sum_{i=1}^{N} V_i$ | The volume of the ROI V is approximated by multiplying the number of voxels in the ROI by the volume of a single voxel $V_i$. |
| $\text{Surface Area} = \sum_{i=1}^{N} \frac{1}{2}|a_i b_i \times a_i c_i|$ | Surface Area is an approximation of the surface of the ROI in mm$^2$, calculated using a marching cubes algorithm, where N is the number of triangles forming the surface mesh of the volume (ROI), $a_i b_i$ and $a_i c_i$ are the edges of the i$^{th}$ triangle formed by points $a_i$, $b_i$ and $c_i$. |
| $\text{Surface to volume ratio} = \frac{A}{V}$ | Here, a lower value indicates a more compact (sphere-like) shape. This feature is not dimensionless, and is therefore (partly) dependent on the volume of the ROI. |
| $\text{Sphericity} = \frac{\sqrt[3]{36\pi V^2}}{A}$ | Sphericity is a measure of the roundness of the shape of the tumor region relative to a sphere. It is a dimensionless measure, independent of scale and orientation. The value range is $0 < \text{sphericity} \leq 1$, where a value of 1 indicates a perfect sphere (a sphere has the smallest possible surface area for a given volume, compared to other solids). |
| Volume Number | Total number of discrete volumes in the ROI. |
| Voxel Number | Total number of discrete voxels in the ROI. |
| Maximum 3D diameter | Maximum 3D diameter is defined as the largest pairwise Euclidean distance between surface voxels in the ROI (Feret Diameter). |
| Maximum 2D diameter (Slice) | Maximum 2D diameter (Slice) is defined as the largest pairwise Euclidean distance between ROI surface voxels in the row-column (generally the axial) plane. |
| Maximum 2D diameter (Column) | Maximum 2D diameter (Column) is defined as the largest pairwise Euclidean distance between ROI surface voxels in the row-slice (usually the coronal) plane. |
| Maximum 2D diameter (Row) | Maximum 2D diameter (Row) is defined as the largest pairwise Euclidean distance between tumor surface voxels in the column-slice (usually the sagittal) plane. |
| $\text{Major axis} = 4\sqrt{\lambda_{major}}$ | $\lambda_{major}$ is the length of the largest principal component axis |
| $\text{Minor axis} = 4\sqrt{\lambda_{minor}}$ | $\lambda_{minor}$ is the length of the second largest principal component axis |
| $\text{Least axis} = 4\sqrt{\lambda_{least}}$ | $\lambda_{least}$ is the length of the smallest principal component axis |

TABLE R2-continued

Shape-related radiomic features for PVR characterization

| Radiomic feature | Interpretation |
|---|---|
| Elongation = $\sqrt{\dfrac{\lambda_{minor}}{\lambda_{major}}}$ | Here, $\lambda_{major}$ and $\lambda_{minor}$ ate the lengths of the largest and second largest principal component axes. The values range between 1 (circle-like (non-elongated)) and 0 (single point or 1 dimensional line). |
| Flatness = $\sqrt{\dfrac{\lambda_{least}}{\lambda_{major}}}$ | Here, $\lambda_{major}$ and $\lambda_{minor}$ are the lengths of the largest and smallest principal component axes. The values range between 1 (non-flat, sphere-like) and 0 (a flat object). | c. Gray Level Co-Occurrence Matrix (GLCM)

In simple words, a GLCM describes the number of times a voxel of a given attenuation value i is located next to a voxel of j. A GLCM of size $N_g \times N_g$ describes the second-order joint probability function of an image region constrained by the mask and is defined as $P(i,j|\delta,\theta)$. The $(i,j)^{th}$ element of this matrix represents the number of times the combination of levels i and j occur in two pixels in the image, that are separated by a distance of $\delta$ pixels along angle $\theta$. The distance $\delta$ from the center voxel is defined as the distance according to the infinity norm. For $\delta=1$, this results in 2 neighbors for each of 13 angles in 3D (26-connectivity) and for $\delta=2$ a 98-connectivity (49 unique angles). In order to get rotationally invariant results, statistics are calculated in all directions and then averaged, to ensure a symmetrical GLCM.

Let:

$\epsilon$ be an arbitrarily small positive number (e.g. $\approx 22.2 \times 10^{-16}$)
$P(i,j)$ be the co-occurrence matrix for an arbitrary $\delta$ and $\theta$
$p(i,j)$ be the normalized co-occurrence matrix and equal to $$\frac{P(i,j)}{\Sigma P(i,j)}$$

Ng be the number of discrete intensity levels in the image
$p_x(i) = \Sigma_{j=1}^{N_g} P(i,j)$ be the marginal row probabilities
$p_y(j) = \Sigma_{i=1}^{N_g} P(i,j)$ be the marginal column probabilities
$\mu_x$ be the mean gray level intensity of $p_x$ and defined as $\mu_x = \Sigma_{i=1}^{N_g} p_x(i) i$
$\mu_y$ be the mean gray level intensity of $p_y$ and defined as $\mu_y = \Sigma_{j=1}^{N_g} p_y(j) j$
$\sigma_x$ be the standard deviation of $p_x$
$\sigma_y$ be the standard deviation of $p_y$ $$p_{x+y}(k) = \sum_{i=1}^{N_g}\sum_{j=1}^{N_g} p(i,j),$$

where $i+j=k$, and $k=2, 3, \ldots, 2N_g$ $$p_{x-y}(k) = \sum_{i=1}^{N_g}\sum_{j=1}^{N_g} p(i,j),$$

where $|i-j|=k$, and $k=0, 1, \ldots, N_g-1$
$HX = -\Sigma_{i=1}^{N_g} p_x(i) \log_2(p_x(i)+\epsilon)$ be the entropy of $p_x$
$HY = -\Sigma_{j=1}^{N_g} p_y(j) \log_2(p_y(j)+\epsilon)$ be the entropy of $p_y$ $$HXY1 = -\sum_{i=1}^{N_g}\sum_{j=1}^{N_g} p(i,j)\log_2(p_x(i)\,p_y(j) + \epsilon)$$

$$HXY2 = -\sum_{i=1}^{N_g}\sum_{j=1}^{N_g} p_x(i)p_y(j)\log_2(p_x(i)p_y(j) + \epsilon)$$

For distance weighting, GLCM matrices are weighted by weighting factor W and then summed and normalised. Weighting factor W is calculated for the distance between neighbouring voxels by $W = e^{-\|d\|^2}$, where d is the distance for the associated angle.

TABLE R3

Gray Level Co-occurrence Matrix (GLCM) statistics for PVR characterization

| Radiomic feature | Interpretation |
|---|---|
| Autocorrelation = $\sum_{i=1}^{N_g}\sum_{j=1}^{N_g} p(i,j) ij$ | Autocorrelation is a measure of the magnitude of the fineness and coarseness of texture. |
| Joint average = $\mu_x = \sum_{i=1}^{N_g}\sum_{j=1}^{N_g} p(i,j) i$ | Returns the mean gray level intensity of the i distribution. |
| Cluster prominence = $\sum_{i=1}^{N_g}\sum_{j=1}^{N_g} (i+j-\mu_x-\mu_y)^4 p(i,j)$ | Cluster Prominence is a measure of the skewness and asymmetry of the GLCM. A higher value implies more asymmetry around the mean while a lower value indicates a peak near the mean value and less variation around the mean. |
| Cluster tendency = $\sum_{i=1}^{N_g}\sum_{j=1}^{N_g} (i+j-\mu_x-\mu_y)^2 p(i,j)$ | Cluster Tendency is a measure of groupings of voxels with similar gray-level values. |
| Cluster shade = $\sum_{i=1}^{N_g}\sum_{j=1}^{N_g} (i+j-\mu_x-\mu_y)^3 p(i,j)$ | Cluster Shade is a measure of the skewness and uniformity of the GLCM. A higher cluster shade implies greater asymmetry about the mean. |

TABLE R3-continued

Gray Level Co-occurrence Matrix (GLCM) statistics for PVR characterization

| Radiomic feature | Interpretation |
| --- | --- |
| $\text{Contrast} = \sum_{i=1}^{N_g} \sum_{j=1}^{N_g} (i-j)^2 p(i,j)$ | Contrast is a measure of the local intensity variation, favoring values away from the diagonal (i = j). A larger value correlates with a greater disparity in intensity values among neighboring voxels. |
| $\text{Correlation} = \dfrac{\sum_{i=1}^{N_g} \sum_{j=1}^{N_g} p(i,j) ij - \mu_x \mu_y}{\sigma_x(i)\sigma_y(j)}$ | Correlation is a value between 0 (uncorrelated) and 1 (perfectly correlated) showing the linear dependency of gray level values to their respective voxels in the GLCM. |
| $\text{Difference average} = \sum_{k=0}^{N_g-1} k p_{x-y}(k)$ | Difference Average measures the relationship between occurrences of pairs with similar intensity values and occurrences of pairs with differing intensity values. |
| $\text{Difference entropy} = \sum_{k=0}^{N_g-1} p_{x-y}(k) \log_2(p_{x-y}(k) + \epsilon)$ | Difference Entropy is a measure of the randomness/variability in neighborhood intensity value differences. |
| $\text{Difference variance} = \sum_{k=0}^{N_g-1} (k - DA)^2 p_{x-y}(k)$ | Difference Variance is a measure of heterogeneity that places higher weights on differing intensity level pairs that deviate more from the mean. |
| $\text{Joint energy} = \sum_{i=1}^{N_g} \sum_{j=1}^{N_g} (p(i,j))^2$ | Joint energy is a measure of homogeneous patterns in the image. A greater joint energy implies that there are more instances of intensity value pairs in the image that neighbor each other at higher frequencies. (also known as Angular Second Moment). |
| $\text{Joint entropy} = -\sum_{i=1}^{N_g} \sum_{j=1}^{N_g} p(i,j) \log_2(p(i,j) + \epsilon)$ | Joint entropy is a measure of the randomness/variability in neighborhood intensity values. |
| $IMC\ 1 = \dfrac{HXY - HXY1}{\max\{HX, HY\}}$ | Informational measure of correlation 1 |
| $IMC\ 2 = \sqrt{1 - e^{-2(HXY2 - HXY)}}$ | Informational measure of correlation 2 |
| $IDM = \sum_{i=1}^{N_g} \sum_{j=1}^{N_g} \dfrac{p(i,j)}{1 + |i-j|^2}$ | IDM (inverse difference moment a.k.a Homogeneity 2) is a measure of the local homogeneity of an image. IDM weights are the inverse of the Contrast weights (decreasing exponentially from the diagonal i = j in the GLCM). |
| $IDMN = \sum_{i=1}^{N_g} \sum_{j=1}^{N_g} \dfrac{p(i,j)}{1 + \left(\dfrac{|i-j|^2}{N_g^2}\right)}$ | IDMN (inverse difference moment normalized) is a measure of the local homogeneity of an image. IDMN weights are the inverse of the Contrast weights (decreasing exponentially from the diagonal i = j in the GLCM). Unlike Homogeneity 2, IDMN normalizes the square of the difference between neighboring intensity values by dividing over the square of the total number of discrete intensity values. |
| $ID = \sum_{i=1}^{N_g} \sum_{j=1}^{N_g} \dfrac{p(i,j)}{1 + |i-j|}$ | ID (inverse difference a.k.a. Homogeneity 1) is another measure of the local homogeneity of an image. With more uniform gray levels, the denominator will remain low, resulting in a higher overall value. |
| $IDN = \sum_{i=1}^{N_g} \sum_{j=1}^{N_g} \dfrac{p(i,j)}{1 + \left(\dfrac{|i-j|}{N_g}\right)}$ | IDN (inverse difference normalized) is another measure of the local homogeneity of an image. Unlike Homogeneity 1, IDN normalizes the difference between the neighboring intensity values by dividing over the total number of discrete intensity values. |
| $\text{Inverse variance} = \sum_{i=1}^{N_g} \sum_{j=1}^{N_g} \dfrac{p(i,j)}{|i-j|^2},\ i \neq j$ | |
| $\text{Maximum probability} = \max(p(i,j))$ | Maximum Probability is occurrences of the most predominant pair of neighboring intensity values (also known as Joint maximum). |
| $\text{Sum average} = \sum_{k=2}^{2N_g} p_{x+y}(k) k$ | Sum Average measures the relationship between occurrences of pairs with lower intensity values and occurrences of pairs with higher intensity values. |
| $\text{Sum entropy} = \sum_{k=2}^{2N_g} p_{x+y}(k) \log_2(p_{x+y}(k) + \epsilon)$ | Sum Entropy is a sum of neighborhood intensity value differences. |
| $\text{Sum squares} = \sum_{i=1}^{N_g} \sum_{j=1}^{N_g} (i - \mu_x)^2 p(i,j)$ | Sum of Squares or Variance is a measure in the distribution of neighboring intensity level pairs about the mean intensity level in the GLCM. (Defined by IBSI as Joint Variance). | d. Gray Level Size Zone Matrix (GLSZM)

A Gray Level Size Zone (GLSZM) describes gray level zones in a ROI, which are defined as the number of connected voxels that share the same gray level intensity. A voxel is considered connected if the distance is 1 according to the infinity norm (26-connected region in a 3D, 8-connected region in 2D). In a gray level size zone matrix P(i,j) the (i,j)$^{th}$ element equals the number of zones with gray level i and size j appear in image. Contrary to GLCM and GLRLM, the GLSZM is rotation independent, with only one matrix calculated for all directions in the ROI.
Let:
$N_g$ be the number of discreet intensity values in the image
$N_s$ be the number of discreet zone sizes in the image
$N_p$ be the number of voxels in the image
$N_z$ be the number of zones in the ROI, which is equal to $\sum_{i=1}^{N_g} \sum_{j=1}^{N_s} P(i,j)$ and $1 \leq N_z \leq N_p$ P(i,j) be the size zone matrix
p(i,j) be the normalized size zone matrix, defined as $$p(i, j) = \frac{P(i, j)}{N_z}$$

$\epsilon$ is an arbitrarily small positive number (e.g. $\approx 2.2 \times 10^{-16}$).

TABLE R4

Gray Level Size Zone Matrix (GLSZM) statistics for PVR characterization

| Radiomic feature | Interpretation |
| --- | --- |
| $SAE = \dfrac{\sum_{i=1}^{N_g} \sum_{j=1}^{N_s} \frac{P(i, j)}{j^2}}{N_z}$ | SAE (small area emphasis) is a measure of the distribution of small size zones, with a greater value indicative of smaller size zones and more fine textures. |
| $LAE = \dfrac{\sum_{i=1}^{N_g} \sum_{j=1}^{N_s} P(i, j) j^2}{N_z}$ | LAE (large area emphasis) is a measure of the distribution of large area size zones, with a greater value indicative of larger size zones and more coarse textures. |
| $GLN = \dfrac{\sum_{i=1}^{N_g} \left(\sum_{j=1}^{N_s} P(i, j)\right)^2}{N_z}$ | GLN (gray level non-uniformity) measures the variability of gray-level intensity values in the image, with a lower value indicating more homogeneity in intensity values. |
| $GLNN = \dfrac{\sum_{i=1}^{N_g} \left(\sum_{j=1}^{N_s} P(i, j)\right)^2}{N_z^2}$ | GLNN (gray level non-uniformity normalized) measures the variability of gray-level intensity values in the image, with a lower value indicating a greater similarity in intensity values. This is the normalized version of the GLN formula. |
| $SZN = \dfrac{\sum_{j=1}^{N_s} \left(\sum_{i=1}^{N_g} P(i, j)\right)^2}{N_z}$ | SZN (size zone non-uniformity) measures the variability of size zone volumes in the image, with a lower value indicating more homogeneity in size zone volumes. |
| $SZNN = \dfrac{\sum_{j=1}^{N_s} \left(\sum_{i=1}^{N_g} P(i, j)\right)^2}{N_z^2}$ | SZNN (size zone non-uniformity normalized) measures the variability of size zone volumes throughout the image, with a lower value indicating more homogeneity among zone size volumes in the image. This is the normalized version of the SZN formula. |
| $\text{Zone Percentage} = \dfrac{N_z}{N_p}$ | ZP (Zone Percentage) measures the coarseness of the texture by taking the ratio of number of zones and number of voxels in the ROI. Values are in range $\dfrac{1}{N_p} \leq ZP \leq 1$, with higher values indicating a larger portion of the ROI consists of small zones (indicates a more fine texture). |
| $GLV = \sum_{i=1}^{N_g} \sum_{j=1}^{N_s} p(i, j)(i - \mu)^2$, where $\mu = \sum_{i=1}^{N_g} \sum_{j=1}^{N_s} p(i, j)i$ | Gray level variance (GLV) measures the variance in gray level intensities for the zones. |
| $ZV = \sum_{i=1}^{N_g} \sum_{j=1}^{N_s} p(i, j)(j - \mu)^2$, where $\mu = \sum_{i=1}^{N_g} \sum_{j=1}^{N_s} p(i, j)j$ | Zone Variance (ZV) measures the variance in zone size volumes for the zones. |
| $ZE = -\sum_{i=1}^{N_g} \sum_{j=1}^{N_s} p(i, j) \log_2(p(i, j) + \epsilon)$ | Zone Entropy (ZE) measures the uncertainty/randomness in the distribution of zone sizes and gray levels. A higher value indicates more heterogeneneity in the texture patterns. |

TABLE R4-continued

Gray Level Size Zone Matrix (GLSZM) statistics for PVR characterization

| Radiomic feature | Interpretation |
| --- | --- |
| $LGLZE = \dfrac{\sum_{i=1}^{N_g} \sum_{j=1}^{N_s} \dfrac{P(i,j)}{i^2}}{N_z}$ | LGLZE (low gray level zone emphasis) measures the distribution of lower gray-level size zones, with a higher value indicating a greater proportion of lower gray-level values and size zones in the image. |
| $HGLZE = \dfrac{\sum_{i=1}^{N_g} \sum_{j=1}^{N_s} P(i,j) i^2}{N_z}$ | HGLZE (high gray level zone emphasis) measures the distribution of the higher gray-level values, with a higher value indicating a greater proportion of higher gray-level values and size zones in the image. |
| $SALGLE = \dfrac{\sum_{i=1}^{N_g} \sum_{j=1}^{N_s} \dfrac{P(i,j)}{i^2 j^2}}{N_z}$ | SALGLE (small area low gray level emphasis) measures the proportion in the image of the joint distribution of smaller size zones with lower gray-level values. |
| $SAHGLE = \dfrac{\sum_{i=1}^{N_g} \sum_{j=1}^{N_s} \dfrac{P(i,j) i^2}{j^2}}{N_z}$ | SAHGLE (small area high gray level emphasis) measures the proportion in the image of the joint distribution of smaller size zones with higher gray-level values. |
| $LALGLE = \dfrac{\sum_{i=1}^{N_g} \sum_{j=1}^{N_s} \dfrac{P(i,j) j^2}{i^2}}{N_z}$ | LALGLE (low area low gray level emphasis) measures the proportion in the image of the joint distribution of larger size zones with lower gray-level values. |
| $LAHGLE = \dfrac{\sum_{i=1}^{N_g} \sum_{j=1}^{N_s} P(i,j) i^2 j^2}{N_z}$ | LAHGLE (low area high gray level emphasis) measures the proportion in the image of the joint distribution of larger size zones with higher gray-level values. | e. Gray Level Run Length Matrix (GLRLM)

A Gray Level Run Length Matrix (GLRLM) describes gray level runs, which are defined as the length in number of pixels, of consecutive pixels that have the same gray level value. In a gray level run length matrix $P(i,j|\theta)$, the $(i,j)^{th}$ element describes the number of runs with gray level i and length j occur in the image (ROI) along angle $\theta$.

Let:

$N_g$ be the number of discreet intensity values in the image $N_r$ be the number of discreet run lengths in the image $N_p$ be the number of voxels in the image $N_z(\theta)$ be the number of runs in the image along angle $\theta$, which is equal to $\sum_{i=1}^{N_g} \sum_{j=1}^{N_r} P(i,j|\theta)$ and $1 \le N_z(\theta) \le N_p$ $P(i,j|\theta)$ be the run length matrix for an arbitrary direction $\theta$ $p(i,j|\theta)$ be the normalized run length matrix, defined as $$p(i,j|\theta) = \dfrac{P(i,j|\theta)}{N_z(\theta)}$$

$\epsilon$ is an arbitrarily small positive number (e.g. $\approx 2.2 \times 10^{-16}$).

By default, the value of a feature is calculated on the GLRLM for each angle separately, after which the mean of these values is returned. If distance weighting is enabled, GLRLMs are weighted by the distance between neighbouring voxels and then summed and normalised. Features are then calculated on the resultant matrix. The distance between neighbouring voxels is calculated for each angle using the norm specified in 'weightingNorm'

TABLE R5

Gray Level Run Length Matrix (GLRLM) statistics for PVR characterization

| Radiomic feature | Interpretation |
| --- | --- |
| $SRE = \dfrac{\sum_{i=1}^{N_g} \sum_{j=1}^{N_r} \dfrac{P(i,j|\theta)}{j^2}}{N_z(\theta)}$ | SRE (Short Run Emphasis) is a measure of the distribution of short run lengths, with a greater value indicative of shorter run lengths and more fine textural textures. |
| $LRE = \dfrac{\sum_{i=1}^{N_g} \sum_{j=1}^{N_r} P(i,j|\theta) j^2}{N_z(\theta)}$ | LRE (Long Run Emphasis) is a measure of the distribution of long run lengths, with a greater value indicative of longer run lengths and more coarse structural textures. |
| $GLN = \dfrac{\sum_{i=1}^{N_g} \left( \sum_{j=1}^{N_r} P(i,j|\theta) \right)^2}{N_z(\theta)}$ | GLN (Gray Level Non-uniformity) measures the similarity of gray-level intensity values in the image, where a lower GLN value correlates with a greater similarity in intensity values. |

TABLE R5-continued

Gray Level Run Length Matrix (GLRLM) statistics for PVR characterization

| Radiomic feature | Interpretation |
|---|---|
| $GLNN = \dfrac{\sum_{i=1}^{N_g} \left(\sum_{j=1}^{N_r} P(i,j\|\theta)\right)^2}{N_z(\theta)^2}$ | GLNN (Gray Level Non-uniformity Normalized) measures the similarity of gray-level intensity values in the image, where a lower GLNN value correlates with a greater similarity in intensity values. This is the normalized version of the GLN formula. |
| $RLN = \dfrac{\sum_{j=1}^{N_r} \left(\sum_{i=1}^{N_g} P(i,j\|\theta)\right)^2}{N_z(\theta)}$ | RLN (Run Length Non-uniformity) measures the similarity of run lengths throughout the image, with a lower value indicating more homogeneity among run lengths in the image. |
| $RLNN = \dfrac{\sum_{j=1}^{N_r} \left(\sum_{i=1}^{N_g} P(i,j\|\theta)\right)^2}{N_z}$ | RLNN (Run Length Non-uniformity) measures the similarity of run lengths throughout the image, with a lower value indicating more homogeneity among run lengths in the image. This is the normalized version of the RLN formula. |
| $RP = \dfrac{N_z(\theta)}{N_p}$ | RP (Run Percentage) measures the coarseness of the texture by taking the ratio of number of runs and number of voxels in the ROI. Values are in range $\dfrac{1}{N_p} \leq RP \leq 1$, with higher values indicating a larger portion of the ROI consists of short runs (indicates a more fine texture). |
| $GLV = \sum_{i=1}^{N_g} \sum_{j=1}^{N_r} p(i,j\|\theta)(i-\mu)^2$, where $\mu = \sum_{i=1}^{N_g} \sum_{j=1}^{N_r} p(i,j\|\theta)i$ | GLV (Gray Level Variance) measures the variance in gray level intensity for the runs. |
| $RV = \sum_{i=1}^{N_g} \sum_{j=1}^{N_r} p(i,j\|\theta)(j-\mu)^2$, where $\mu = \sum_{i=1}^{N_g} \sum_{j=1}^{N_r} p(i,j\|\theta)j$ | RV (Run Variance) is a measure of the variance in runs for the run lengths. |
| $RE = -\sum_{i=1}^{N_g} \sum_{j=1}^{N_r} p(i,j\|\theta)\log_2(p(i,j\|\theta)+\epsilon)$ | RE (Run Entropy) measures the uncertainty/randomness in the distribution of run lengths and gray levels. A higher value indicates more heterogeneity in the texture patterns. |
| $LGLRE = \dfrac{\sum_{i=1}^{N_g} \sum_{j=1}^{N_r} \dfrac{P(i,j\|\theta)}{i^2}}{N_z(\theta)}$ | LGLRE (low gray level run emphasis) measures the distribution of low gray-level values, with a higher value indicating a greater concentration of low gray-level values in the image. |
| $HGLRE = \dfrac{\sum_{i=1}^{N_g} \sum_{j=1}^{N_r} P(i,j\|\theta)i^2}{N_z(\theta)}$ | HGLRE (high gray level run emphasis) measures the distribution of the higher gray-level values, with a higher value indicating a greater concentration of high gray-level values in the image. |
| $SRLGLE = \dfrac{\sum_{i=1}^{N_g} \sum_{j=1}^{N_r} \dfrac{P(i,j\|\theta)}{i^2 j^2}}{N_z(\theta)}$ | SRLGLE (short run low gray level emphasis) measures the joint distribution of shorter run lengths with lower gray-level values. |
| $SRHGLE = \dfrac{\sum_{i=1}^{N_g} \sum_{j=1}^{N_r} \dfrac{P(i,j\|\theta)i^2}{j^2}}{N_z(\theta)}$ | SRHGLE (short run high gray level emphasis) measures the joint distribution of shorter run lengths with higher gray-level values. |
| $LRLGLRE = \dfrac{\sum_{i=1}^{N_g} \sum_{j=1}^{N_r} \dfrac{P(i,j\|\theta)j^2}{i^2}}{N_z(\theta)}$ | LRLGLRE (long run low gray level emphasis) measures the joint distribution of long run lengths with lower gray-level values. |
| $LRHGLRE = \dfrac{\sum_{i=1}^{N_g} \sum_{j=1}^{N_r} P(i,j\|\theta)i^2 j^2}{N_z(\theta)}$ | LRHGLRE (long run high gray level run emphasis) measures the joint distribution of long run lengths with higher gray-level values. | f. Neighbouring Gray Tone Difference Matrix (NGTDM) Features

A Neighbouring Gray Tone Difference Matrix quantifies the difference between a gray value and the average gray value of its neighbours within distance $\delta$. The sum of absolute differences for gray level i is stored in the matrix. Let $X_{gl}$ be a set of segmented voxels and $x_{gl}(j_x,j_y,j_z) \in X_{gl}$ be the gray level of a voxel at position $(j_x,j_y,j_z)$, then the average gray level of the neigbourhood is:

$$\overline{A}_i = \overline{A}(j_x, j_y, j_z) = \frac{1}{W} \sum_{k_x=-\delta}^{\delta} \sum_{k_y=-\delta}^{\delta} \sum_{k_z=-\delta}^{\delta} x_{gl}(j_x+k_x, j_y+k_y, j_z+k_z),$$

where $(k_x, k_y, k_z) \neq (0,0,0)$ and $x_{gl}(j_x+k_x, j_y+k_y, j_z+k_z) \in x_{gl}$ Here, W is the number of voxels in the neighbourhood that are also in $X_{gl}$.

Let:

$n_i$ be the number of voxels in $X_{gl}$ with gray level i $N_{v,p}$ be the total number of voxels in $X_{gl}$ and equal to $\Sigma n_i$ (i.e. the number of voxels with a valid region; at least 1 neighbor). $N_{v,p} \leq N_p$, where $N_p$ is the total number of voxels in the ROI.

$p_i$ be the gray level probability and equal to $n_i/N_v$ $$s_i = \begin{cases} \Sigma^{n_i} |i - \overline{A}_i| & \text{for } n_i \neq 0 \\ 0 & \text{for } n_i = 0 \end{cases}$$

be the sum of absolute differences for gray level $i$ $N_g$ be the number of discreet gray levels $N_{g,p}$ be the number of gray levels where $p_i \neq 0$

TABLE R6

Neigbouring Gray Tone Difference Matrix (NGTDM) for PVR characterization

| Radiomic feature | Interpretation |
| --- | --- |
| $$\text{Coarseness} = \frac{1}{\sum_{i=1}^{N_g} p_i s_i}$$ | Coarseness is a measure of average difference between the center voxel and its neighbourhood and is an indication of the spatial rate of change. A higher value indicates a lower spatial change rate and a locally more uniform texture. |
| $$\text{Contrast} = \left( \frac{1}{N_{g,p}(N_{g,p}-1)} \sum_{i=1}^{N_g} \sum_{j=1}^{N_g} p_i p_j (i-j)^2 \right) \left( \frac{1}{N_{v,p}} \sum_{i=1}^{N_g} s_i \right),$$ where $p_i \neq 0$, $p_j \neq 0$ | Contrast is a measure of the spatial intensity change, but is also dependent on the overall gray level dynamic range. Contrast is high when both the dynamic range and the spatial change rate are high, i.e. an image with a large range of gray levels, with large changes between voxels and their neighbourhood. |
| $$\text{Busyness} = \frac{\sum_{i=1}^{N_g} p_i s_i}{\sum_{i=1}^{N_g} \sum_{j=1}^{N_g} |i p_i - j p_j|},$$ where $p_i \neq 0$, $p_j \neq 0$ | A measure of the change from a pixel to its neighbour. A high value for busyness indicates a 'busy' image, with rapid changes of intensity between pixels and its neighbourhood. |
| $$\text{Complexity} = \frac{1}{N_{v,p}} \sum_{i=1}^{N_g} \sum_{j=1}^{N_g} |i-j| \frac{p_i s_i + p_j s_j}{p_i + p_j},$$ where $p_i \neq 0$, $p_j \neq 0$ | An image is considered complex when there are many primitive components in the image, i.e. the image is non-uniform and there are many rapid changes in gray level intensity. |
| $$\text{Strength} = \frac{\sum_{i=1}^{N_g} \sum_{j=1}^{N_g} (p_i + p_j)(i-j)^2}{\sum_{i=1}^{N_g} s_i},$$ where $p_i \neq 0$, $p_j \neq 0$ | Strength is a measure of the primitives in an image. Its value is high when the primitives are easily defined and visible, i.e. an image with slow change in intensity but more large coarse differences in gray level intensities. | g. Gray Level Dependence Matrix (GLDM)

A Gray Level Dependence Matrix (GLDM) quantifies gray level dependencies in an image. A gray level dependency is defined as the number of connected voxels within distance $\delta$ that are dependent on the center voxel. A neighbouring voxel with gray level j is considered dependent on center voxel with gray level i if $|i-j|\leq\alpha$. In a gray level dependence matrix $P(i,j)$ the $(i,j)^{th}$ element describes the number of times a voxel with gray level i with j dependent voxels in its neighbourhood appears in image.

$N_g$ be the number of discreet intensity values in the image
$N_d$ be the number of discreet dependency sizes in the image
$N_z$ be the number of dependency zones in the image, which is equal to $\Sigma_{i=1}^{N_g} \Sigma_{j=1}^{N_d} P(i,j)$
$P(i,j)$ be the dependence matrix
$p(i,j)$ be the normalized dependence matrix, defined as $$p(i,j) = \frac{P(i,j)}{N_z}$$

TABLE R7

Gray Level Dependence Matrix (GLDM) statistics for PVR characterization

| Radiomic feature | Interpretation |
|---|---|
| $SDE = \dfrac{\sum_{i=1}^{N_g} \sum_{j=1}^{N_d} \frac{P(i,j)}{i^2}}{N_z}$ | SDE (Small Dependence Emphasis): A measure of the distribution of small dependencies, with a greater value indicative of smaller dependence and less homogeneous textures. |
| $LDE = \dfrac{\sum_{i=1}^{N_g} \sum_{j=1}^{N_d} P(i,j)j^2}{N_z}$ | LDE (Large Dependence Emphasis): A measure of the distribution of large dependencies, with a greater value indicative of larger dependence and more homogeneous textures. |
| $GLN = \dfrac{\sum_{i=1}^{N_g} \left(\sum_{j=1}^{N_d} P(i,j)\right)^2}{\sum_{i=1}^{N_g} \sum_{j=1}^{N_d} P(i,j)}$ | GLN (Gray Level Non-Uniformity): Measures the similarity of gray-level intensity values in the image, where a lower GLN value correlates with a greater similarity in intensity values. |
| $DN = \dfrac{\sum_{j=1}^{N_d} \left(\sum_{i=1}^{N_g} P(i,j)\right)^2}{N_z}$ | DN (Dependence Non-Uniformity): Measures the similarity of dependence throughout the image, with a lower value indicating more homogeneity among dependencies in the image. |
| $DNN = \dfrac{\sum_{j=1}^{N_d} \left(\sum_{i=1}^{N_g} P(i,j)\right)^2}{N_z^2}$ | DNN (Dependence Non-Uniformity Normalized): Measures the similarity of dependence throughout the image, with a lower value indicating more homogeneity among dependencies in the image. This is the normalized version of the DLN formula. |
| $GLV = \sum_{i=1}^{N_g} \sum_{j=1}^{N_d} p(i,j)(i-\mu)^2,$ where $\mu = \sum_{i=1}^{N_g} \sum_{j=1}^{N_d} ip(i,j)$ | GLV (Gray Level Variance): Measures the variance in grey level in the image. |
| $DV = \sum_{i=1}^{N_g} \sum_{j=1}^{N_d} p(i,j)(j-\mu)^2,$ where $\mu = \sum_{i=1}^{N_g} \sum_{j=1}^{N_d} jp(i,j)$ | DV (Dependence Variance): Measures the variance in dependence size in the image. |
| $DE = -\sum_{i=1}^{N_g} \sum_{j=1}^{N_d} p(i,j)\log_2(p(i,j)+\epsilon)$ | DE (Dependence Entropy): Measures the entropy in dependence size in the image. |
| $LGLE = \dfrac{\sum_{i=1}^{N_g} \sum_{j=1}^{N_d} \frac{P(i,j)}{i^2}}{N_z}$ | LGLE (Low Gray Level Emphasis): Measures the distribution of low gray-level values, with a higher value indicating a greater concentration of low gray-level values in the image. |

TABLE R7-continued

Gray Level Dependence Matrix (GLDM) statistics for PVR characterization

| Radiomic feature | Interpretation |
|---|---|
| $HGLE = \dfrac{\sum_{i=1}^{N_g} \sum_{j=1}^{N_d} P(i,j)i^2}{N_z}$ | HGLE (High Gray Level Emphasis): Measures the distribution of the higher gray-level values, with a higher value indicating a greater concentration of high gray-level values in the image. |
| $SDLGLE = \dfrac{\sum_{i=1}^{N_g} \sum_{j=1}^{N_d} \dfrac{P(i,j)}{i^2 j^2}}{N_z}$ | SDLGLE (Small Dependence Low Gray Level Emphasis): Measures the joint distribution of small dependence with lower gray-level values. |
| $SDHGLE = \dfrac{\sum_{i=1}^{N_g} \sum_{j=1}^{N_d} \dfrac{P(i,j)i^2}{j^2}}{N_z}$ | SDHGLE (Small Dependence High Gray Level Emphasis): Measures the joint distribution of small dependence with higher gray-level values. |
| $LDLGLE = \dfrac{\sum_{i=1}^{N_g} \sum_{j=1}^{N_d} \dfrac{P(i,j)j^2}{i^2}}{N_z}$ | LDLGLE (Large Dependence Low Gray Level Emphasis): Measures the joint distribution of large dependence with lower gray-level values. |
| $LDHGLE = \dfrac{\sum_{i=1}^{N_g} \sum_{j=1}^{N_d} P(i,j)i^2 j^2}{N_z}$ | LDHGLE (Large Dependence High Gray Level Emphasis): Measures the joint distribution of large dependence with higher gray-level values. |

Examples

Methods

A two-arm study, designed to explore the diagnostic and prognostic value of coronary PVR radiomic phenotyping on CCTA was performed. The study flowchart and baseline characteristics of the study Arms 1 and 2 are presented in FIG. 1 and Tables 4A, 4B and 5. The research protocol was approved by all local institutional review boards.

Arm 1

This was a case-control study of patients with versus without adverse events within five years after clinically-indicated assessment by CCTA. Eligible cases were retrieved from the prospectively collected data of two independent cohorts of patients undergoing clinically-indicated CCTA. Out of a total of 4239 individual scans reviewed (2246 in Cohort 1 and 1993 in Cohort 2), 3912 were of adequate quality and were included in further analysis. Cases were identified based on the primary composite endpoint of major adverse cardiovascular events (MACE), defined as the composite of all-cause mortality and non-fatal myocardial infarction (MI) within five years following the CCTA, whereas controls were identified as patients with event-free follow-up for at least five years post-CCTA. Following review of the quality of the scans and retrieval of relevant demographics, 1:1 matching was performed using an automated algorithm for age, sex, obesity status, cohort and technical parameters related to CCTA acquisition (tube voltage and CT scanner used). Where possible patients were also matched for other cardiovascular risk factors, including hypertension, dyslipidemia, diabetes mellitus and smoking. A subgroup of patients with a cardiac-specific MACE (cMACE; cardiac mortality and non-fatal MI) and their matched controls were also examined separately to increase the sensitivity for cardiac-specific high-risk PVR features.

TABLE 4A

Study Arm 1 demographics

| | | Cohort 1 | | |
|---|---|---|---|---|
| | | MACE | no MACE | P value |
| Total n | | 83 | 83 | — |
| Age (years) | | 58.1 ± 14.9 | 56.7 ± 14.6 | 0.52 |
| Sex (% male) | | 60.2 | 60.2 | 1.00 |
| Hypertension (%)* | | 63.9 | 74.7 | 0.13 |
| Dyslipidemia (%)* | | 57.8 | 60.2 | 0.75 |
| Diabetes mellitus (%)* | | 25.3 | 14.5 | 0.08 |
| Smoking (%)* | | 37/83 | 26/83 | 0.08 |
| Body Mass Index (BMI, kg/m$^2$) | | 29.7 ± 8.8 | 30.1 ± 6.5 | 0.75 |
| EAT volume (cm3) | | 104.1 ± 60.7 | 101.9 ± 53.5 | 0.80 |
| Medications (%)* | Antiplatelets | 30.1 | 55.4 | 0.34 |
| | Statins | 56.7 | 41.0 | 0.044 |
| | ACEi/ARBs | 38.6 | 39.8 | 0.98 |
| | Beta-blockers | 24.1 | 15.7 | 0.17 |

TABLE 4A-continued

Study Arm 1 demographics

|  |  | Cohort 1 | | |
|---|---|---|---|---|
|  |  | MACE | no MACE | P value |
| Tube voltage (%) | 120 kVp | 75.9 | 75.9 | 1.00 |
|  | 100 kVp | 24.1 | 24.1 |  |
| Scanner (%) | 2 × 192 Somatom Force | 13.3 | 13.3 |  |
|  | 1 × 256 Brilliance iCT | 86.7 | 86.7 | 1.00 |
|  | 2 × 128 Definition Flash | — | — |  |
|  | 2 × 64 Definition Flash | — | — |  |
|  | 1 × 64 Sensation 64 | — | — |  |
| CAD (%)* | None to mild (0-24%) | 59.4 | 38.6 | 0.01 |
|  | Mild (25-49%) | 42.2 | 44.6 |  |
|  | Moderate (50-69%) | 24.1 | 15.7 |  |
|  | Severe (≥70%) | 10.8 | 1.2 |  |
| High-risk plaque present |  | 38.6 | 39.8 | 0.87 |
| Coronary calcification (>0) |  | 65.1 | 41.0 | 0.002 |

Values presented as percentages (%) or mean ± standard deviation.
*presented as valid percentages.
ACEi: angiotensin-converting enzyme inhibitors; ARBs: angiotensin II-receptor blockers; CAD: coronary artery disease; (c)MACE: (cardiac-specific) major adverse cardiovascular events.

TABLE 4B

Study Arm 1 demographics

|  |  | Cohort 2 | | |
|---|---|---|---|---|
|  |  | MACE | no MACE | P value |
| Total n |  | 110 | 110 | — |
| Age (years) |  | 68.0 ± 11.5 | 66.2 ± 11.1 | 0.25 |
| Sex (% male) |  | 58.2 | 58.2 | 1.00 |
| Hypertension (%)* |  | 74.0 | 73.3 | 0.54 |
| Dyslipidemia (%)* |  | 47.3 | 52.0 | 0.49 |
| Diabetes mellitus (%)* |  | 15.8 | 13.9 | 0.41 |
| Smoking (%)* |  | 8.3 | 7.9 | 0.54 |
| Body Mass Index (BMI, kg/m$^2$) |  | 28.1 ± 5.9 | 28.6 ± 5.6 | 0.66 |
| EAT volume (cm$^3$) |  | 106.7 ± 57.7 | 107.6 ± 54.0 | 0.91 |
| Medications (%)* | Antiplatelets | 42.4 | 0.5 | 0.54 |
|  | Statins | 40.7 | 46.8 | 0.60 |
|  | ACEi/ARBs | 56.4 | 56.4 | 0.89 |
|  | Beta-blockers | 50.5 | 45.7 | 0.69 |
| Tube voltage (%) | 120 kVp | 81.8 | 81.8 | 1.00 |
|  | 100 kVp | 18.2 | 18.2 |  |
| Scanner (%) | 2 × 192 Somatom Force | — | — |  |
|  | 1 × 256 Brilliance iCT | — | — | 1.00 |
|  | 2 × 128 Definition Flash | 0.009 | 0.009 |  |
|  | 2 × 64 Definition Flash | 0.891 | 0.891 |  |
|  | 1 × 64 Sensation 64 | 0.1 | 0.1 |  |
| CAD (%)* | None to mild (0-24%) | 21.8 | 27.3 | 0.021 |
|  | Mild (25-49%) | 33.6 | 46.4 |  |
|  | Moderate (50-69%) | 14.5 | 12.7 |  |
|  | Severe (≥70%) | 0.3 | 13.6 |  |
| High-risk plaque present |  | 21.8 | 0.2 | 0.74 |
| Coronary calcification (>0) |  | 74.5 | 63.6 | 0.08 |

Values presented as percentages (%) or mean ± standard deviation.
*presented as valid percentages.
ACEi: angiotensin-converting enzyme inhibitors; ARBs: angiotensin II-receptor blockers; CAD: coronary artery disease; (c)MACE: (cardiac-specific) major adverse cardiovascular events.

Arm 2

This was a prospective study (Ox-IMPACT study, ethical approval provided by South-Central, Oxford C Research Ethics Committee; REC Reference 17/SC/0058) that recruited 22 patients (n=22 unstable lesions) presenting with acute myocardial infarction, who were invited to undergo a series of CCTA scans within 96 hours of admission and six months later. A control group of 32 patients with known stable CAD (n=39 stable lesions) and previous percutaneous coronary intervention (PCI) at least three months before the CCTA scan were also included in this arm. Radiomic phenotypic of a coronary PVR was performed around both stable and unstable lesions to identify a radiomic signature of a PVR linked to plaque instability and inflammation.

TABLE 5

Study Arm 2 demographics

|  | Arm 3 (ACS) | Arm 3 (Stable CAD) |
| --- | --- | --- |
| Total subjects included | 22 | 32 |
| Age (years) | 53.5 [34-79] | 59 [26-76] |
| Male gender (%) | 81.3 | 81.0 |
| Hypertension | 31.3 | 71.4 |
| Dyslipidemia | 31.3 | 76.2 |
| Diabetes Mellitus | 25 | 23.8 |
| Active/past smoking | 25/43.8 | 9.1/27.3 |
| Antiplatelets (aspirin/clopidogrel) | 100 | 95.5 |
| Statins | 93.8 | 85.7 |
| ACEi or ARBs | 87.5 | 63.6 |
| Beta-blockers | 93.8 | 76.2 |

Values presented as median [range] or percentages (%); ACEi: Angiotensin-Converting Enzyme inhibitors; ACS: acute coronary syndromes; ARBs: Angiotensin-II-Receptor Blockers; CAD: coronary artery disease.

Radiomic Features Included in Study

A total of 843 PVR radiomic features were measured, as summarized in Table 6.

TABLE 6

Breakdown of PVR radiomic features

|  | Original | Wavelet transformations (n = 8) | All |
| --- | --- | --- | --- |
| First order | 18 | 144 | 162 |
| Shape-related | 15 | — | 15 |
| GLCM | 23 | 184 | 207 |
| GLDM | 14 | 112 | 126 |
| GLRLM | 16 | 128 | 144 |
| GLSZM | 16 | 128 | 144 |
| NGTDM | 5 | 40 | 45 |
| Total | 107 | 736 | 843 |

GLCM: gray level co-occurrence matrix; GLDM: gray level dependence matrix; GLRLM: gray level run length matrix; GLSZM: gray level size zone matrix; NGTDM: neighbouring gray tone dependence matrix; PVR: perivascular region.

Data Collection, Definitions and Outcome Assessment

In Arm 1, outcome data were assembled through search of medical records, and querying of local/national databases by local investigators not involved in subsequent image/data analysis. Appropriate institutional review board approval was obtained with waiver of individual informed consent. Clinical data and demographics were recorded prospectively in the electronic medical records at the time of initial clinical encounter and manually extracted for the current study. Hypertension was defined based on the presence of a documented diagnosis or treatment with an antihypertensive regimen, according to the relevant clinical guidelines (James P A, Oparil S, Carter B L, et al. 2014 evidence-based guideline for the management of high blood pressure in adults: report from the panel members appointed to the Eighth Joint National Committee (JNC 8). JAMA 2014; 311(5): 507-20). Similar criteria were applied for the definition of hypercholesterolemia and diabetes mellitus (American Diabetes A. Diagnosis and classification of diabetes mellitus. Diabetes Care 2014; 37 Suppl 1: S81-90; Stone N J, Robinson J G, Lichtenstein A H, et al. 2013 ACC/AHA guideline on the treatment of blood cholesterol to reduce atherosclerotic cardiovascular risk in adults: a report of the American College of Cardiology/American Heart Association Task Force on Practice Guidelines. J Am Coll Cardiol 2014; 63(25 Pt B): 2889-934). Ascertainment of the exact cause of death was performed locally by study investigators at each site, through chart review, inspection of the death certificate and/or telephone follow-up and/or verification with a family member. Cardiac and non-cardiac mortality were defined according to the recommendations of the ACC/AHA and the Academic Research Consortium, as described previously. More specifically, cardiac mortality was defined as any death due to proximate cardiac causes (e.g. myocardial infarction, low-output heart failure, fatal arrhythmia). Deaths fulfilling the criteria of sudden cardiac death were also included in this group. Any death not covered by the previous definition, such as death caused by malignancy, accident, infection, sepsis, renal failure, suicide or other non-cardiac vascular causes such as stroke or pulmonary embolism was classified as non-cardiac. Deaths where information on the cause of death could not be collected with certainty were classified as "deaths of unknown cause" at the discretion of the local site investigators. Non-fatal myocardial infarction events during follow-up (ST-segment elevation or non-ST segment elevation) were also retrieved through search of electronic health records.

Coronary CT Angiography (CCTA) Acquisition Protocol

Cohort 1:

The majority of the CCTA scans (87.1%) were performed on a 256-slice Brilliance iCT scanner (Philips Medical Systems, Best, The Netherlands), with the remainder using a 2×128-slice Definition Flash scanner (Siemens Healthcare, Erlangen, Germany) (10.8%) and a 2×192-slice Somatom Force CT scanner (Siemens Healthcare, Forchheim, Germany) (2.1%). In patients with heart rate >60 beats/minute, 5 mg of intravenous metoprolol (with incremental 5 mg doses up to a maximum dose of 30 mg) or intravenous diltiazem (5 mg increments up to 20 mg maximum), if the heart rate remained above 60 beats per minute once the patient was positioned on the CT table. Patients also received 0.3 mg of nitroglycerin sublingually immediately before CCTA and iodinated contrast (Omnipaque 350, General Electric, Milwaukee, USA) was administered at flow rate of 5-6 ml/s.

Cohort 2:

CCTA scans were performed on a 2×64-slice scanner (Definition Flash, Siemens Healthcare, Forchheim, Germany) (79.2%), with the remainder using either a 64-slice (Siemens Sensation 64, Siemens Healthcare, Forchheim, Germany) (18.1%) or 2×128-slice scanner (2.7%) (Somatom Definition Flash, Siemens Healthcare, Forchheim, Germany). Oral medication with 100 mg atenolol was administered one hour before CT if heart rate was >60 beats per minute with additional 5 mg doses of metoprolol intravenously up to a maximum dose of 30 mg, if the heart rate remained above 60 beats per minute once the patient was positioned on the CT table. Patients also received 0.8 mg of nitroglycerine sublingually immediately before CCTA and iodinated contrast (Omnipaque 350, Schering AG, Berlin, Germany) was administered at flow rate of 5-6 ml/s.

Study Arm 2:

Participants in Study Arm 2 underwent CCTA using a 64-slice scanner (General Electric, LightSpeed Ultra, General Electric, Milwaukee, WI, USA). Heart rate was optimised using intravenous injection of beta-blockers and sublingual glyceryl-trinitrate (800 µg) was also administered to achieve maximum coronary vasodilatation. CCTA was performed following intravenous injection of 95 ml of iodine based contrast medium (Niopam 370, BRACCO UK Ltd) at a flow rate of 6 mL/sec (tube energy of 120 kVp, axial slice thickness of 0.625 mm, rotation time of 0.35 sec, detector coverage of 40 mm). Prospective image acquisition was used by ECG-gating at 75% of cardiac cycle (with 100 msec padding for optimal imaging of the right coronary artery if required).

CCTA Scan Processing and Analysis

All images were first anonymized locally, and subsequently transferred to a core lab (Academic Cardiovascular CT Unit, University of Oxford, United Kingdom) for analysis on a dedicated workstation (Aquarius Workstation® V.4.4.13, TeraRecon Inc., Foster City, CA, USA) by investigators blinded to population demographics and outcomes. All scans were initially reviewed based on their quality and presence of artefacts precluding a reliable qualitative and quantitative evaluation. Low-quality scans were reviewed by at least two independent investigators before being excluded from subsequent analysis. Mild, moderate and severe coronary stenoses were defined as luminal stenosis 25-49%, 50-69% and ≥70%, respectively (as previously described in Cury R C, Abbara S, Achenbach S, et al. CAD-RADS™ Coronary Artery Disease—Reporting and Data System. An expert consensus document of the Society of Cardiovascular Computed Tomography (SCCT), the American College of Radiology (ACR) and the North American Society for Cardiovascular Imaging (NASCI). Endorsed by the American College of Cardiology. J Cardiovasc Comput Tomogr 2016; 10(4): 269-81). Obstructive coronary artery disease (CAD) was defined as the presence of ≥1 coronary lesion causing luminal stenosis ≥50%, whereas CAD extent was assessed by the Duke Prognostic CAD Index (for example, as defined in Min J K, Shaw L J, Devereux R B, et al. Prognostic value of multidetector coronary computed tomographic angiography for prediction of all-cause mortality. J Am Coll Cardiol 2007; 50(12): 1161-70). High-risk plaque features were defined as the presence of at least one of the following features on CCTA: a) spotty-calcification, b) low-attenuation plaque, c) positive remodeling and d) napkin-ring sign (as previously described in Puchner S B, Liu T, Mayrhofer T, et al. High-risk plaque detected on coronary CT angiography predicts acute coronary syndromes independent of significant stenosis in acute chest pain: results from the ROMICAT-II trial. J Am Coll Cardiol 2014; 64(7): 684-92). Epicardial (visceral) obesity was assessed by measuring the total epicardial adipose tissue (EAT) volume in a semi-automated manner by tracking the contour of the pericardium from the level of the pulmonary artery bifurcation to the apex of the heart at the most caudal end. $FAI_{PVAT}$ was defined as previously described in Antonopoulos A S, Sanna F, Sabharwal N, et al. Detecting human coronary inflammation by imaging perivascular fat. Sci Transl Med 2017; 9(398).

Coronary PVR Radiomic Feature Extraction

Calculation of radiomic features in a coronary PVR was performed in all selected CCTA scans using 3D Slicer (v.4.9.0-2017-12-18 r26813, available at http://www.slicer.org). To avoid issues of collinearity between different coronary vessels, analysis in Arm 1 was restricted to the proximal and mid right coronary artery (RCA) (segments 1 and 2 according to the anatomical classification of the American Heart Association). The coronary PVR was defined as all voxels in the Hounsfield Unit range of −190 to −30 Hounsfield Units (HU) located within a radial distance from the outer vessel wall equal to the diameter of the adjacent vessel. Segmentation of the coronary PVR was performed by placing a three-dimensional sphere with a diameter equal to three times the diameter of the coronary vessel on consecutive slices following the centerline of the vessel. The segmented PVR was subsequently extracted and used to calculate radiomic features, using the SlicerRadiomics extension of 3D Slicer, which incorporates the Pyradiomics library into 3D Slicer. Shape-related and first-order radiomic features were calculated using the raw HU values of the segmented PVR. For calculation of texture features (Gray Level Co-occurrence Matrix [GLCM], Gray Level Dependence Matrix [GLDM], Gray Level Run-Length Matrix [GLRLM], Gray Level Size Zone Matrix [GLSZM], and Neighbouring Gray Tone Difference Matrix [NGTDM], FIG. 1A, Tables R1-R7), the PVR voxels were discretized into 16 bins of equal width (width of ten HU), to reduce noise while allowing a sufficient resolution to detect biologically significant spatial changes in the PVR attenuation. To enforce symmetrical, rotationally-invariant results, texture statistics (GLCM etc) were calculated in all four directions and then averaged (for example, as previously described in Kolossvary M, Kellermayer M, Merkely B, Maurovich-Horvat P. Cardiac Computed Tomography Radiomics: A Comprehensive Review on Radiomic Techniques. Journal of thoracic imaging 2018; 33(1): 26-34).

Wavelet Transformation:

First order and texture-based statistics were also calculated for three-dimensional wavelet transformations of the original image resulting in eight additional sets of radiomic features (FIG. 1A).

Statistical Analysis

In Arm 1, the case-control matching was performed using an automated algorithm, provided by the ccmatch command in Stata. In the final study population, clinical demographics are presented as mean±standard deviation for continuous variables, and percentages for categorical variables. Continuous variables between two groups were compared by Student's t-test, whereas categorical variables are compared using Pearson's Chi-square test.

Principal Components and Unsupervised Clustering:

In both Study Arms, all 843 calculated PVR radiomic features were included in principal component analysis to identify principal components that describe most of the phenotypic variation in the study population. The three first components in Arm 1 (PC1, PC2, PC3) and Arm 2 (PC1', PC2' and PC3') were then used to perform hierarchical clustering of the observations (using the Ward method and the Minkowski distance). The frequency of MACE (Arm 1) and unstable plaques (Arm 2) between distinct clusters were compared by a Chi-square test.

Feature Selection and Improved Discrimination:

First, the discriminatory value of all radiomic features for 5-year MACE was tested in receiver operating characteristic curve (ROC) analysis. This analysis was performed on pooled data for both Cohorts. To correct for multiple comparisons, a genome-wide association study (GWAS)-based approach that has been previously used in the field of radiomic image analysis was followed, by applying a Bonferroni correction for the number of principal components which account for 99.5% of the variability in our study sample (see, for example, Kolossvary M, Karady J, Szilveszter B, et al. Radiomic Features Are Superior to Conventional Quantitative Computed Tomographic Metrics to Identify Coronary Plaques With Napkin-Ring Sign. Circ Cardiovasc Imaging 2017; 10(12) and Johnson R C, Nelson G W, Troyer J L, et al. Accounting for multiple comparisons in a genome-wide association study (GWAS). BMC Genomics 2010; 11: 724). Bivariate associations between radiomic features were assessed by the non-parametric Spearman's rho (ρ) coefficient, whereas intra-observer variability was assessed in ten scans by means of the intraclass correlation coefficient (ICC).

In order to build a radiomic signature of high-risk PVR, a multi-step approach was followed. Z-score transformation was applied to all features and unstable radiomic features with low ICC in repeated analysis (<0.9) were excluded. To minimize false positive findings driven by cohort-specific variations, we then selected features that were significantly associated with MACE in both cohorts (at the level of $\alpha=0.05$). Next, collinearity was reduced by stepwise removal of pairwise comparisons using an appropriate function of the caret package on R. A machine learning approach was then applied in Cohort 1 using elastic network regression and leave-one-out internal cross-validation. The optimal penalty coefficient (lambda, λ) was selected by cross-validation, while alpha was set at $\alpha=1$. The best performing models for both MACE and cMACE were then validated externally in Cohort 2, and discrimination was assessed by calculating the Area Under the Curve (AUC). The top variables of the best performing model were then combined in a unified score/signature by multiplying each one by the respective unadjusted beta coefficients of the model and calculating the total sum. The unified signature was then added in a logistic regression model consisting of the following four blocks: i) age, sex, hypertension, dyslipidemia, smoking and diabetes mellitus (Model 1); ii) Model 1+CT-derived measurements, including Duke Prognostic CAD index, presence of high-risk plaque features, EAT volume and presence of coronary calcium (Model 2); iii) Model 2+$FAI_{PVAT}$ (Model 3); and iv) Model 3+PVR texture signature. The prognostic value of the nested models for MACE and cMACE was compared by means of their respective C-statistics (Area Under the Curve, AUC). The interaction between $FAI_{PVAT}$ and the PVR texture signature is presented graphically using two-way contour plots derived from the previous multiple logistic regression models. Comparison of the selected radiomic features between unstable and stable plaques in Arm 2 was performed using the non-parametric Mann-Whitney test. Statistical analyses were performed in the R environment (packages: caret, hclust), as well as Stata v14.0 (Stata Corp Inc., College Station, Texas). All tests were two-sided and a was set at 0.05, unless specified otherwise.

Results

Study Population Demographics

Out of 3912 individual scans that were reviewed in Arm 1, a total of 386 scans were included in the study, corresponding to 193 patients with 5-year MACE and 193 matched controls. A selected subgroup of 98 patients with cardiac-specific mace (cMACE) and their matched controls were also identified and analysed in a subgroup-type analysis. The population demographics and baseline characteristics of the study Arm 1 population are summarized in Tables 4A and 4B. Cases and controls were not significantly different in terms of their baseline demographics, however, as expected, cases (MACE or cMACE) were more likely to have coronary artery disease (CAD), as assessed by the degree of coronary stenosis and the Duke Prognostic CAD index) compared to their controls. Study Arm 2 included 22 patients with unstable lesions, and 32 age- and sex-matched controls with a total of 39 stable lesions (Table 5).

PVR Radiomics: Component Analysis and Association with Adverse Events

Figure 4:
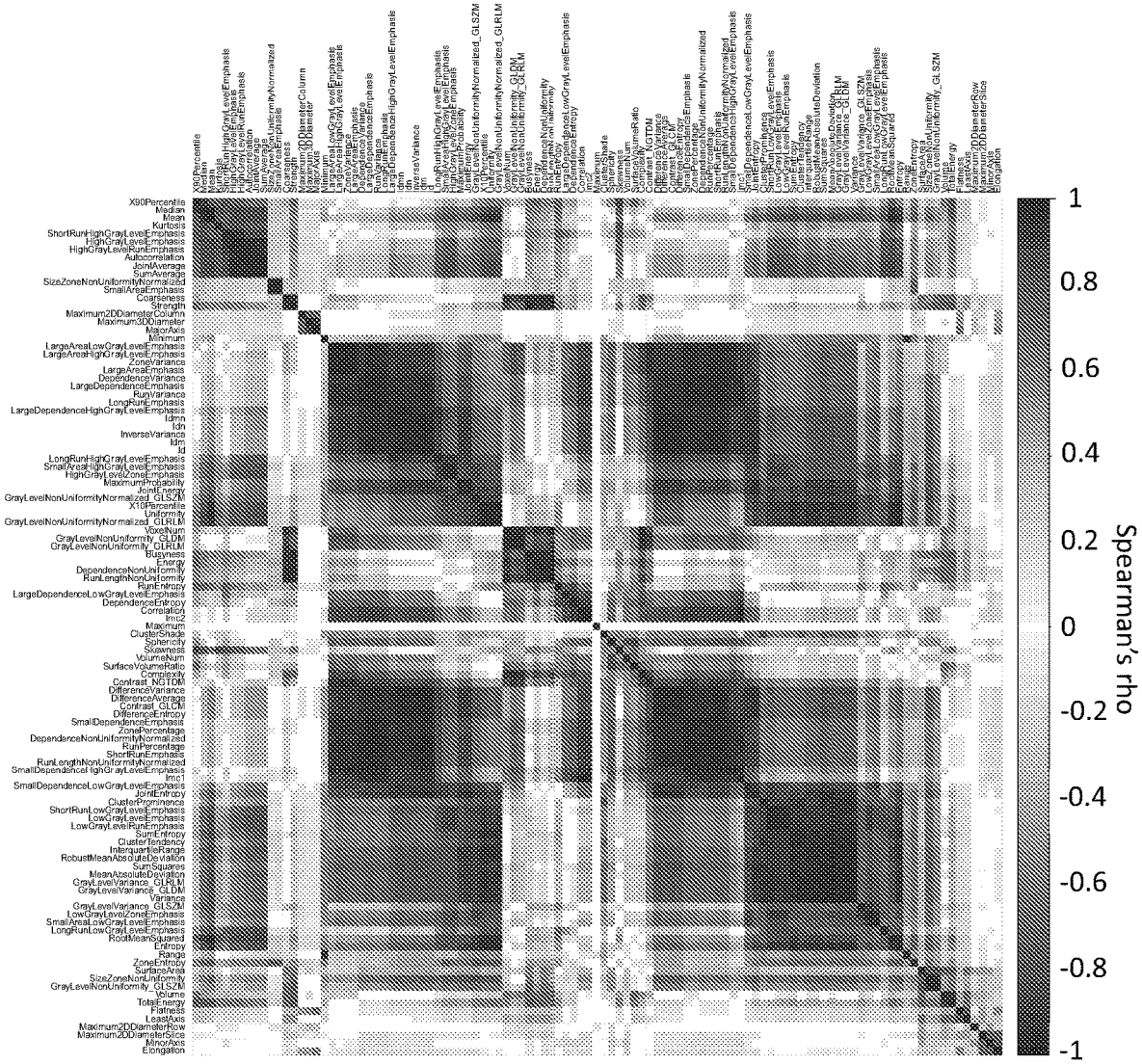
FIG. 4 shows a correlation plot of original radiomic features. The correlation plot of the 107 coronary perivascular region radiomic features shown was calculated from the original CCTA images. The plot depicts the direction and strength of association between individual radiomic features (calculated by Spearman's rho coefficient) and reveals the existence of distinct clusters of features.
Figure 5A:
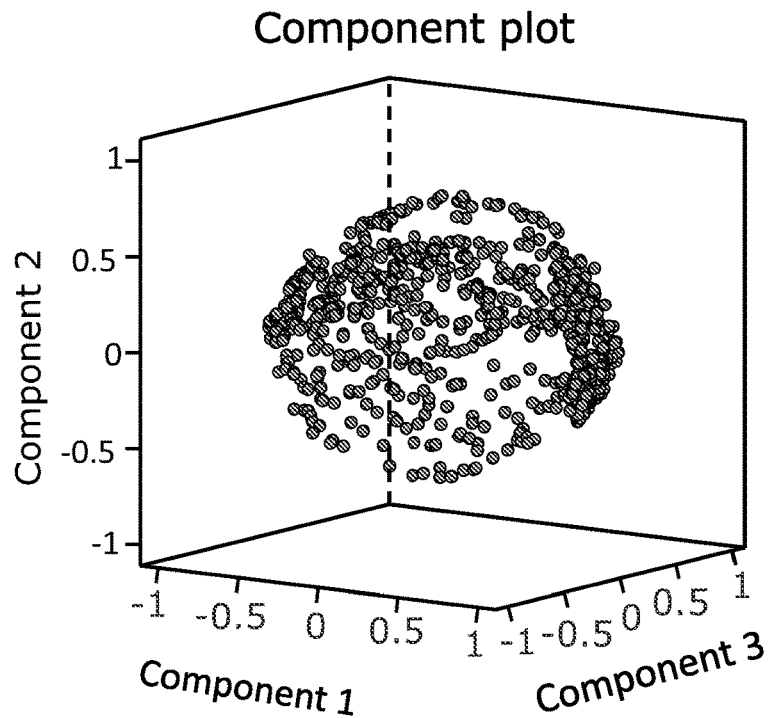
FIG. 5A shows a component plot of the three major principal components in Arm 1.
Figure 5B:
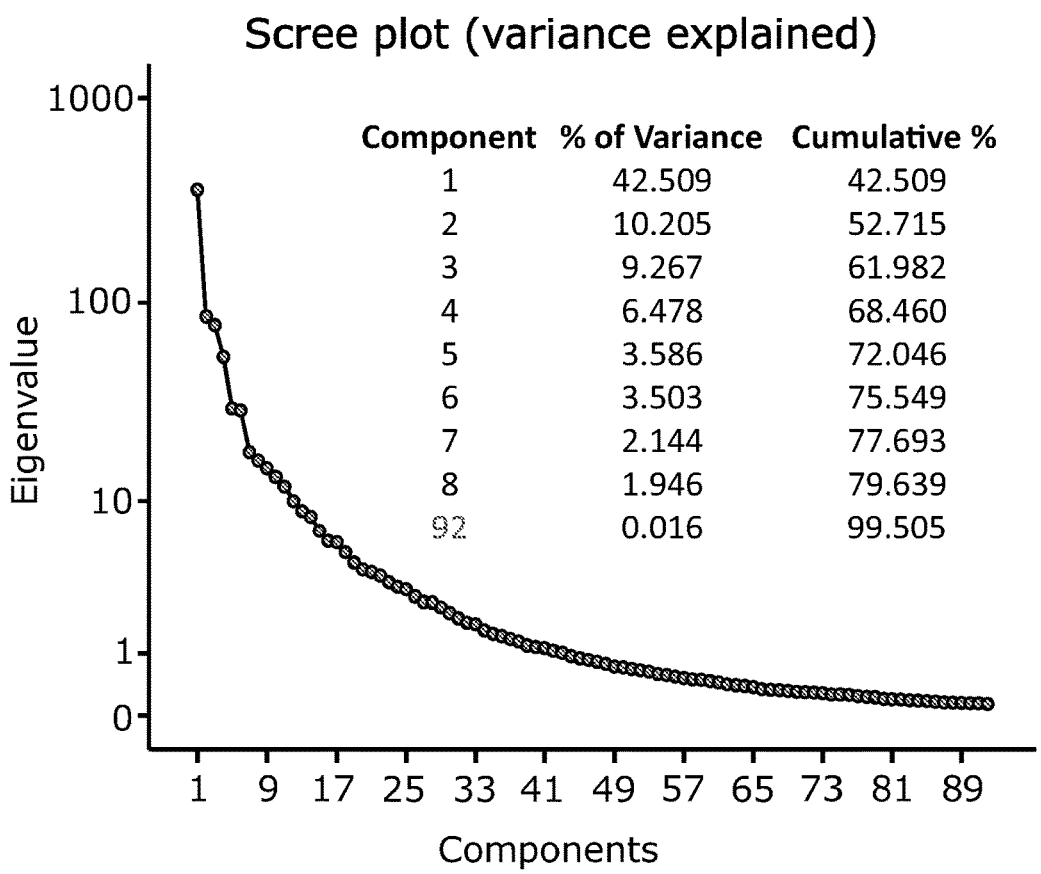
FIG. 5B shows a scree plot depicting the percentage of variation explained by the 92 first components, accounting for 99.5% of variation.
Figure 5C:
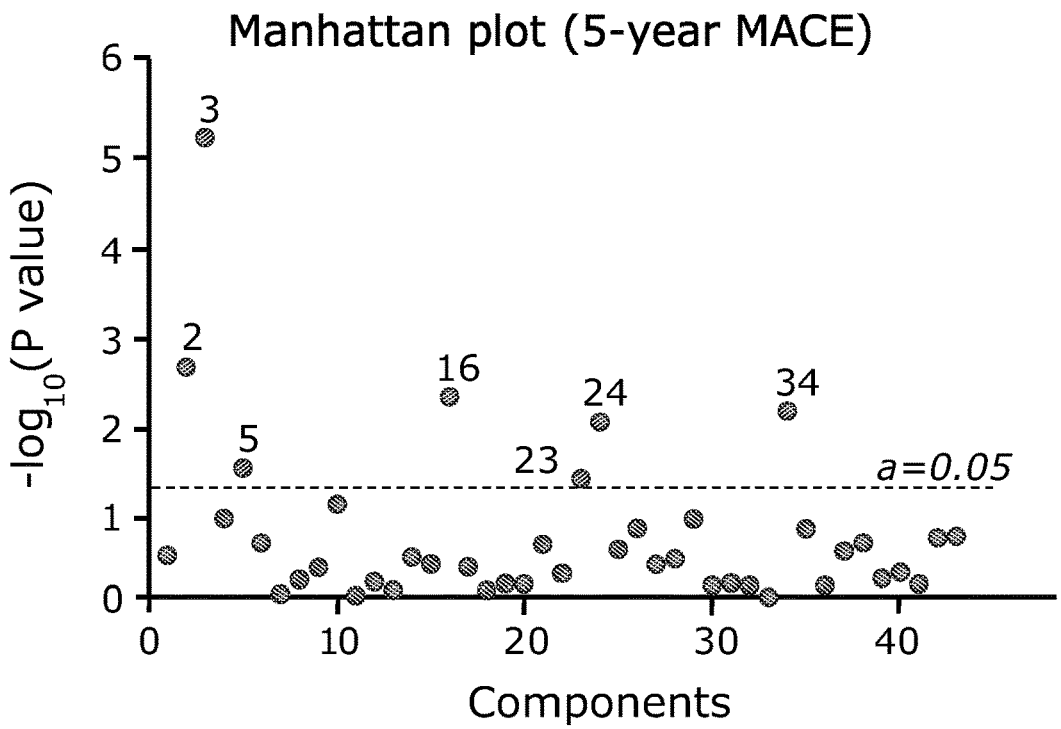
FIG. 5C shows a Manhattan plot for prediction of 5-year MACE for 42 components with eigenvalues >1.
Figure 5D:
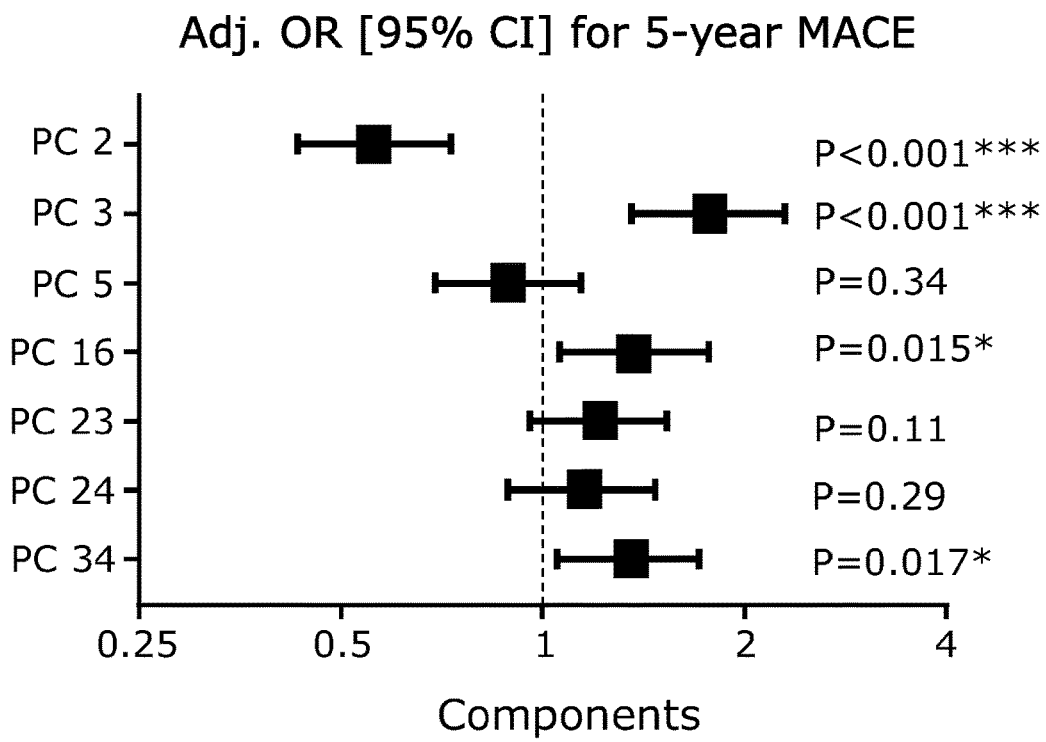
FIG. 5D shows a forest plot presenting the adjusted odds ratios (statistically adjusted for covariates such as age, gender) for prediction of 5-year MACE for the seven principal components that were significant in univariate analysis.
Figure 5E:
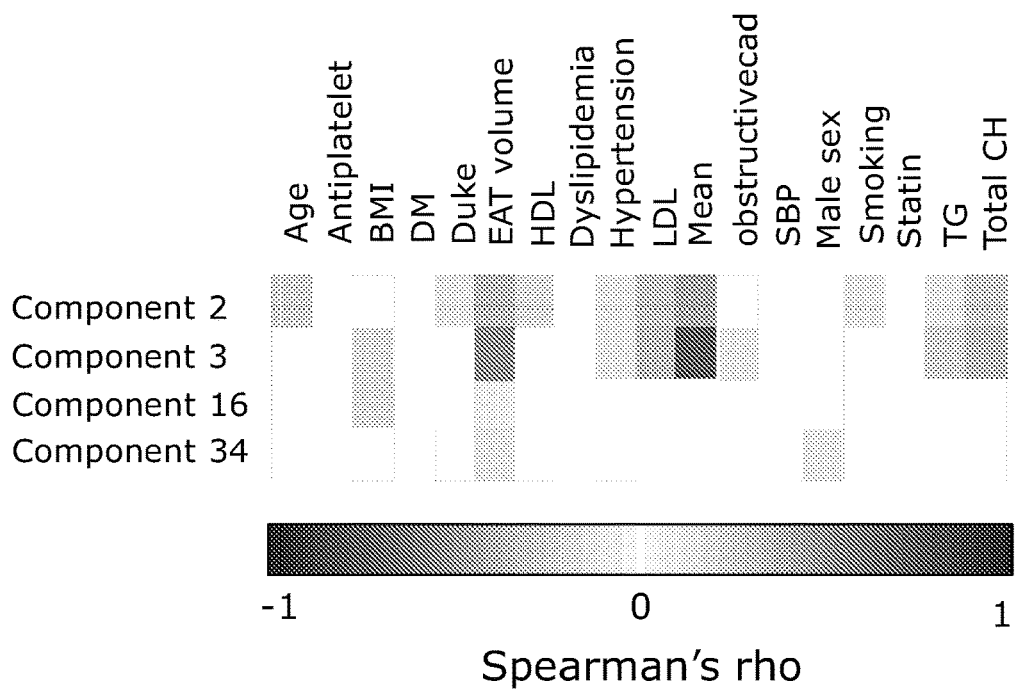
FIG. 5E shows a correlation plot of selected components with demographics.
Figure 5F:
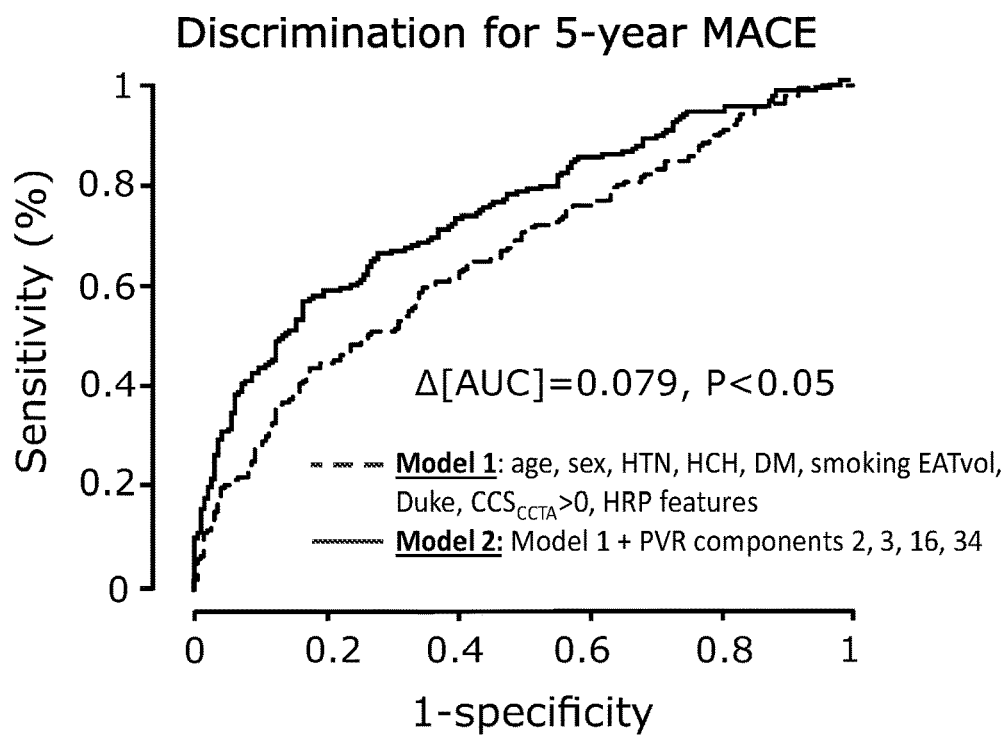
FIG. 5F illustrates the incremental prognostic value of perivascular region radiomic components for prediction of 5-year MACE. AUC: Area Under the Curve; BMI: body mass index; CCS: coronary calcium score; DM: diabetes mellitus; EAT: epicardial adipose tissue; HCH: hypercholesterolemia; HDL: high-density lipoprotein; LDL: low-density lipoprotein; PC: principal component; PVR: perivascular region; SBP: systolic blood pressure; TG: triglyceride.

A total of 103 radiomic features were calculated from the original images, corresponding to 15 shape-related features in addition to 18 first order statistics, 23 GLCM, 14 GLDM, 16 GLRLM, 16 GLSZ and 5 NGTDM individual features (Table 6, FIG. 4). All features, except for the shape-related features, were also calculated for each one of the eight wavelet transformation of the segmented region, resulting in a total of 843 radiomic features. Principal component analysis of all radiomic features revealed three principal components that accounted for 61.98% of the observed variation in both cohorts of Arm 1 (FIG. 5A), while 92 components accounted for 99.5% of the variation in the study population (scree plot presented in FIG. 5B). Out of 42 components with eigenvalues >1, a total of six components were significant predictors of MACE (FIG. 5C), while four components remained independently associated with MACE in a multiple regression model including all five components adjusted for age, sex, cardiovascular risk factors and CCTA-derived indices of CAD extent (FIG. 5D). These components were differentially associated with baseline clinical demographics and characteristics (FIG. 5E), possibly reflecting features of PVR that described distinct biological phenotypes. Of note, inclusion of the four PVR components in a model that included age, sex, cardiovascular risk factors and CCTA-derived risk features significantly improved discrimination for 5-year MACE (FIG. 5F), suggesting that radiomic phenotyping of PVR carries a strong and incremental prognostic value.

Unsupervised Clustering Based on Coronary PVR Phenotyping

Unsupervised (hierarchical) clustering of the pooled Arm 1 study population using the first three principal components of coronary PVR radiomics (PC1, PC2 and PC3) identified three distinct clusters with significantly different risk of 5-year MACE (46.5% vs 45.8% vs 65.8% MACE, P=0.009). Similarly, in Arm 2, hierarchical clustering of the identified coronary lesions, identified two distinct clusters with significant different prevalence of unstable plaques (58.8% vs 25%, P=0.01). These findings suggest the presence of a distinctive radiomic signature in PVR linked to increased cardiovascular disease and the local presence of coronary inflammation and unstable lesions.

Identifying Specific High-Risk PVR Radiomic Features

Principal component analysis and unsupervised clustering proved the concept that radiomic phenotyping of PVR can be linked to both local presence of coronary inflammation/disease and worse outcomes. However, they fail to identify specific high-risk radiomic features that can be reproducibly measured in independent cohorts.

Figure 6:
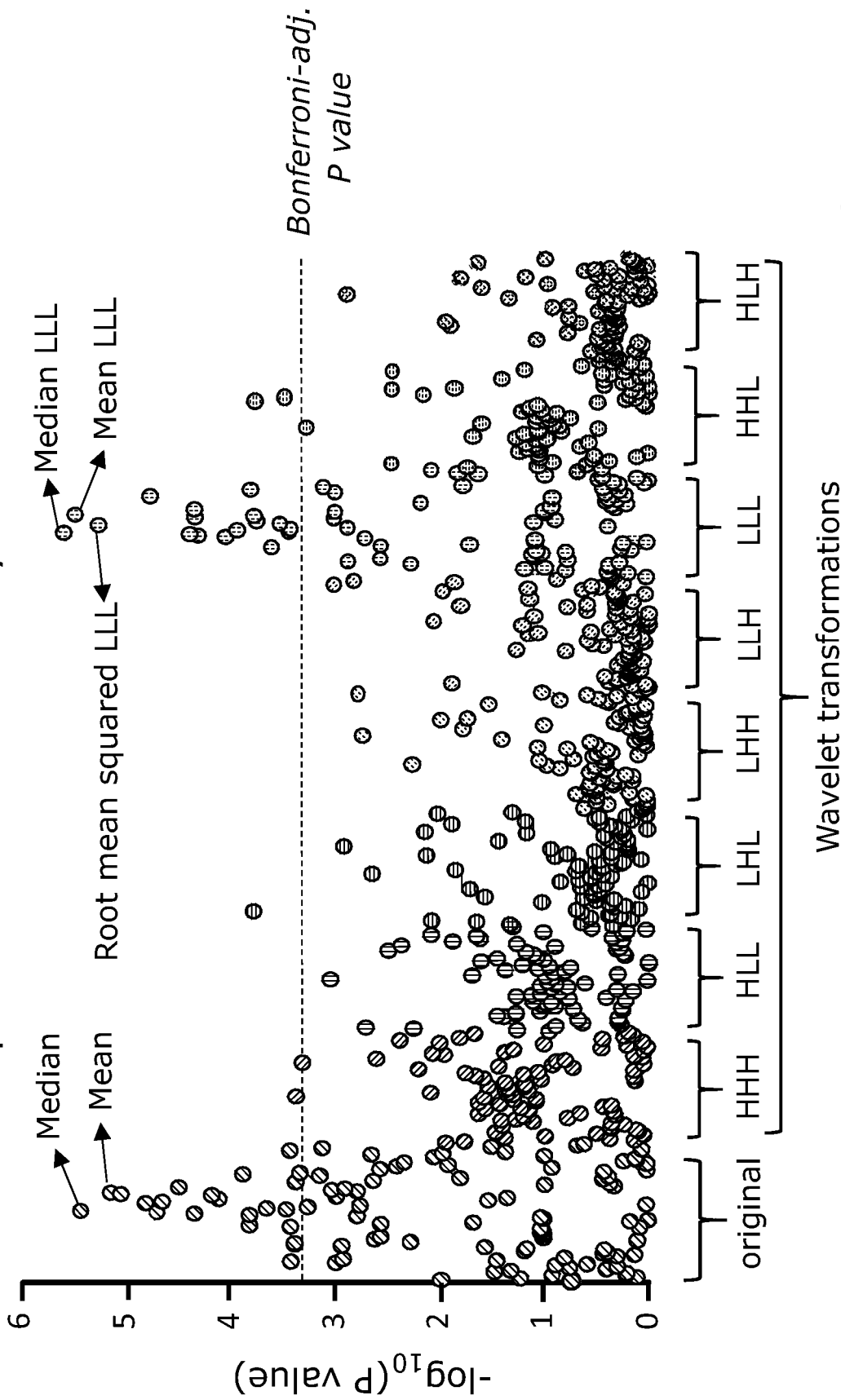
FIG. 6 shows a Manhattan plot for prediction of 5-year MACE. P values are derived from receiver operating characteristic (ROC) curve analysis for discrimination of 5-year MACE, for all radiomic features calculated on the original or wavelet-transformed images. MACE: major adverse cardiovascular events; H/L: high/low signal pass in wavelet transformations.

Principal components are specific to the dataset from which they were derived and are not easily applicable to independent datasets and cohorts. Further work was therefore undertaken to identify specific features that can supplement the diagnostic and prognostic information of the established $FAI_{PVAT}$ marker. In ROC analysis for discrimination of the primary endpoint of MACE, a total of 198 features were found to be significant at the level of 0.05 using the pooled data for both cohorts. In order to correct for multiple comparisons and decrease the false discovery rate (FDR), a Bonferroni correction was applied based on the principal component analysis (new significance cutoff=0.05/92=0.00054347826). Following this correction, only 46 radiomic features remained significant discriminators of MACE, as summarized in a Manhattan plot (FIG. 6) and in Table 3. Of these 46 radiomic features, 28 were first order statistics, 10 GLRLM, 5 GLCM, 1 GLDM, 1 GLSZ and 1 NGTDM, while half were derived from the original image and the other half from wavelet transformation (17 LLL, 2 HHH, 3 HHL and 1 LHL).

Building a High-Risk PVR Radiomic Signature

Figure 2B:
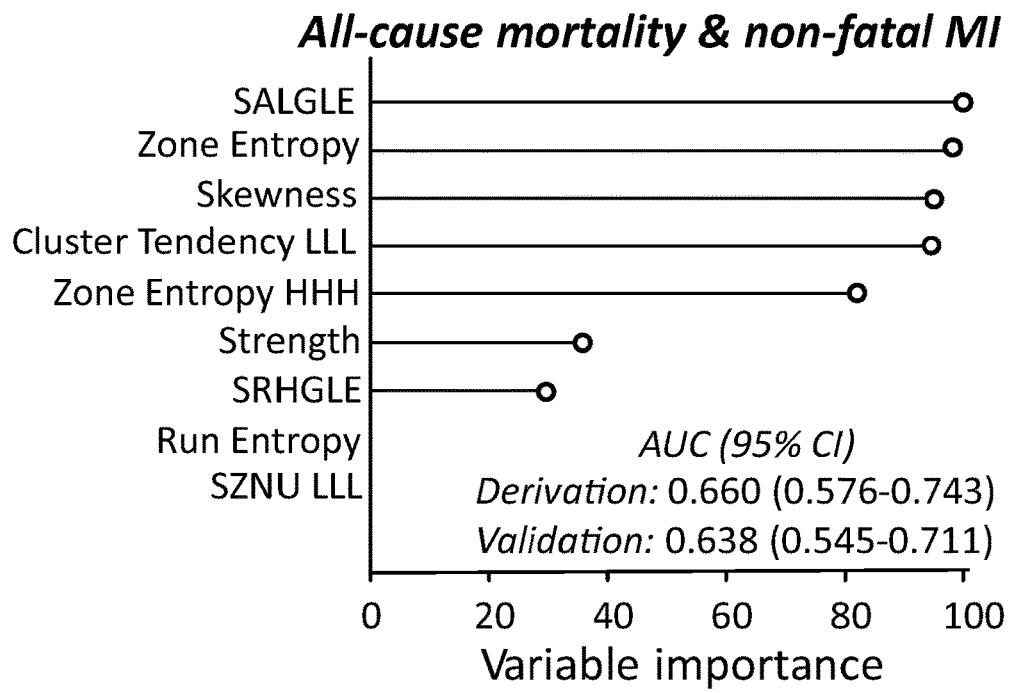
FIG. 2B shows the relative variable importance (weighting) for the best performing model for prediction of MACE.
Figure 2C:
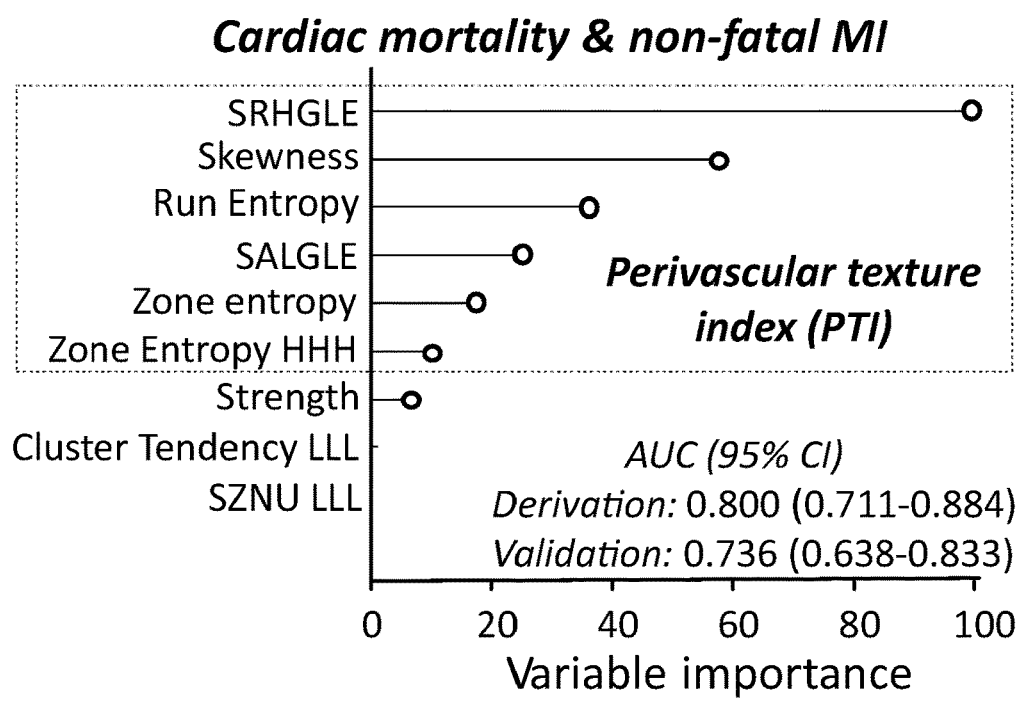
FIG. 2C shows the relative variable importance (weighting) for the best performing model for prediction of cardiac-specific MACE (cMACE). The top six components of the model of FIG. 2C were then used to define the Perivascular Texture Index (PTI), which is a radiomic signature according the invention. AUC: area under the curve; CI: confidence interval; MACE: major adverse cardiovascular events; SALGLE: small area low gray level emphasis; SRHGLE: short run high gray level emphasis; SZNU: size zone non-uniformity.
Figure 7:
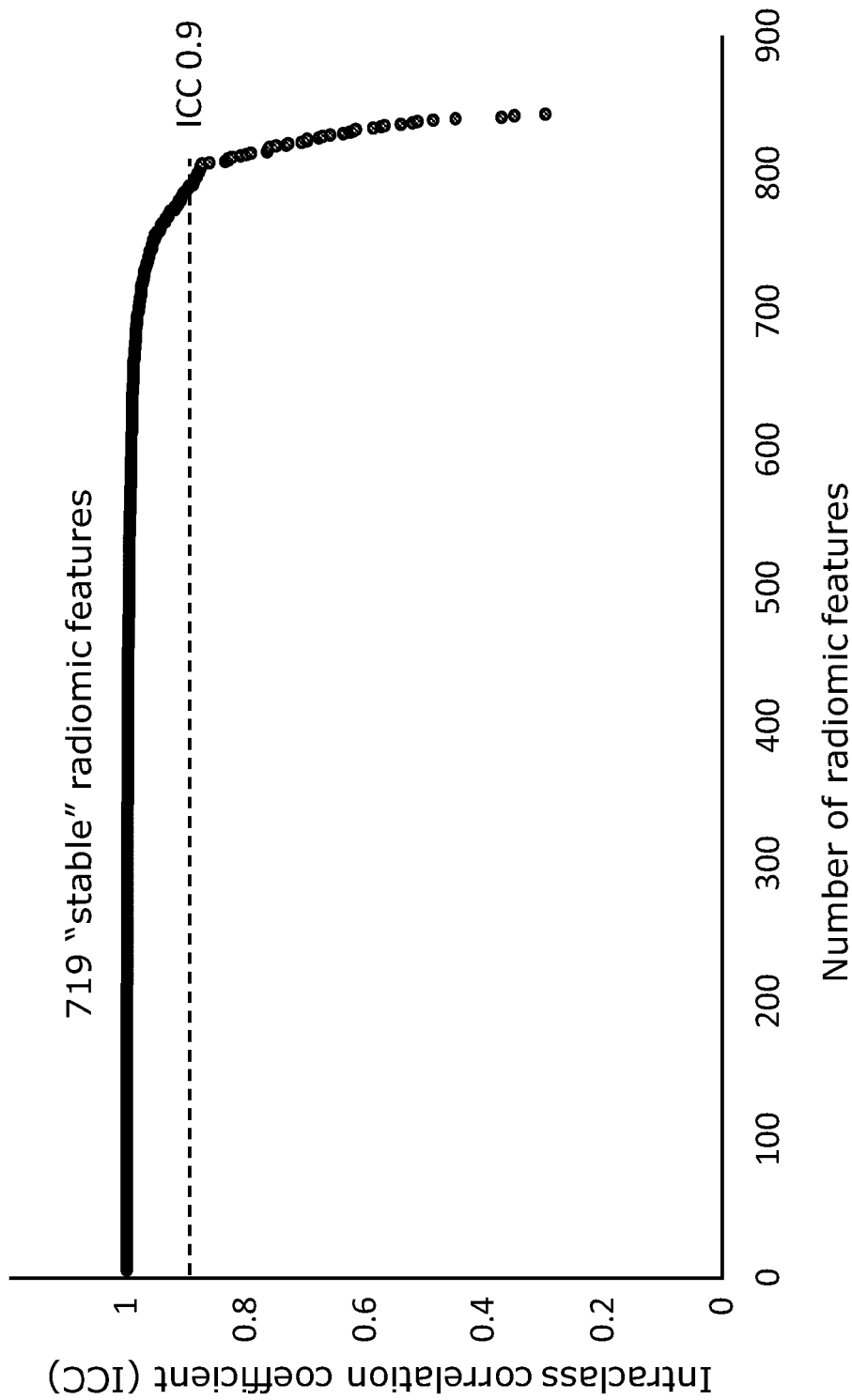
FIG. 7 shows a plot of the intraclass correlation coefficient (ICC) of all the perivascular region radiomic features. The radiomic features are ranked according to the intraclass correlation coefficient (ICC) in repeated analysis. A total of 719 radiomic features were found to have ICC≥0.9.

While individual radiomic features such as $FAI_{PVAT}$ are associated with an increased cardiovascular risk, it was previously unknown whether a combination ("signature") of different radiomic features may provide a more powerful way to characterize the adverse profile of coronary PVR. To explore this hypothesis and develop a radiomic signature that would be both prognostic and reproducible, a stringent, stepwise approach was applied (FIG. 2). First, out of the 843 coronary PVR radiomic features that were calculated, 143 were excluded following stability analysis (ICC<0.9, two measurements) (FIG. 7). Next, 60 volume- and orientation-independent radiomic features that were significantly associated with MACE at the level of $\alpha=0.05$ in both cohorts were selected, in order to reduce possible false positive findings due to cohort-specific variations. Collinearity was subsequently reduced by stepwise elimination of pairwise correlations at the level of $|rho| \geq 0.75$ (Spearman's rho). Using the remaining nine radiomic features, a machine learning approach was applied in Cohort 1 using elastic net/lasso regression and leave-one-out internal cross-validation. The best performing model for prediction of MACE showed average discrimination (FIG. 2B), and a similar model for prediction of cardiac-specific MACE (FIG. 2C) showed very good discriminatory value in both Cohort 1 (derivation) and Cohort 2 (validation cohort). The top six components of this model were then used to define the Perivascular Texture Index (PTI) using the model-derived coefficients, as shown in Table 7. Table 7 therefore describes a particular example of the radiomic signature of the invention.

TABLE 7

Defining the high-risk PVR texture signature

| PVR radiomic feature ($rf_i$) | Radiomic feature group | z-score betas ($b_z$) | unstand. Betas ($b_i$) |
|---|---|---|---|
| SRHGLE | GLRLM | 4.0689831 | 0.257217 |
| Skewness | First Order | 2.4393009 | 8.721041 |
| Run Entropy | GLRLM | 1.5392412 | 7.914576 |
| SALGLE | First order | 1.0821666 | 141.4015 |
| Zone Entropy (HHH) | GLSZM | −0.5023836 | −0.85001 |
| Zone Entropy | GLSZM | 0.8234266 | 3.504424 |

Perivascular Texture Index (PTI) = 90 − $\Sigma b_i \, rf_i$
GLRLM: gray level run length matrix; GLSZM: gray level size zone matrix; PVR: perivascular region; SRHGLE: Short Run High Gray Level Emphasis; SALGLE: small area low gray level emphasis; SZNU: size zone nonuniformity.

In Table 7, z-score betas were converted to unstandardized betas ($b_1$) by multiplying $b_z$ by the standard deviation of the respective variable in the derivation cohort (Cohort 1). A constant of 90 was added post-hoc to ensure positive values based on the range of values observed in all cohorts that were analysed.

Incremental Value of PVR Radiomic Phenotyping Beyond Current State-of-the-Art

Figure 3A:
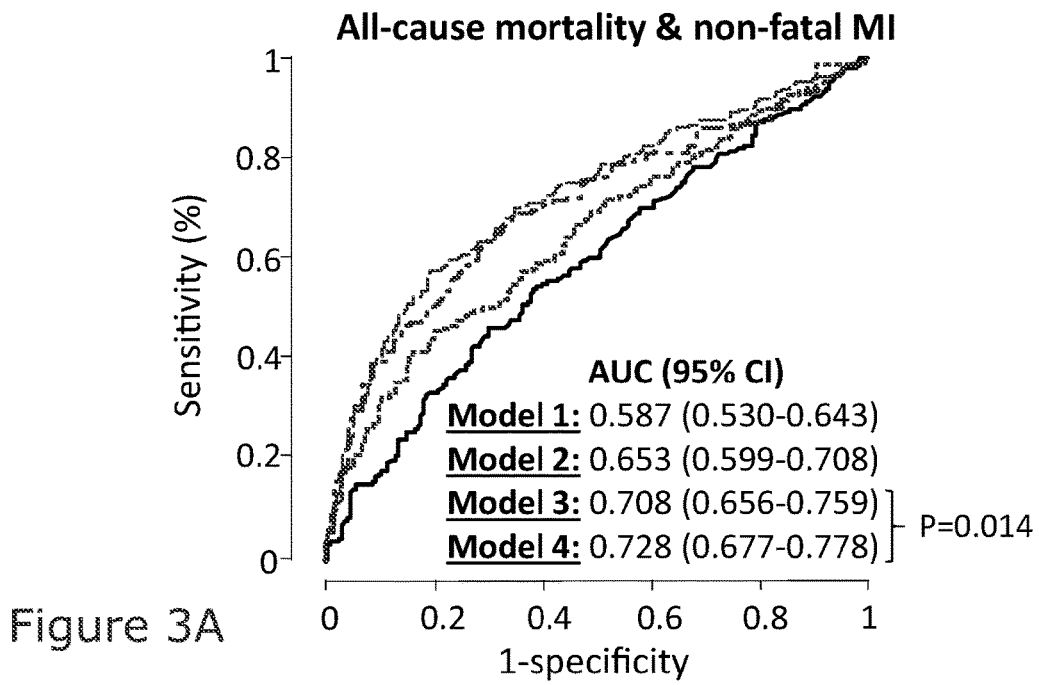
FIG. 3 shows that the PTI signature of the invention provides incremental prognostic information beyond current CCTA-based tools. In a pooled analysis of both Arm 1 cohorts, addition of the perivascular texture index (PTI) into a model consisting of age, sex, traditional risk factors and computed tomography-derived high-risk features, including pericoronary $FAI_{PVAT}$, significantly improved the predictive value of the model for both MACE (δ[AUC]=0.020, P=0.014, FIG. 3A), and cardiac-specific MACE (δ[AUC]=0.046, P=0.012, FIG. 3B). Of note, PTI and $FAI_{PVAT}$ were independently associated with the risk for both endpoints, with higher values of both biomarkers linked to a higher prospective risk of adverse events. The interaction between the two CT-derived perivascular region (PVR) features (PTI and FAI) is presented graphically in FIG. 3C using two-way contour plots depicting the adjusted probability for MACE (left) and cardiac-specific MACE (right) across different levels of the two biomarkers. These findings suggest a significant clinical value for comprehensive phenotyping of coronary perivascular region by means of both $FAI_{PVAT}$ and PTI.
Figure 3B:
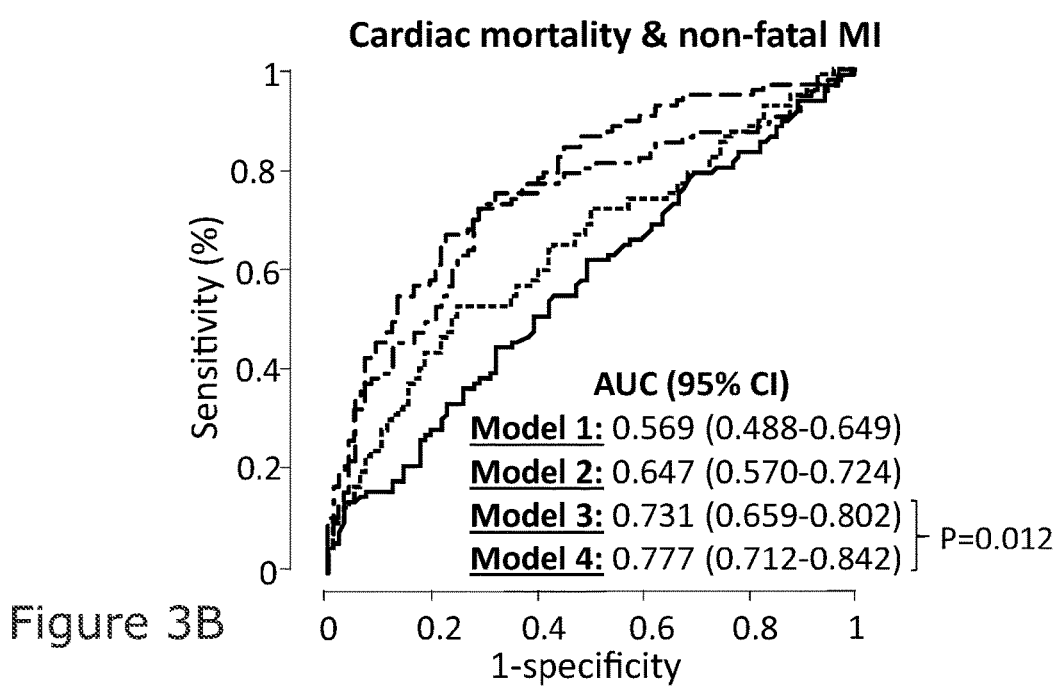
Figure 3C:
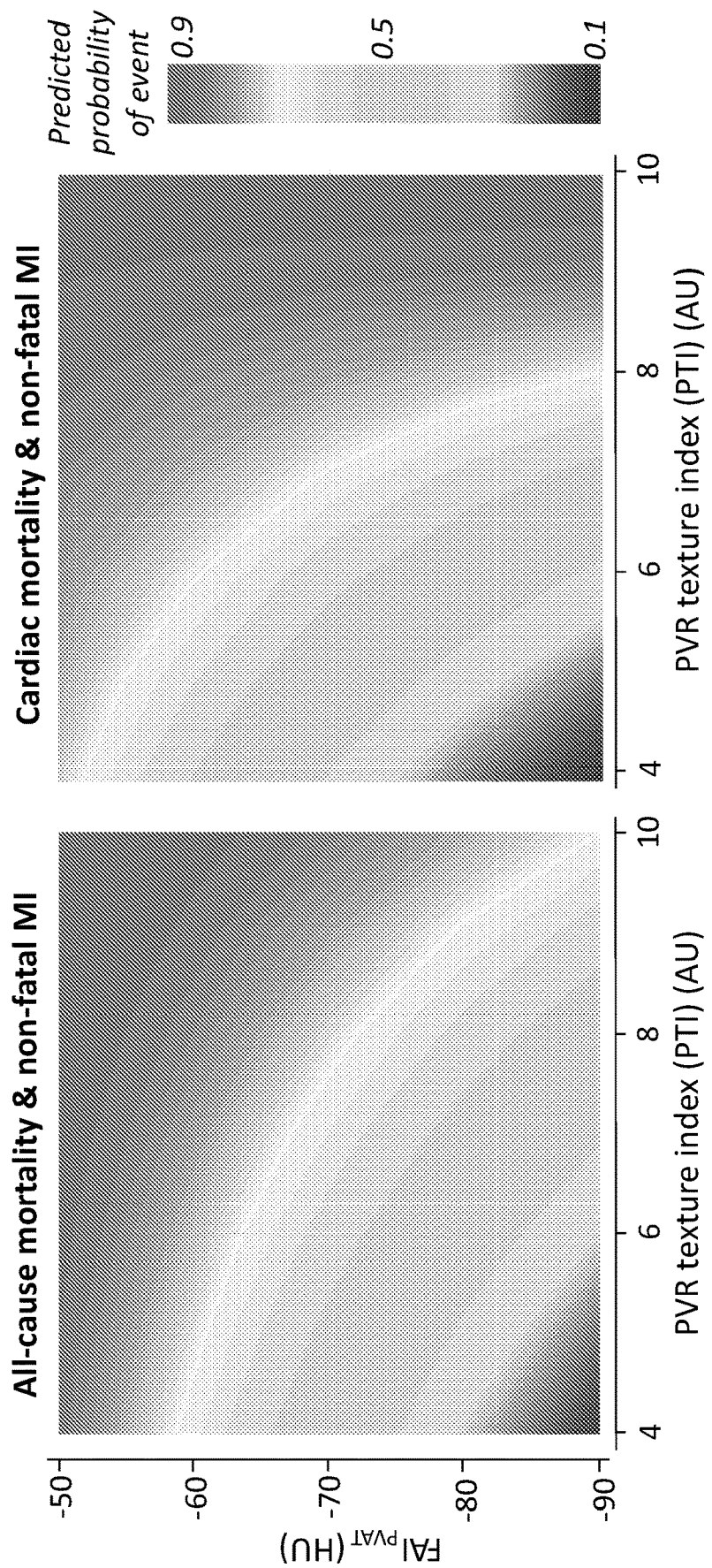

To assess the incremental value of $FAI_{PVAT}$ radiomic phenotyping beyond current risk biomarkers used in CCTA-based risk stratification, a set of nested models were constructed, as shown in FIGS. 3A and 3B. Model 1 consisted of demographics and conventional risk factors, which showed poor discrimination for both MACE and cMACE in part due to the matching process for the selection of the control group. Addition of CCTA-derived risk features (including Duke Prognostic CAD index, presence of coronary calcium, high-risk plaque features, and EAT (epicardial adipose tissue) volume) significantly improved discrimination for both MACE and cMACE, while inclusion of $FAI_{PVAT}$ further increased discrimination for both endpoints. Despite this remarkable improvement, the addition of PTI (as defined in Table 7) was associated with a further significant improvement in the discriminatory value of the model for both endpoints (FIGS. 3A and 3B), suggesting not only an independent but also an incremental value for PVR texture phenotyping in risk prediction. The interaction between $FAI_{PVAT}$ and PTI for prediction of MACE/cMACE is graphically presented in FIG. 3C, which demonstrates that for a given $FAI_{PVAT}$ value, there is an increasing risk at higher levels of PTI and vice versa.

Validating Alternative Radiomic Signatures (PTIs) of the Invention

The data presented in FIGS. 3A and 3B demonstrate that the radiomic signature (PTI) defined in Table 7 provides a significant improvement in the discriminatory value of the model for both endpoints (MACE and cMACE). To validate the usefulness of alternative radiomic signatures of the invention that include different selections of radiomic features, a series of models including several different radiomic signatures were tested against a current state of the art model.

In Table 8, improvements in model performance are presented in 196 patients (98 with cardiac MACE and 98 matched controls). Each step corresponds to inclusion of one selected radiomic feature on top of the current state-of-the-art model and radiomic features of previous clusters. The current state-of-the-art model includes age, sex, hypertension, dyslipidemia, smoking and diabetes mellitus, Duke Prognostic Coronary Artery Disease index, presence of high-risk plaque features, epicardial adipose tissue volume and presence of coronary calcium.

In each of Examples 1-4, the current state of the art model was progressively supplemented by a radiomic signature including progressively more radiomic features from different clusters. First, the state of the art model was supplemented by a radiomic signature calculated on the basis of a radiomic feature selected from cluster 1 (first row of Tables 8A and 8B: "+Cluster 1"). Next, the state of the art model was supplemented by a radiomic signature calculated on the basis of two radiomic features selected from clusters 1 and 2 (first row of Tables 8A and 8B: "+Cluster 2"). Thus, each progressive row of Tables 8A and 8B corresponds to the inclusion of one selected radiomic feature on top of the current state-of-the-art model and the radiomic features of previous clusters. Nagelkerke's pseudo-$R^2$ provides a measure of the discrimination of the model for cMACE.

It can clearly be seen from Tables 8A and 8B that the signatures of the invention calculated on the basis of different selections of radiomic features from the identified clusters all provide improved prediction for cardiac-specific MACE. Thus, the data presented in Table 8 demonstrate that regardless of which features are selected from each of the identified clusters, or precisely how many are selected, the radiomic signature (PTI) of the invention provides improved prediction of cardiovascular risk over previously used models.

TABLE 8A

Improved prediction for cardiac-specific MACE with different selections of radiomic features from the identified clusters

| | Example 1: "Original" radiomic features (Table 1) | Nagelkerke's pseudo-$R^2$ (delta from previous step) | Example 2: Top alternative feature from each cluster of Table 2 (expanded clusters) | Nagelkerke's pseudo-$R^2$ (delta from previous step) |
|---|---|---|---|---|
| | Current state-of-the-art* | 0.110 (—) | — | 0.110 (—) |
| +Cluster 1 | Short Run High Gray Level Emphasis | 0.174 (+0.064) | High Gray Level Emphasis | 0.179 (+0.069) |
| +Cluster 2 | Skewness | 0.211 (+0.037) | Skewness LLL | 0.205 (+0.026) |
| +Cluster 3 | Run Entropy | 0.229 (+0.018) | Dependence Entropy LLL | 0.214 (+0.009) |
| +Cluster 4 | Small Area Low Gray Level Emphasis | 0.252 (+0.023) | Low Gray Level Zone Emphasis | 0.242 (+0.028) |
| +Cluster 5 | Zone Entropy | 0.295 (+0.043) | Gray Level Non Uniformity Normalized (GLRLM) | 0.249 (+0.007) |
| +Cluster 6 | Zone Entropy HHH | 0.296 (+0.001) | Size Zone Non Uniformity Normalized HHH | 0.303 (+0.054) |
| +Cluster 7 | Strength | 0.298 (+0.002) | Coarseness HLL | 0.306 (+0.003) |
| +Cluster 8 | Cluster tendency LLL | 0.299 (+0.001) | Cluster Tendency | 0.309 (+0.003) |
| +Cluster 9 | Size Zone Non Uniformity LLL | 0.300 (+0.001) | Dependence Non Uniformity HLL | 0.311 (+0.002) |

TABLE 8B

Improved prediction for cardiac-specific MACE with different selections of radiomic features from the identified clusters

| | Example 3: Bottom alternative feature from each cluster of Table 2 (expanded clusters) | Nagelkerke's pseudo-$R^2$ (delta from previous step) | Example 4: Top alternative feature from each cluster of Table 1 (standard clusters) | Nagelkerke's pseudo-$R^2$ (delta from previous step) |
|---|---|---|---|---|
| | Current state-of-the-art* | 0.110 (—) | — | 0.110 (—) |
| +Cluster 1 | High Gray Level Zone Emphasis | 0.140 (+0.030) | High Gray Level Emphasis | 0.179 (+0.069) |
| +Cluster 2 | Median | 0.234 (+0.094) | Skewness LLL | 0.205 (+0.026) |
| +Cluster 3 | Mean LLL | 0.236 (+0.002) | Run Entropy LLL | 0.242 (+0.037) |
| +Cluster 4 | Contrast | 0.237 (+0.001) | Low Gray Level Zone Emphasis | 0.243 (+0.001) |
| +Cluster 5 | Uniformity | 0.248 (+0.011) | Zone Entropy | 0.245 (+0.002) |
| +Cluster 6 | Small Area Emphasis HHH | 0.289 (+0.041) | Zone Entropy HHH | 0.284 (+0.039) |
| +Cluster 7 | Coarseness LHH | 0.289 (+0.000) | Strength | 0.285 (+0.001) |
| +Cluster 8 | 10th Percentile | 0.297 (+0.008) | Cluster Tendency | 0.298 (+0.013) |
| +Cluster 9 | Run Length Non Uniformity HHH | 0.304 (+0.007) | Busyness | 0.303 (+0.005) |

PVR Radiomic Phenotyping to Detect Unstable Lesions

When calculated around pre-defined coronary lesions in Study Arm 2, all but one of the identified radiomic features used to define PTI were significantly altered in the presence of unstable, culprit lesions (scanned within 96 hours of ACS onset) compared to stable, treated lesions (scanned >3 months post-PCI) (FIGS. 8A-G). More importantly, PTI (defined using the formula of Table 7) outperformed all six individual radiomic features in discriminating unstable form stable coronary lesions (AUC: 0.76; 95% confidence interval: 0.64-0.88) (FIG. 8G). These findings suggest the value of perivascular fat phenotyping by means of PTI in combination with $FAI_{PVAT}$ for both future risk prediction and detection of unstable coronary plaques, and reveal a close link between perivascular fat phenotype and vascular inflammation, plaque instability and adverse clinical outcomes.

Summary of Findings

Using a machine learning approach, the inventors have discovered and validated a coronary PVR radiomic signature that adds incremental value beyond traditional risk factors and established CCTA risk classification tools in predicting future adverse events and evaluating cardiovascular health and risk, and further detects local plaque inflammation and the presence of unstable coronary lesions. The inventors have demonstrated that a PVR radiomic signature based on two or more radiomic features of the PVR provides a tool for predicting future adverse events in patients, for diagnosing coronary artery disease or coronary heart disease, and for identifying unstable coronary lesions.

The PVR signature of the invention describes the high-risk PVR phenotype, linking it to future event risk, and offers incremental prognostic information beyond current CCTA-based tools. The signature of the invention is also able to discriminate unstable from stable coronary lesions based on the radiomic signature of peri-lesion fat. Taken together, the findings presented herein demonstrate that PVR radiomic phenotyping by means of the radiomic signature of the invention can be used to identify both the high-risk patient (when measured in a standardized way around coronary vessels) and the high-risk lesion (when applied around a specific coronary segment or lesion) with important implications for modern CCTA-based risk prediction.

Surprisingly, the radiomic signature need not be constructed from the radiomic features that are most strongly independently associated with future adverse events. Instead, it is actually advantageous to include a selection of radiomic features from different collinear "clusters" of radiomic features instead of merely including those radiomic features that are individually most associated with adverse events.

A particularly attractive aspect of the invention is that it can be performed on historic medical imaging data that have been collected previously. The signature of the invention may be derived and calculated based on historic imaging data and the invention therefore provides a convenient tool for assessing a large number of patients without the need to perform further scans. The method of the invention need not therefore include the step of collecting the medical imaging data and can be performed based on a post-hoc analysis of existing medical imaging data.

Selected Aspects of the Invention

The following numbered clauses disclose various aspects of the invention.

Clause 1. A method for characterising a perivascular region using medical imaging data of a subject, the method comprising calculating the value of a radiomic signature of the perivascular region using the medical imaging data;
wherein the radiomic signature is calculated on the basis of measured values of at least two radiomic features of the perivascular region, the measured values of the at least two radiomic features being calculated from the medical imaging data.

Clause 2. The method of clause 1, wherein the at least two radiomic features are selected from the radiomic features of clusters 1 to 9, wherein the at least two radiomic features are each selected from different clusters, wherein:
cluster 1 consists of Short Run High Gray Level Emphasis, High Gray Level Emphasis, High Gray Level Run Emphasis, Autocorrelation, Sum Average, Joint Average, and High Gray Level Zone Emphasis;
cluster 2 consists of Skewness, Skewness LLL, Kurtosis, 90th Percentile, 90th Percentile LLL, Median LLL, Kurtosis LLL, and Median;
cluster 3 consists of Run Entropy, Dependence Entropy LLL, Dependence Entropy, Zone Entropy LLL, Run Entropy LLL, and Mean LLL;
cluster 4 consists of Small Area Low Gray Level Emphasis, Low Gray Level Zone Emphasis, Short Run Low Gray Level Emphasis, Low Gray Level Run Emphasis, Low Gray Level Emphasis, Small Dependence Low Gray Level Emphasis, Gray Level Variance LLL (GLSZM), Gray Level Variance (GLDM), Variance, Gray Level Variance (GLDM), Difference Variance LLL, Gray Level Variance LLL (GLRLM), Variance LLL, Gray Level Variance LLL (GLDM), Sum of Squares, Contrast LLL, Mean Absolute Deviation, Interquartile Range, Robust Mean Absolute Deviation, Long Run Low Gray Level Emphasis, Difference Variance, Gray Level Variance (GLSZM), Inverse Difference Moment Normalized, Mean Absolute Deviation LLL, Sum of Squares LLL, and Contrast;
cluster 5 consists of Zone Entropy, Gray Level Non Uniformity Normalized (GLRLM), Gray Level Non Uniformity Normalized LLL (GLRLM), Sum Entropy, Joint Energy, Entropy, Gray Level Non Uniformity Normalized (GLDM), Joint Energy, Gray Level Non Uniformity Normalized LLL (GLDM), Uniformity LLL, Sum Entropy LLL, and Uniformity;
cluster 6 consists of Zone Entropy HHH, Size Zone Non Uniformity Normalized HHH, and Small Area Emphasis HHH;
cluster 7 consists of Strength, Coarseness HLL, Coarseness, Coarseness LHL, Coarseness LLL, Coarseness LLH, Coarseness HHH, Coarseness HLH, Coarseness HHL, and Coarseness LHH;
cluster 8 consists of Cluster Tendency LLL, Cluster Tendency, Sum of Squares LLL, Mean Absolute Deviation LLL, Gray Level Variance LLL (GLDM), Variance LLL, Gray Level Variance LLL (GLRLM), Gray Level Variance (GLRLM), Robust Mean Absolute Deviation LLL, Gray Level Variance (GLDM), Variance, Mean Absolute Deviation, Cluster Prominence, Sum Entropy LLL, Interquartile Range LLL, Gray Level Variance LLL (GLSZM), Sum of Squares, Robust Mean Absolute Deviation, Sum Entropy, Interquartile Range, Cluster Prominence LLL, Entropy LLL, 10th Percentile LLL, 10th Percentile; and
cluster 9 consists of Size Zone Non Uniformity LLL, Dependence Non Uniformity HLL, Gray Level Non Uniformity HLL (GLSZM), Gray Level Non Uniformity (GLSZM), Run Length Non Uniformity HHL, Run Length Non Uniformity LHL, Dependence Non Uniformity LHL, Dependence Non Uniformity, Run Length Non Uniformity HLH, Busyness, Run Length Non Uniformity LLH, Dependence Non Uniformity LLH, Dependence Non Uniformity LLL, Size Zone Non Uniformity, Energy HLL, Run Length Non Uniformity LHH, Size Zone Non Uniformity HLL, Gray Level Non Uniformity LLH (GLSZM), Gray Level Non Uniformity LHL (GLSZM), Gray Level Non Uniformity LLL (GLSZM), Run Length Non Uniformity HLL, Gray Level Non Uniformity HLH (GLSZM), Gray Level Non Uniformity HHL (GLSZM), Run Length Non Uniformity, and Run Length Non Uniformity HHH.

Clause 3. The method of clause 2, wherein:
cluster 1 consists of Short Run High Gray Level Emphasis, High Gray Level Emphasis, High Gray Level Run Emphasis, Autocorrelation, Sum Average, and Joint Average;
cluster 2 consists of Skewness, Skewness LLL, Kurtosis, 90th Percentile, 90th Percentile LLL, Median LLL, and Kurtosis LLL;
cluster 3 consists of Run Entropy, Dependence Entropy LLL, Dependence Entropy, and Zone Entropy LLL;
cluster 4 consists of Small Area Low Gray Level Emphasis, Low Gray Level Zone Emphasis, Short Run Low Gray Level Emphasis, Low Gray Level Run Emphasis, Low Gray Level Emphasis, Small Dependence Low Gray Level Emphasis, Gray Level Variance LLL (GLSZM), Gray Level Variance (GLDM), Variance, Gray Level Variance (GLDM), and Difference Variance LLL;
cluster 5 consists of Zone Entropy, Gray Level Non Uniformity Normalized (GLRLM), and Gray Level Non Uniformity Normalized LLL (GLRLM);
cluster 6 consists of Zone Entropy HHH, and Size Zone Non Uniformity Normalized HHH;

cluster 7 consists of Strength, Coarseness HLL, Coarseness, Coarseness LHL, Coarseness LLL, Coarseness LLH, and Coarseness HHH;

cluster 8 consists of Cluster Tendency LLL, Cluster Tendency, Sum of Squares LLL, Mean Absolute Deviation LLL, Gray Level Variance LLL (GLDM), Variance LLL, Gray Level Variance LLL (GLRLM), Gray Level Variance (GLRLM), Robust Mean Absolute Deviation LLL, Gray Level Variance (GLDM), Variance, Mean Absolute Deviation, Cluster Prominence, Sum Entropy LLL, Interquartile Range LLL, Gray Level Variance LLL (GLSZM), Sum of Squares, Robust Mean Absolute Deviation, Sum Entropy, Interquartile Range, Cluster Prominence LLL, Entropy LLL, 10th Percentile LLL, and 10th Percentile; and cluster 9 consists of Size Zone Non Uniformity LLL, Dependence Non Uniformity HLL, Gray Level Non Uniformity HLL (GLSZM), Gray Level Non Uniformity (GLSZM), Run Length Non Uniformity HHL, Run Length Non Uniformity LHL, Dependence Non Uniformity LHL, Dependence Non Uniformity, Run Length Non Uniformity HLH, Busyness, Run Length Non Uniformity LLH, Dependence Non Uniformity LLH, Dependence Non Uniformity LLL, Size Zone Non Uniformity, Energy HLL, Run Length Non Uniformity LHH, Size Zone Non Uniformity HLL, Gray Level Non Uniformity LLH (GLSZM), and Gray Level Non Uniformity LHL (GLSZM).

Clause 4. The method of clause 2, wherein:

cluster 1 consists of Short Run High Gray Level Emphasis, High Gray Level Emphasis, High Gray Level Run Emphasis, Autocorrelation, Sum Average, and Joint Average;

cluster 2 consists of Skewness, Skewness LLL, Kurtosis, and 90th Percentile;

cluster 3 consists of Run Entropy, Dependence Entropy LLL, and Dependence Entropy;

cluster 4 consists of Small Area Low Gray Level Emphasis, Low Gray Level Zone Emphasis, Short Run Low Gray Level Emphasis, Low Gray Level Run Emphasis, Low Gray Level Emphasis, and Small Dependence Low Gray Level Emphasis;

cluster 5 consists of Zone Entropy, and Gray Level Non Uniformity Normalized (GLRLM);

cluster 6 consists of Zone Entropy HHH;

cluster 7 consists of Strength, Coarseness HLL, Coarseness, Coarseness LHL, Coarseness LLL, and Coarseness LLH;

cluster 8 consists of Cluster Tendency LLL, Cluster Tendency, Sum of Squares LLL, Mean Absolute Deviation LLL, Gray Level Variance LLL (GLDM), Variance LLL, Gray Level Variance LLL (GLRLM), Gray Level Variance (GLRLM), Robust Mean Absolute Deviation LLL, Gray Level Variance (GLDM), Variance, Mean Absolute Deviation, Cluster Prominence, Sum Entropy LLL, Interquartile Range LLL, Gray Level Variance LLL (GLSZM), Sum of Squares, Robust Mean Absolute Deviation, Sum Entropy, Interquartile Range, Cluster Prominence LLL, Entropy LLL, 10th Percentile LLL, and 10th Percentile; and cluster 9 consists of Size Zone Non Uniformity LLL, Dependence Non Uniformity HLL, Gray Level Non Uniformity HLL (GLSZM), Gray Level Non Uniformity (GLSZM), Run Length Non Uniformity HHL, Run Length Non Uniformity LHL, Dependence Non Uniformity LHL, Dependence Non Uniformity, Run Length Non Uniformity HLH, Busyness, Run Length Non Uniformity LLH, Dependence Non Uniformity LLH, Dependence Non Uniformity LLL, and Size Zone Non Uniformity.

Clause 5. The method of clause 2, wherein:

cluster 1 consists of Short Run High Gray Level Emphasis, High Gray Level Emphasis, High Gray Level Run Emphasis, and Autocorrelation;

cluster 2 consists of Skewness, and Skewness LLL;

cluster 3 consists of Run Entropy, and Dependence Entropy LLL;

cluster 4 consists of Small Area Low Gray Level Emphasis, and Low Gray Level Zone Emphasis;

cluster 5 consists of Zone Entropy;

cluster 6 consists of Zone Entropy HHH;

cluster 7 consists of Strength;

cluster 8 consists of Cluster Tendency LLL, Cluster Tendency, Sum of Squares LLL, Mean Absolute Deviation LLL, Gray Level Variance LLL (GLDM), Variance LLL, Gray Level Variance LLL (GLRLM), Gray Level Variance (GLRLM), Robust Mean Absolute Deviation LLL, Gray Level Variance (GLDM), Variance, Mean Absolute Deviation, Cluster Prominence, Sum Entropy LLL, Interquartile Range LLL, Gray Level Variance LLL (GLSZM), Sum of Squares, Robust Mean Absolute Deviation, Sum Entropy, Interquartile Range, Cluster Prominence LLL, Entropy LLL, 10th Percentile LLL, and 10th Percentile; and cluster 9 consists of Size Zone Non Uniformity LLL, Dependence Non Uniformity HLL, Gray Level Non Uniformity HLL (GLSZM), Gray Level Non Uniformity (GLSZM), Run Length Non Uniformity HHL, and Run Length Non Uniformity LHL.

Clause 6. The method of clause 2, wherein:

cluster 1 consists of Short Run High Gray Level Emphasis, High Gray Level Emphasis, and High Gray Level Run Emphasis;

cluster 2 consists of Skewness, and Skewness LLL;

cluster 3 consists of Run Entropy;

cluster 4 consists of Small Area Low Gray Level Emphasis, and Low Gray Level Zone Emphasis;

cluster 5 consists of Zone Entropy;

cluster 6 consists of Zone Entropy HHH;

cluster 7 consists of Strength;

cluster 8 consists of Cluster Tendency LLL, Cluster Tendency, Sum of Squares LLL, Mean Absolute Deviation LLL, Gray Level Variance LLL (GLDM), Variance LLL, Gray Level Variance LLL (GLRLM), Gray Level Variance (GLRLM), Robust Mean Absolute Deviation LLL, Gray Level Variance (GLDM), Variance, Mean Absolute Deviation, Cluster Prominence, Sum Entropy LLL, Interquartile Range LLL, Gray Level Variance LLL (GLSZM), Sum of Squares, Robust Mean Absolute Deviation, and Sum Entropy; and cluster 9 consists of Size Zone Non Uniformity LLL.

Clause 7. The method of clause 2, wherein:

cluster 1 consists of Short Run High Gray Level Emphasis, High Gray Level Emphasis, and High Gray Level Run Emphasis;

cluster 2 consists of Skewness, Skewness LLL, Kurtosis, 90th Percentile, Median LLL, Kurtosis LLL, and Median;

cluster 3 consists of Run Entropy, Run Entropy LLL, and Mean LLL;

cluster 4 consists of Small Area Low Gray Level Emphasis, Low Gray Level Zone Emphasis, and Gray Level Variance (GLSZM);

cluster 5 consists of Zone Entropy, Gray Level Non Uniformity Normalized (GLRLM), and Uniformity;

cluster 6 consists of Zone Entropy HHH;

cluster 7 consists of Strength;

cluster 8 consists of Cluster Tendency LLL, Cluster Tendency, Mean Absolute Deviation LLL, Gray Level Variance LLL (GLDM), Variance LLL, Gray Level Variance LLL (GLRLM), Robust Mean Absolute Deviation LLL, Gray Level Variance LLL (GLSZM), Interquartile Range LLL, Sum Entropy LLL, Gray Level Variance (GLRLM), Variance, Gray Level Variance (GLDM), Mean Absolute Deviation, Sum Entropy, Robust Mean Absolute Deviation, Interquartile Range, Entropy LLL, 10th Percentile LLL, 10th Percentile, Entropy, Uniformity LLL, Gray Level Non Uniformity Normalized LLL (GLDM), Gray Level Non Uniformity Normalized LLL (GLRLM), Root Mean Squared, Gray Level Non Uniformity Normalized (GLDM), Root Mean Squared LLL, and Long Run Low Gray Level Emphasis; and cluster 9 consists of Size Zone Non Uniformity LLL, Busyness, and Size Zone Non Uniformity.

Clause 8. The method of clause 1, wherein the at least two radiomic features are selected from: Median LLL, Mean LLL, Median, Root Mean Squared LLL, Mean, Kurtosis, Root Mean Squared, Run Entropy LLL (GLRLM), Uniformity, 90th Percentile, Gray Level Non-Uniformity Normalized (GLRLM), Uniformity LLL, Skewness, Gray Level Non-Uniformity Normalized LLL (GLRLM), 10th Percentile LLL, Skewness LLL, 10th Percentile, Entropy, Interquartile Range LLL, Robust Mean Absolute Deviation LLL, Run Entropy (GLRLM), Interquartile Range, Sum Entropy (GLCM), Gray Level Non-Uniformity Normalized LLL (GLRLM), Dependence Non-Uniformity LHL (GLDM), Kurtosis LLL, Run Length Non-Uniformity HHL (GLRLM), Entropy LLL, Robust Mean Absolute Deviation, Sum Entropy LLL (GLCM), 90th Percentile LLL, Run Entropy HHL (GLRLM), Energy, Energy LLL, Strength (NGTDM), Autocorrelation (GLCM), Mean Absolute Deviation LLL, High Gray Level Emphasis (GLDM), Joint Average (GLCM), Sum Average (GLCM), Short Run High Gray Level Emphasis (GLRLM), Energy HHH, High Gray Level Run Emphasis (GLRLM), Run Entropy HHH (GLRLM), Energy HHL, and Mean Absolute Deviation.

Clause 9. The method of any one of clauses 2 to 7, wherein the at least two radiomic features are selected from the radiomic features of clusters 1 to 8.

Clause 10. The method of any one of clauses 2 to 7, wherein the at least two radiomic features are selected from the radiomic features of clusters 1 to 7.

Clause 11. The method of any one of clauses 2 to 7, wherein the at least two radiomic features are selected from the radiomic features of clusters 1 to 6.

Clause 12. The method of any one of clauses 2 to 7, wherein the at least two radiomic features are selected from the radiomic features of clusters 1 to 5.

Clause 13. The method of any one of clauses 2 to 7, wherein the at least two radiomic features are selected from the radiomic features of clusters 1 to 4.

Clause 14. The method of any one of clauses 2 to 7, wherein the at least two radiomic features are selected from the radiomic features of clusters 1 to 3.

Clause 15. The method of any one of clauses 2 to 7, wherein the at least two radiomic features are selected from the radiomic features of clusters 1 and 2.

Clause 16. The method of any one of clauses 1 to 14, wherein the at least two radiomic features comprises at least three radiomic features.

Clause 17. The method of any one of clauses 1 to 13, wherein the at least two radiomic features comprises at least four radiomic features.

Clause 18. The method of any one of clauses 1 to 12, wherein the at least two radiomic features comprises at least five radiomic features.

Clause 19. The method of any one of clauses 1 to 11, wherein the at least two radiomic features comprises at least six radiomic features.

Clause 20. The method of any one of clauses 1 to 10, wherein the at least two radiomic features comprises at least seven radiomic features.

Clause 21. The method of any one of clauses 1 to 9, wherein the at least two radiomic features comprises at least eight radiomic features.

Clause 22. The method of any one of clauses 1 to 8, wherein the at least two radiomic features comprises at least nine radiomic features.

Clause 23. The method of clause 1, wherein the at least two radiomic features comprises six radiomic features, wherein the six radiomic features are Short Run High Gray Level Emphasis, Skewness, Run Entropy, Small Area Low Gray Level Emphasis, Zone Entropy HHH, and Zone Entropy.

The invention claimed is:

1. A method for characterising a perivascular region comprising perivascular tissue using medical imaging data of a subject, the method comprising calculating the value of a radiomic signature of the perivascular region using the medical imaging data;

wherein the radiomic signature is calculated on the basis of measured values of at least two radiomic features of the perivascular region, the measured values of the at least two radiomic features being calculated from the medical imaging data.

2. The method of claim 1, wherein the radiomic signature provides a measure of the texture of the perivascular region.

3. The method of claim 1, wherein the radiomic signature is predictive of cardiovascular risk, optionally wherein the radiomic signature is predictive of the likelihood of the subject experiencing a major adverse cardiovascular event.

4. The method of claim 1, wherein at least one of the at least two radiomic features is calculated from a wavelet transformation of the attenuation values.

5. The method of claim 1, wherein the at least two radiomic features are selected from the radiomic features of clusters 1 to 9, wherein the at least two radiomic features are each selected from different clusters, wherein:

cluster 1 consists of Short Run High Gray Level Emphasis, High Gray Level Emphasis, High Gray Level Run Emphasis, Autocorrelation, Sum Average, Joint Average, and High Gray Level Zone Emphasis;

cluster 2 consists of Skewness, Skewness LLL, Kurtosis, 90th Percentile, 90th Percentile LLL, Median LLL, Kurtosis LLL, and Median;

cluster 3 consists of Run Entropy, Dependence Entropy LLL, Dependence Entropy, Zone Entropy LLL, Run Entropy LLL, and Mean LLL;

cluster 4 consists of Small Area Low Gray Level Emphasis, Low Gray Level Zone Emphasis, Short Run Low Gray Level Emphasis, Low Gray Level Run Emphasis, Low Gray Level Emphasis, Small Dependence Low Gray Level Emphasis, Gray Level Variance LLL (GLSZM), Gray Level Variance (GLDM), Variance, Gray Level Variance (GLDM), Difference Variance LLL, Gray Level Variance LLL (GLRLM), Variance LLL, Gray Level Variance LLL (GLDM), Sum of Squares, Contrast LLL, Mean Absolute Deviation, Interquartile Range, Robust Mean Absolute Deviation, Long Run Low Gray Level Emphasis, Difference Variance, Gray Level Variance (GLSZM), Inverse Difference Moment Normalized, Mean Absolute Deviation LLL, Sum of Squares LLL, and Contrast;

cluster 5 consists of Zone Entropy, Gray Level Non Uniformity Normalized (GLRLM), Gray Level Non Uniformity Normalized LLL (GLRLM), Sum Entropy, Joint Energy, Entropy, Gray Level Non Uniformity Normalized (GLDM), Joint Energy, Gray Level Non Uniformity Normalized LLL (GLDM), Uniformity LLL, Sum Entropy LLL, and Uniformity;

cluster 6 consists of Zone Entropy HHH, Size Zone Non Uniformity Normalized HHH, and Small Area Emphasis HHH;

cluster 7 consists of Strength, Coarseness HLL, Coarseness, Coarseness LHL, Coarseness LLL, Coarseness LLH, Coarseness HHH, Coarseness HLH, Coarseness HHL, and Coarseness LHH;

cluster 8 consists of Cluster Tendency LLL, Cluster Tendency, Sum of Squares LLL, Mean Absolute Deviation LLL, Gray Level Variance LLL (GLDM), Variance LLL, Gray Level Variance LLL (GLRLM), Gray Level Variance (GLRLM), Robust Mean Absolute Deviation LLL, Gray Level Variance (GLDM), Variance, Mean Absolute Deviation, Cluster Prominence, Sum Entropy LLL, Interquartile Range LLL, Gray Level Variance LLL (GLSZM), Sum of Squares, Robust Mean Absolute Deviation, Sum Entropy, Interquartile Range, Cluster Prominence LLL, Entropy LLL, 10th Percentile LLL, 10th Percentile; and cluster 9 consists of Size Zone Non Uniformity LLL, Dependence Non Uniformity HLL, Gray Level Non Uniformity HLL (GLSZM), Gray Level Non Uniformity (GLSZM), Run Length Non Uniformity HHL, Run Length Non Uniformity LHL, Dependence Non Uniformity LHL, Dependence Non Uniformity, Run Length Non Uniformity HLH, Busyness, Run Length Non Uniformity LLH, Dependence Non Uniformity LLH, Dependence Non Uniformity LLL, Size Zone Non Uniformity, Energy HLL, Run Length Non Uniformity LHH, Size Zone Non Uniformity HLL, Gray Level Non Uniformity LLH (GLSZM), Gray Level Non Uniformity LHL (GLSZM), Gray Level Non Uniformity LLL (GLSZM), Run Length Non Uniformity HLL, Gray Level Non Uniformity HLH (GLSZM), Gray Level Non Uniformity HHL (GLSZM), Run Length Non Uniformity, and Run Length Non Uniformity HHH.

6. The method of claim 1, wherein the at least two radiomic features are selected from: Median LLL, Mean LLL, Median, Root Mean Squared LLL, Mean, Kurtosis, Root Mean Squared, Run Entropy LLL (GLRLM), Uniformity, 90th Percentile, Gray Level Non-Uniformity Normalized (GLRLM), Uniformity LLL, Skewness, Gray Level Non-Uniformity Normalized LLL (GLRLM), 10th Percentile LLL, Skewness LLL, 10th Percentile, Entropy, Interquartile Range LLL, Robust Mean Absolute Deviation LLL, Run Entropy (GLRLM), Interquartile Range, Sum Entropy (GLCM), Gray Level Non-Uniformity Normalized LLL (GLRLM), Dependence Non-Uniformity LHL (GLDM), Kurtosis LLL, Run Length Non-Uniformity HHL (GLRLM), Entropy LLL, Robust Mean Absolute Deviation, Sum Entropy LLL (GLCM), 90th Percentile LLL, Run Entropy HHL (GLRLM), Energy, Energy LLL, Strength (NGTDM), Autocorrelation (GLCM), Mean Absolute Deviation LLL, High Gray Level Emphasis (GLDM), Joint Average (GLCM), Sum Average (GLCM), Short Run High Gray Level Emphasis (GLRLM), Energy HHH, High Gray Level Run Emphasis (GLRLM), Run Entropy HHH (GLRLM), Energy HHL, and Mean Absolute Deviation.

7. The method of claim 5, wherein the at least two radiomic features are selected from the radiomic features of clusters 1 to 6.

8. The method of claim 1, wherein the at least two radiomic features comprises at least six radiomic features.

9. The method of claim 1, further comprising predicting the risk of the subject experiencing a major adverse cardiac event based on at least the calculated value of the radiomic signature.

10. The method of claim 1, further comprising determining whether the subject has vascular disease or coronary heart disease based on at least the calculated value of the radiomic signature, or wherein the calculated value of the radiomic signature is used to discriminate unstable from stable coronary lesions.

11. The method of claim 1, wherein the perivascular region comprises perivascular adipose tissue.

12. The method of claim 1, wherein the radiomic signature is calculated on the basis of further radiomic features of the perivascular region in addition to the at least two radiomic features.

13. A system configured to perform the method of claim 1.

14. A method for deriving a radiomic signature for predicting cardiovascular risk, the method comprising using a radiomic dataset to construct a perivascular radiomic signature for predicting cardiovascular risk, the radiomic signature being calculated on the basis of at least two radiomic features of a perivascular region comprising perivascular tissue;

wherein the dataset comprises the values of a plurality of radiomic features of a perivascular region obtained from medical imaging data for each of a plurality of individuals, the plurality of individuals comprising a first group of individuals having reached a clinical endpoint indicative of cardiovascular risk within a subsequent period after the collection of the medical imaging data and a second group of individuals having not reached a clinical endpoint indicative of cardiovascular risk within the subsequent period.

15. The method of claim 14, further comprising identifying radiomic features from amongst the plurality of radiomic features, which identified radiomic features are each associated with the clinical endpoint, the at least two radiomic features each being selected to be, or to be collinear with, different identified radiomic features.

16. The method of claim 15, further comprising identifying a subset of the identified radiomic features that are not collinear with each other, the at least two radiomic features each being selected to be, or to be collinear with, different radiomic features belonging to the subset.

17. The method of claim 14, wherein each of the at least two radiomic features is selected to be collinear with a corresponding partner radiomic feature that is associated with the clinical endpoint, the partner radiomic features of the at least two radiomic features each being different to one another, optionally wherein each of the partner radiomic features is selected to be not collinear with any of the other partner radiomic features, and further optionally wherein at least one of the at least two radiomic features is its own partner radiomic feature.

18. The method of claim 14, wherein the method comprises identifying a plurality of clusters of radiomic features, each cluster comprising a subset of the plurality of radiomic features, wherein each cluster comprises an original radiomic feature with which each of the other radiomic features in that cluster is selected to be collinear, and wherein the at least two radiomic features are each selected from different clusters, optionally wherein each of the original radiomic features is selected to be not collinear with any of the original radiomic features of any of the other clusters.

19. The method of claim 14, wherein the at least two radiomic features are selected to be not collinear with each other.

20. The method of claim 14, wherein the radiomic signature is constructed to be correlated with the clinical endpoint, optionally wherein the radiomic signature is constructed to be associated with the clinical endpoint.

21. The method of claim 14, wherein the at least two radiomic features are selected to be stable.

22. The method of claim 14, wherein the step of constructing the radiomic signature is performed using a machine learning algorithm.

23. The method of claim 14, wherein the radiomic signature is constructed to provide a measure of the texture of the perivascular region.

24. The method of claim 14, further comprising configuring a system for calculating the value of the radiomic signature for a patient.

25. The method of claim 14, further comprising characterising a perivascular region of a patient by calculating the value of the radiomic signature for the perivascular region of the patient.

* * * * *